United States Patent
Guo et al.

(10) Patent No.: US 12,172,975 B2
(45) Date of Patent: Dec. 24, 2024

(54) 1H-INDAZOLE CARBOXAMIDES AS RECEPTOR-INTERACTING PROTEIN KINASE 1 INHIBITORS (RIPK1)

(71) Applicant: BRISTOL-MYERS SQUIBB COMPANY, Princeton, NJ (US)

(72) Inventors: Junqing Guo, Princeton, NJ (US); Jie Chen, Cambridge, MA (US); Carolyn Diane Dzierba, Medford, MA (US); Amy C. Hart, Ewing, NJ (US); Guanglin Luo, Newtown, PA (US); John E. Macor, Washington Crossing, PA (US); William J. Pitts, Newtown, PA (US); Sing-Yuen Sit, Meridian, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 883 days.

(21) Appl. No.: 17/274,220

(22) PCT Filed: Sep. 12, 2019

(86) PCT No.: PCT/US2019/050719
§ 371 (c)(1),
(2) Date: Mar. 8, 2021

(87) PCT Pub. No.: WO2020/056072
PCT Pub. Date: Mar. 19, 2020

(65) Prior Publication Data
US 2022/0380335 A1      Dec. 1, 2022

Related U.S. Application Data

(60) Provisional application No. 62/730,602, filed on Sep. 13, 2018.

(51) Int. Cl.
*C07D 401/04* (2006.01)
*C07D 401/14* (2006.01)
*C07D 405/14* (2006.01)

(52) U.S. Cl.
CPC ......... *C07D 401/04* (2013.01); *C07D 401/14* (2013.01); *C07D 405/14* (2013.01); *C07B 2200/05* (2013.01)

(58) Field of Classification Search
None
See application file for complete search history.

(56) References Cited

U.S. PATENT DOCUMENTS

| | | |
|---|---|---|
| 8,598,217 B2 | 12/2013 | Howard et al. |
| 9,546,153 B2 | 1/2017 | Bhide |
| 9,745,271 B2 | 8/2017 | Hood et al. |
| 10,913,738 B2 | 2/2021 | Guo et al. |
| 2011/0190343 A1 | 8/2011 | Gochin et al. |
| 2021/0309633 A1* | 10/2021 | Guo .................. C07D 401/04 |

FOREIGN PATENT DOCUMENTS

| | | | |
|---|---|---|---|
| WO | 2005009389 A2 | 2/2005 | |
| WO | 2006069097 A2 | 6/2006 | |
| WO | 2007137030 A2 | 11/2007 | |
| WO | 2010064875 A2 | 6/2010 | |
| WO | 2010068287 A2 | 6/2010 | |
| WO | WO-2013100672 A1 * | 7/2013 | .......... C07D 231/56 |
| WO | 2013124158 A1 | 8/2013 | |
| WO | 2013124169 A1 | 8/2013 | |
| WO | 2017201585 A1 | 11/2017 | |
| WO | 2018148626 A1 | 8/2018 | |
| WO | 2019089442 A1 | 5/2019 | |
| WO | 2019147782 A1 | 8/2019 | |
| WO | 2020056074 A1 | 3/2020 | |
| WO | 2021067654 A1 | 4/2021 | |

OTHER PUBLICATIONS

Coskun et al., Clin Chim Acta. Mar. 18, 2011;412(7-8):513-20 (Year: 2011).*
Chan, et al., Int. J. Mol. Sci. 2017, 18, 1527 (Year: 2017).*
U.S. Appl. No. 17/116,016, Bristol-Myers Squibb Company.
U.S. Appl. No. 17/274,220, Bristol-Myers Squibb Company.
U.S. Appl. No. 17/274,227, Bristol-Myers Squibb Company.
Amour et al., "Evolution of a Novel, Orally Bioavailable Series of PI3KO Inhibitors from an Inhaled Lead for the Treatment of Respiratory Disease", J. Med. Chem. vol. 59, pp. 7239-7251 (2016).
Caballero et al., "Binding Studies and Quantitative Structure-Activity Relationship of 3-Amino-IH-Indazoles as Inhibitors of GSK3beta", Chemical Biological & Drug Design, vol. 78, pp. 631-641, (2011).
Cho et al., "Phosphorylation-Driven Assembly of the RIP1-RIP3 Complex Regulates Programmed Necrosis and Virus-Induced Inflammation", Cell vol. 137, pp. 1112-1123 (2009).

(Continued)

*Primary Examiner* — Jeffrey S Lundgren
*Assistant Examiner* — Anthony Joseph Seitz
(74) *Attorney, Agent, or Firm* — Mary K. VanAtten

(57) ABSTRACT

Compounds having formula (I), and enantiomers, and diastereomers, stereoisomers, pharmaceutically-acceptable salts thereof, (I) are useful as kinase modulators, including RIPK1 modulation. All the variables are as defined herein.

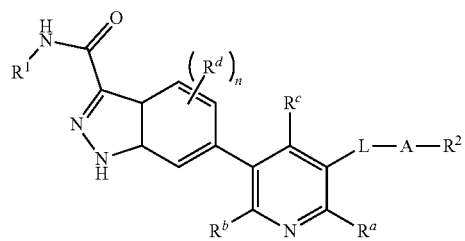

(I)

12 Claims, No Drawings

(56) References Cited

OTHER PUBLICATIONS

Degterev et al., "Chemical inhibitor of nonapoptotic cell death with therapeutic potential for ischemic brain injury", Nat. Chem. Biol., vol. 1, pp. 112-119 (2005).

Degterev et al., "Identification of RIP1 kinase as a specific cellular target of necrostatins", Nat. Chem. Biol. vol. 4, pp. 313-321 (2008).

Duprez et al., "RIP Kinase-Dependent Necrosis Drives Lethal Systemic Inflammatory Response Syndrome", Immunity vol. 35, pp. 908-918 (2011).

Festjens et al., "Necrosis, a well-orchestrated form of cell demise: Signalling cascades, important mediators and concomitant immune response", Biochimica et Biophysica Acta vol. 1757, pp. 1371-1387 (2006).

Fukuda et al., "Discovery of DS28120313 as a potent orally active hepcidin production inhibitor: Design and optimization of novel 4,6-disubstituted indazole derivatives", Bioorganic & Medicinal Chemistry Letters vol. 27, pp. 5252-5257 (2017).

Golstein et al., "Cell death by necrosis: towards a molecular definition", TRENDS in Biochemical Sciences vol. 32 No. 1, pp. 37-43.

He et al., "Receptor Interacting Protein Kinase-3 Determines Cellular Necrotic Response to TNF-a", Cell vol. 137, pp. 1100-1111 (2009).

Holler et al., "Fas triggers an alternative, caspase-8-independent cell death pathway using the kinase RIP as effector molecule", Nature America Inc., Immunol. vol. 1, pp. 489-495 (2009).

Ito et al., "RIPK1 mediates axonal degeneration by promoting inflammation and necroptosis in ALS", Science vol. 353, pp. 603-608 (2016).

Kroemer et al., "Classification of cell death: recommendations of the Nomenclature Committee on Cell Death", Cell Death and Differentiation vol. 16, pp. 3-11 (2009).

Lin et al., "A Role of RIP3-Mediated Macrophage Necrosis in Atherosclerosis Development", Cell Reports vol. 3, pp. 200-210 (2013).

Moriwaki et al., "RIP3: a molecular switch for necrosis and inflammation", Genes & Development vol. 27, pp. 1640-1649 (2013).

Roychowdhury et al., "Absence of Receptor Interacting Protein Kinase 3 Prevents Ethanol-Induced Liver Injury", Hepatology vol. 57, pp. 1773-1783 (2013).

Trichonas et al., "Receptor interacting protein kinases mediate retinal detachment-induced photoreceptor necrosis and compensate for inhibition of apoptosis", Proc. Natl. Acad. Sci. vol. 107, pp. 21695-21700 (2010).

Vandenabeele et al., "Molecular mechanisms of necroptosis: an ordered cellular explosion", Nature, vol. 10, pp. 700-714 (2010).

Vandenabeele et al., "The Role of the Kinases RIP1 and RIP3 in TNF-Induced Necrosis", Science Signaling vol. 3, pp. 1-8 (2010).

Vitner et al., "RIPK3 as a potential therapeutic target for Gaucher's disease", Nature Medicine vol. 20, pp. 204-208 (2014).

Zhang et al., "Receptor-interacting protein (RIP) kinase family", Cellular & Molecular Immunology vol. 7, pp. 243-249 (2010).

Zhang et al., RIP3, an Energy Metabolism Regulator That Switches TNF-Induced Cell Death from Apoptosis to Necrosis, Science vol. 325 pp. 332-336 (2009).

\* cited by examiner

1H-INDAZOLE CARBOXAMIDES AS RECEPTOR-INTERACTING PROTEIN KINASE 1 INHIBITORS (RIPK1)

CROSS REFERENCE TO RELATED APPLICATIONS

This application is a 371 application of PCT/US2019/050719 filed Sep. 12, 2019, which is entitled to priority pursuant to 35 U.S.C. § 119 (e) to U.S. provisional patent application No. 62/730,602, filed Sep. 13, 2018, which is incorporated herein in its entirety.

FIELD OF THE INVENTION

The present invention relates to novel compounds that inhibit receptor interacting protein kinases and methods of making and using the same. Specifically, the present invention relates to indazolecarboxamides as receptor interacting protein kinase 1 (RIPK1) inhibitors.

BACKGROUND OF THE INVENTION

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer et al., (2009) Cell Death Differ 16:3-11). Necrosis has been considered a passive, unregulated form of cell death; however, recent evidence indicates that some necrosis can be induced by regulated signal transduction pathways such as those mediated by receptor interacting protein kinases (RIPKs) especially in conditions where caspases are inhibited or cannot be activated efficiently (Golstein P & Kroemer G (2007) Trends Biochem. Sci. 32:37-43; Festjens et al. (2006) Biochim. Biophys. Acta 1757:1371-1387). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor Z-VAD, stimulation of death domain receptors (DR) causes a receptor interacting protein kinase 1 (RIPK1) dependent programmed necrotic cell death instead of apoptosis (Holler et al. (2000) Nat. Immunol. 1:489-495; Degterev et al. (2008) Nat. Chem. Biol. 4:313-321). This novel mechanism of cell death is termed "programmed necrosis" or "necroptosis" (Degterev et al., (2005) Nat Chem Biol 1:112-119).

Necroptosis can be triggered by a number of mechanisms including of TNF receptor activation, Toll-like receptor engagement, genotoxic stress and viral infection. Downstream of the various stimuli, the signaling pathway that results in necroptosis is dependent on RIPK1 and RIPK3 kinase activity. (He et al., (2009) Cell 137:1100-1111; Cho et. al., (2009) Cell 137:1112-1123; Zhang et al., (2009) Science 325:332-336).

Dysregulation of the necroptosis signaling pathway has been linked to inflammatory diseases such as macrophage necrosis in atheroscelerosis development, virus-induced inflammation, systemic inflammatory response syndrome and ethanol-induced liver injury, neurodegeneration such as detachment of the retina, ischemia, amyotrophic lateral sclerosis (ALS), and Gaucher's disease (Trichonas et al., (2010) Proc. Natl. Acad. Sci. 107, 21695-21700; Lin et al., (2013) Cell Rep. 3, 200-210; Cho et al., (2009) Cell, 137, 1112-1123; Duprez et al., (2011) Immunity 35, 908-918; Roychowdhury et al., Hepatology 57, 1773-1783; Vandenabeele et al., (2010) Nature 10, 700-714; Vandenabeele et al., (2010) Sci. Signalling 3, 1-8; Zhang et al., (2010) Cellular & Mol. Immunology 7, 243-249; Moriwaki et al., (2013) Genes Dev. 27, 1640-1649; Ito et al., (2016) Science 353, 603-608; Vitner et al., (2014) Nature Med. 20, 204-208).

A potent, selective, small molecule inhibitor of RIPK1 activity would block RIPK1-dependent pro-inflammatory signaling and thereby provide a therapeutic benefit in inflammatory diseases characterized by increased and/or dysregulated RIPK1 kinase activity.

SUMMARY OF THE INVENTION

The present invention provides novel indazolecarboxamides including stereoisomers, tautomers, isotopes, prodrugs, pharmaceutically acceptable salts, salts, or solvates thereof, which are useful as inhibitors of RIPK1.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, isotopes, prodrugs, pharmaceutically acceptable salts, salts, or solvates thereof.

The compounds of the invention may be used in the treatment and/or prophylaxis of conditions associated with aberrant RIPK1 activity.

The compounds of the present invention may be used in therapy.

The compounds of the present invention may be used for the manufacture of a medicament for the treatment and/or prophylaxis of a condition associated with aberrant RIPK1 activity.

In another aspect, the present invention is directed to a method of treating diseases mediated at least partially by RIPK1 including inflammatory diseases, ischemia, neurodegeneration, and Gaucher's disease, which method comprises administering to a patient in need of such treatment a compound of the present invention as described above.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF EMBODIMENTS OF THE INVENTION

In one aspect, the present invention provides, inter alia, compounds of Formula (I) or stereoisomers, tautomers, isotopes, salts, pharmaceutically acceptable salts, solvates, or prodrugs thereof, wherein

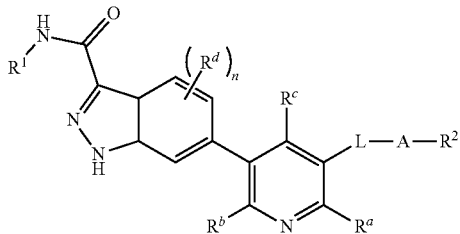

(I)

$R^a$ is H, halo, $C_{1-4}$ alkyl, $C_{1-4}$ alkoxy, $C_{1-4}$ deuteroalkyl, $C_{1-4}$ deuteroalkoxy, cyclopropyl, or $N(R^e)_2$;

$R^b$ is H, halo, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, or $N(R^e)_2$;

$R^c$ is H, $C_{1-4}$ alkyl, $C_{1-4}$ haloalkyl, $C_{1-4}$ deuteroalkyl, or halo;

$R^d$ is independently H, halo, or $C_{1-3}$ alkyl;

$R^e$, is independently at each occurrence, H, $C_{1-4}$ alkyl, or $C_{1-4}$ deuteroalkyl;

$R^1$ is $C_{1-6}$ alkyl, $C_{1-6}$ haloalkyl, $C_{1-6}$ deuteroalkyl, $C_{0-3}$ alkyl-$C_{3-6}$ cycloalkyl, $C_{0-3}$ alkyl-phenyl, $C_{0-3}$ alkyl-heterocycle, wherein the heterocycle is a 3 to 6 membered ring having 1-3 heteroatoms selected from N, S and O, and wherein the alkyl, cycloalkyl, phenyl, or heterocycle are independently substituted with 0-2 of =O, halo, OH, $C_{1-3}$ alkyl, $C_{1-3}$ deuteroalkyl, —C(O)—$C_{1-3}$ alkyl, —SO$_2$—$C_{1-3}$ alkyl, —N(R$^{1e}$)$_2$, phenyl, or phenyl-O—$C_{1-3}$ alkyl;

$R^{1e}$, is independently at each occurrence, H, $C_{1-4}$ alkyl, or $C_{1-4}$ deuteroalkyl;

L is —C(O)NR$^e$—; and

A is $A^1$ or -$A^1$-$L^1$-, wherein $A^1$ is $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ deuteroalkyl, $C_{1-6}$ haloalkyl, $C_{0-3}$ alkyl-$C_{3-10}$ cycloalkyl-$C_{0-3}$-alkyl, $C_{0-3}$-alkyl-phenyl, $C_{0-3}$-alkyl-heterocycle, wherein the heterocycle is a 3 to 6 membered ring having 1-3 heteroatoms selected from N, S and O, and wherein the cycloalkyl, phenyl and heterocycle are substituted with 0-2 $R^8$;

$L^1$ is —O—, —S—, —C(O)—, —C(O)NR$^e$, —SO$_2$NH—, —NHSO$_2$—, —C(O)O—, —NR$^e$—C(O)—, —NR$^e$—C(O)O—, —NR$^e$—C(O)NR$^e$—, —SO$_2$—, or —NH—R$^e$—;

or alternatively, -L-A- is

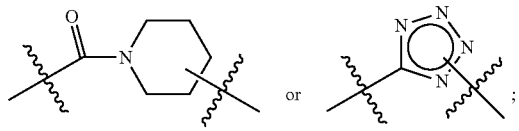

$R^2$ is $C_{1-6}$ alkyl, $C_{1-6}$ haloalkyl, $C_{0-3}$alkyl-$C_{6-10}$ aryl, $C_{0-3}$alkyl-$C_{3-6}$ cycloalkyl, or a $C_{0-3}$alkyl-3 to 6 membered heterocycle having 1-4 heteroatoms selected from N, S and O, wherein any of the aryl, cycloalkyl, or heterocycle groups are substituted with 0-3 $R^{2a}$;

$R^{2a}$ is halo, CN, =O, $C_{1-6}$ alkyl, $C_{1-6}$ alkoxy, hydroxy-$C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{0-3}$ alkyl-$C_{3-6}$ cycloalkyl-$C_{0-3}$ alkyl, $C_{3-6}$ halocycloalkyl, $C_{3-6}$ cycloalkyl, $C_{3-6}$ cycloalkyl-$C_{1-6}$ alkoxy, $C_{6-10}$ aryl, phenyl-$C_{1-3}$ alkoxy-, $C_{3-6}$ cycloalkyl-$C_{1-3}$ deuteroalkoxy-, $C_{3-6}$ cycloalkyl-$C_{1-3}$ haloalkoxy-, $C_{1-6}$ alkoxy-$C_{1-3}$ alkyl-, $C_{3-6}$ cycloalkoxy-$C_{1-3}$ alkyl-, $C_{6-10}$ aryl-O-phenyl $C_{1-4}$ alkyl-SO$_2$—, $C_{3-6}$ cycloalkyl-SO$_2$—, $C_{6-10}$ aryl-S—, NR$^6$R$^6$CO—, NHR$^6$—(CH$_2$)$_n$—, R$^5$—C(O)—, R$^5$—OC(O)—, R$^5$—C(O)O—, R$^6$—NH—C(O)O—, R$^7$—OC(O)NH—, R$^6$—NH—C(O)NR$^6$, R$^7$—SO$_2$—, R$^5$—SO$_2$NH—, R$^5$—NHSO$_2$—, heterocycle, heterocycle-O—, or heterocycle-$C_{0-6}$ alkyl-, wherein each heterocycle is independently a 4-6 membered ring having 1-2 heteroatoms selected from N, S and O, and wherein each alkyl, cycloalkyl, phenyl, or heterocycle is substituted with 0-3 $R^{2b}$;

$R^{2b}$, at each occurrence, is independently halo, OH, $C_{1-3}$ alkyl, $C_{1-3}$ alkoxy, hydroxy-$C_{1-3}$ alkoxy, hydroxy-$C_{1-3}$ alkyl, C=O, $C_{1-3}$ haloalkyl, or $C_{1-3}$ haloalkoxy;

$R^5$ is, independently at each occurrence, H, $C_{1-6}$ alkyl, $C_{0-3}$ alkyl-$C_{3-6}$ cycloalkyl, $C_{0-3}$ alkyl-phenyl or $C_{1-6}$ haloalkyl;

$R^6$ is, independently at each occurrence, H, $C_{1-6}$ alkyl, $C_{0-3}$ alkyl-$C_{3-6}$ cycloalkyl, $C_{0-3}$ alkyl-phenyl;

$R^7$ is, independently at each occurrence, $C_{1-6}$ alkyl, $C_{0-3}$ alkyl-$C_{3-6}$ cycloalkyl, $C_{0-3}$ alkyl-phenyl;

$R^8$ is, independently at each occurrence, H, halo, C=O, $C_{1-6}$ alkyl, $C_{1-6}$ alkoxy, $C_{1-6}$ haloalkyl, $C_{3-6}$ cycloalkyl, phenyl, a 3 to 6 membered heterocycle, —(CH$_2$)$_n$—NR$^6$R$^6$CO, —(CH$_2$)$_n$—NR$^6$R$^6$CONR$^6$R$^6$, —(CH$_2$)$_n$—NR$^6$, —(CH$_2$)$_n$—C(O)—R$^5$, —(CH$_2$)$_n$—C(O)O—R$^5$, —(CH$_2$)$_n$—OC(O)—R$^5$, —(CH$_2$)$_n$—OC(O)—NH—R$^6$, —(CH$_2$)$_n$—NHC(O)—O—R$^7$, —(CH$_2$)$_n$—SO$_2$—R$^7$, —(CH$_2$)$_n$—SO$_2$NH—R$^5$, —(CH$_2$)$_n$—NHSO$_2$—R$^5$, wherein each heterocycle is independently a 4-6 membered ring having 1-2 heteroatoms selected from N, S and O; and n is 0, 1, or 2.

Another embodiment provides a compound of Formula (I), or stereoisomers, tautomers, isotopes, salts, pharmaceutically acceptable salts, solvates, or prodrugs thereof, wherein

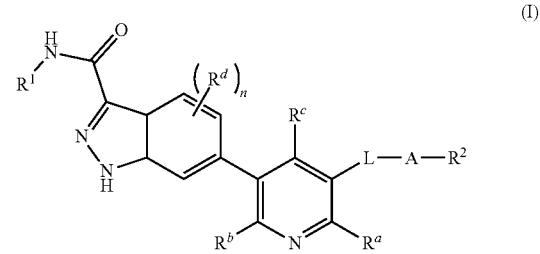

(I)

$R^a$ is H, halo, $C_{1-4}$ alkyl, $C_{1-4}$ alkoxy, $C_{1-4}$ deuteroalkyl, $C_{1-4}$ deuteroalkoxy, cyclopropyl, or $N(R^e)_2$;

$R^b$ is H, halo, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, halo, or NR$^e_2$;

$R^c$ is H, $C_{1-4}$ alkyl, $C_{1-4}$ haloalkyl, $C_{1-4}$ deuteroalkyl, or halo;

$R^d$ is independently H, halo, or $C_{1-3}$ alkyl;

$R^e$, is independently at each occurrence, H, $C_{1-4}$ alkyl, or $C_{1-4}$ deuteroalkyl;

$R^1$ is $C_{1-6}$ alkyl, $C_{1-6}$ haloalkyl, $C_{1-6}$ deuteroalkyl, $C_{0-3}$ alkyl-$C_{3-6}$ cycloalkyl, $C_{0-3}$ alkyl-phenyl, $C_{0-3}$ alkyl-heterocycle, wherein the heterocycle is a 3 to 6 membered ring having 1-3 heteroatoms selected from N, S and O, and wherein the alkyl, cycloalkyl, phenyl, or heterocycle are independently substituted with 0-2 of =O, halo, OH, $C_{1-3}$ alkyl, $C_{1-3}$ deuteroalkyl, phenyl, or phenyl-O—$C_{1-3}$ alkyl;

L is —C(O)NR$^e$—; and

A is A$^1$ or -A$^1$-L$^1$-, wherein A$^1$ is $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ deuteroalkyl, $C_{1-6}$ haloalkyl, $C_{0-3}$ alkyl-$C_{3-10}$ cycloalkyl-$C_{0-3}$-alkyl, $C_{0-3}$-alkyl-phenyl, $C_{0-3}$-alkyl-heterocycle, wherein the heterocycle is a 3 to 6 membered ring having 1-3 heteroatoms selected from N, S and O, and wherein the cycloalkyl, phenyl and heterocycle are substituted with 0-2 R$^8$;

L$^1$ is —O—, —S—, —C(O)—, —C(O)NR$^e$, —SO$_2$NH—, —NHSO$_2$—, —C(O)O—, —NR$^e$—C(O)—, —NR$^e$—C(O)O—, —NR$^e$—C(O)NR$^e$—, —SO$_2$—, or —N—R$^e$—;

or alternatively, -L-A- is —

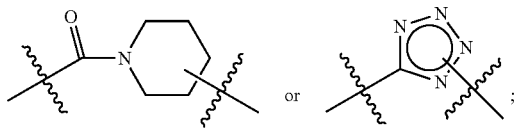

R$^2$ is $C_{1-6}$ alkyl, $C_{1-6}$ haloalkyl, $C_{0-3}$alkyl-$C_{6-10}$ aryl, $C_{0-3}$alkyl-$C_{3-6}$ cycloalkyl, or a $C_{0-3}$ alkyl-3 to 6 membered heterocycle having 1-4 heteroatoms selected from N, S and O, wherein any of the aryl, cycloalkyl, or heterocycle groups are substituted with 0-3 R$^{2a}$;

R$^{2a}$ is halo, CN, =O, $C_{1-6}$ alkyl, $C_{1-6}$ alkoxy, hydroxy-$C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{0-3}$ alkyl-$C_{3-6}$ cycloalkyl-$C_{0-3}$ alkyl, $C_{3-6}$ halocycloalkyl, $C_{3-6}$ cycloalkoxy, $C_{3-6}$ cycloalkyl-$C_{1-6}$ alkoxy, $C_{6-10}$ aryl, phenyl-$C_{1-3}$ alkoxy-, $C_{3-6}$ cycloalkyl-$C_{1-3}$ deuteroalkoxy-, $C_{3-6}$ cycloalkyl-$C_{1-3}$ haloalkoxy-, $C_{1-6}$ alkoxy-$C_{1-3}$ alkyl-, $C_{3-6}$ cycloalkoxy-$C_{1-3}$ alkyl-, $C_{6-10}$ aryl-O-phenyl $C_{1-4}$ alkyl-SO$_2$—, $C_{3-6}$ cycloalkyl-SO$_2$—, $C_{6-10}$ aryl-S—, NR$^6$R$^6$CO—, NR$^6$—(CH$_2$)$_n$—, R$^5$—C(O)—, R$^5$—OC(O)—, R$^5$—C(O)O—, R$^6$—NH—C(O)O—, R$^7$—OC(O)NH—, R$^6$—NH—C(O)NR$^6$, R$^7$—SO$_2$—, R$^5$—SO$_2$NH—, R$^5$—NHSO$_2$—, heterocycle, heterocycle-O—, heterocycle-C$_{0-6}$ alkyl-, wherein each heterocycle is independently a 4-6 membered ring having 1-2 heteroatoms selected from N, S and O, and wherein each alkyl, cycloalkyl, phenyl, or heterocycle is substituted with 0-3 R$^{2b}$;

R$^{2b}$, at each occurrence, is independently halo, OH, $C_{1-3}$ alkyl, $C_{1-3}$ alkoxy, hydroxy-$C_{1-3}$ alkoxy, hydroxy-$C_{1-3}$ alkyl, C=O, $C_{1-3}$ haloalkyl, or $C_{1-3}$ haloalkoxy;

R$^5$ is, independently at each occurrence, H, $C_{1-6}$ alkyl, $C_{0-3}$ alkyl-$C_{3-6}$ cycloalkyl, $C_{0-3}$ alkyl-phenyl or $C_{1-6}$ haloalkyl;

R$^6$ is, independently at each occurrence, H, $C_{1-6}$ alkyl, $C_{0-3}$ alkyl-$C_{3-6}$ cycloalkyl, $C_{0-3}$ alkyl-phenyl;

R$^7$ is, independently at each occurrence, $C_{1-6}$ alkyl, $C_{0-3}$ alkyl-$C_{3-6}$ cycloalkyl, $C_{0-3}$ alkyl-phenyl;

R$^8$ is, independently at each occurrence, H, halo, C=O, $C_{1-6}$ alkyl, $C_{1-6}$ alkoxy, $C_{1-6}$ haloalkyl, $C_{3-6}$ cycloalkyl, phenyl, a 3 to 6 membered heterocycle, —(CH$_2$)$_n$—NR$^6$R$^6$CO, —(CH$_2$)$_n$—NR$^6$R$^6$CONR$^6$R$^6$, —(CH$_2$)$_n$—NR$^6$, —(CH$_2$)$_n$—C(O)—R$^5$, —(CH$_2$)$_n$—C(O)O—R$^5$, —(CH$_2$)$_n$—OC(O)—R$^5$, —(CH$_2$)$_n$—OC(O)—NH—R$^6$, —(CH$_2$)$_n$—NHC(O)—O—R$^7$, —(CH$_2$)$_n$—SO$_2$—R$^7$, —(CH$_2$)$_n$—SO$_2$NH—R$^5$, —(CH$_2$)$_n$—NHSO$_2$—R$^5$, wherein each heterocycle is independently a 4-6 membered ring having 1-2 heteroatoms selected from N, S and O; and n is 0, 1, or 2.

Another embodiment provides a compound of Formula (I), or stereoisomers, tautomers, isotopes, salts, pharmaceutically acceptable salts, solvates, or prodrugs thereof, wherein R$^a$ is H, Cl, F, Br, $C_{1-4}$ alkyl, $C_{1-4}$ alkoxy, $C_{1-4}$ deuteroalkyl, $C_{1-4}$ deuteroalkoxy, cyclopropyl, or N(R$^e$)$_2$:

R$^b$ is H, F, Cl, Br, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, or NR$^e_2$;

R$^c$ is H, $C_{1-4}$ alkyl, $C_{1-4}$ haloalkyl, $C_{1-4}$ deuteroalkyl, or halo;

R$^d$ is independently H or F;

R$^e$, is independently at each occurrence, H, $C_{1-4}$ alkyl, or $C_{1-4}$ deuteroalkyl;

R$^1$ is $C_{1-6}$ alkyl, $C_{1-6}$ haloalkyl, $C_{1-6}$ deuteroalkyl, $C_{0-3}$ alkyl-$C_{3-6}$ cycloalkyl, $C_{0-3}$ alkyl-$C_{3-6}$ cycloalkyl, $C_{0-3}$ alkyl-piperidinyl, $C_{0-3}$ alkyl-pyrrolidinyl, $C_{0-3}$ alkyl-morpholinyl, $C_{0-3}$ alkyl-pyrrolidinyl, wherein the alkyl, cycloalkyl, piperidinyl, pyrrolidinyl, or morpholinyl are independently substituted with 0-2 of =O, halo, OH, $C_{1-3}$ alkyl, $C_{1-3}$ deuteroalkyl, phenyl, or phenyl-O—$C_{1-3}$ alkyl;

L is —C(O)NR$^e$—; and

A is A$^1$ or -A$^1$-L$^1$ wherein A$^1$ is $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ deuteroalkyl, $C_{1-6}$ haloalkyl, $C_{0-3}$ alkyl-$C_{3-10}$ cycloalkyl-$C_{0-3}$-alkyl, $C_{0-3}$-alkyl-$C_{3-6}$ cycloalkyl-$C_{0-3}$-alkyl, $C_{0-3}$-alkyl-imidazolyl, $C_{0-3}$-alkyl-pyrrolidinyl, $C_{0-3}$-alkyl-tetrahydropyranyl, $C_{0-3}$-alkyl-pyridinyl, wherein the pyrrolidinyl is substituted with 0-2 R$^8$;

L$^1$ is —O—, —C(O)—, —C(O)NR$^e$, —SO$_2$NH—, —C(O)O—, —NR$^e$—C(O)—, —SO$_2$—, or —N—R$^e$—;

or alternatively, -L-A- is —

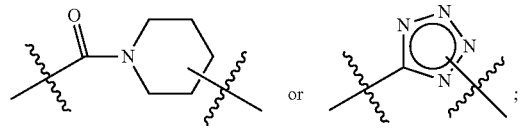

R$^2$ is $C_{1-6}$ alkyl, $C_{1-6}$ haloalkyl, $C_{0-3}$alkyl-phenyl, $C_{0-3}$alkyl-$C_{3-6}$ cycloalkyl, or a $C_{0-3}$ alkyl-3 to 6 membered heterocycle having 1-4 heteroatoms selected from N, S and O, wherein any of the phenyl or heterocycle groups are substituted with 0-3 R$^{2a}$;

R$^{2a}$ is halo, CN, =O, $C_{1-6}$ alkyl, $C_{1-6}$ alkoxy, hydroxy-$C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{1-3}$ alkyl-$C_{3-6}$ cycloalkyl-$C_{0-3}$ alkyl, $C_{3-6}$ halocycloalkyl, $C_{3-6}$ cycloalkoxy, $C_{3-6}$ cycloalkyl-$C_{1-3}$ alkoxy-, $C_{3-6}$ cycloalkyl-$C_{1-3}$ deuteroalkoxy-, $C_{3-6}$ cycloalkyl-$C_{1-3}$ haloalkoxy-, $C_{1-6}$ alkoxy-$C_{1-3}$ alkyl-, $C_{3-6}$ cycloalkoxy-$C_{1-3}$ alkyl-, phenyl-O—, $C_{1-4}$ alkyl-SO$_2$—, $C_{3-6}$ cycloalkyl-SO$_2$—, $C_{6-10}$ aryl-S—, NR$^6$R$^6$CO—, NR$^6$—(CH$_2$)$_n$—, R$^5$—C(O)—, R$^6$—NH—C(O)O—, R$^7$—OC(O)NH—, R$^7$—SO$_2$—, R$^5$—SO$_2$NH—, heterocycle-, heterocycle-O-heterocycle-CH$_2$—, wherein each heterocycle is independently a 4-6 membered ring having 1-2 heteroatoms selected from N, S and O, and wherein each alkyl, cycloalkyl, phenyl, or heterocycle is substituted with 0-3 $R^{2b}$;

$R^{2b}$, at each occurrence, is independently $C_{1-3}$ alkyl, $C_{1-3}$ alkoxy, hydroxy-$C_{1-3}$ alkoxy, halo, C=O, $C_{1-3}$ haloalkyl, or $C_{1-3}$ haloalkoxy;

$R^5$ is, independently at each occurrence, H, $C_{1-6}$ alkyl, $C_{0-3}$ alkyl-$C_{3-6}$ cycloalkyl, $C_{0-3}$ alkyl-phenyl;

$R^6$ is, independently at each occurrence, H, $C_{1-6}$ alkyl, $C_{0-3}$ alkyl-$C_{3-6}$ cycloalkyl, $C_{0-3}$ alkyl-phenyl;

$R^7$ is, independently at each occurrence, H, $C_{1-6}$ alkyl, $C_{0-3}$ alkyl-$C_{3-6}$ cycloalkyl, $C_{0-3}$ alkyl-phenyl;

$R^8$ is F, =O or $C_{1-3}$ alkyl, and n is 0, 1, or 2.

Another embodiment provides a compound of Formula (I), or stereoisomers, tautomers, isotopes, salts, pharmaceutically acceptable salts, solvates, or prodrugs thereof, wherein L is —C(O)NR$^e$—; and A is $A^1$ or -$A^1$-$L^1$ wherein $A^1$ is $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ deuteroalkyl, $C_{1-6}$ haloalkyl, $C_{0-3}$ alkyl-$C_{3-10}$ cycloalkyl-$C_{0-3}$-alkyl, $C_{0-3}$-alkyl-$C_{3-6}$ cycloalkyl-$C_{0-3}$-alkyl, $C_{0-3}$-alkyl-imidazolyl, $C_{0-3}$-alkyl-pyrrolidinyl, $C_{0-3}$-alkyl-tetrahydropyranyl, $C_{0-3}$-alkyl-pyridinyl, wherein the pyrrolidinyl is substituted with 0-2 $R^8$;

Another embodiment provides a compound of Formula (I), or stereoisomers, tautomers, isotopes, salts, pharmaceutically acceptable salts, solvates, or prodrugs thereof, wherein $R^a$ is H, Cl, F, or $C_{1-4}$ alkyl, $C_{1-4}$ alkoxy or $C_{1-4}$ deuteroalkoxy;

$R^b$ is H, $C_{1-3}$ alkyl, or $C_{1-3}$ alkoxy; and $R^c$ is H, or $C_{1-4}$ alkyl.

Another embodiment provides a compound of Formula (I), or stereoisomers, tautomers, isotopes, salts, pharmaceutically acceptable salts, solvates, or prodrugs thereof, wherein $A^1$ is $C_{1-6}$ alkyl substituted with 0-1 OH, $C_{1-6}$ deuteroalkyl substituted with 0-1 OH, and $C_{0-3}$ alkyl-$C_{3-6}$ cycloalkyl; and $L^1$ is —O—, —C(O)—, —C(O)NR$^e$—, and —SO$_2$NH—.

Another embodiment provides a compound of Formula (I), or stereoisomers, tautomers, isotopes, salts, pharmaceutically acceptable salts, solvates, or prodrugs thereof, wherein $R^a$ is H, $C_{1-4}$ alkyl, $C_{1-4}$ alkoxy or $C_{1-4}$ deuteroalkoxy;

$R^b$ is H, or $C_{1-3}$ alkyl; and $R^c$ is H.

Another embodiment provides a compound of Formula (I), or stereoisomers, tautomers, isotopes, salts, pharmaceutically acceptable salts, solvates, or prodrugs thereof, wherein $R^1$ is $C_{1-6}$ alkyl, $C_{1-6}$ haloalkyl, $C_{1-6}$ deuteroalkyl, $C_{0-3}$ alkyl-$C_{3-6}$ cycloalkyl, $C_{0-3}$ alkyl-piperidinyl, $C_{0-3}$ alkyl-pyrrolidinyl, $C_{0-3}$ alkyl-morpholinyl, $C_{0-3}$ alkyl-pyrrolidinyl, wherein the alkyl, cycloalkyl, piperidinyl, pyrrolidinyl, or morpholinyl are independently substituted with 0-2 of =O, halo, OH, $C_{1-3}$ alkyl, $C_{1-3}$ deuteroalkyl, or NR$^{1e}_2$.

Another embodiment provides a compound of Formula (I), or stereoisomers, tautomers, isotopes, salts, pharmaceutically acceptable salts, solvates, or prodrugs thereof, wherein $R^1$ is $C_{1-3}$ alkyl, $C_{1-3}$ deuteroalkyl, or $C_{0-1}$ alkyl-cyclopropyl;

$R^2$ is $C_{1-6}$ alkyl, phenyl, (CH$_2$)$_n$—$C_{3-6}$ cycloalkyl, or a (CH$_2$)$_n$-3 to 6 membered heterocycle, wherein the heterocycle is selected from morpholinyl, tetrahydro-2H-pyranyl, or pyrrolidinyl, wherein any of the phenyl or heterocycle groups are substituted with 0-3 $R^{2a}$; and $R^{2a}$ is F, Cl, CN, =O, $C_{1-6}$ alkyl, $C_{1-6}$ alkoxy, $C_{1-6}$ deuteroalkyl, $C_{1-3}$ deuteroalkoxy, $C_{1-2}$ haloalkyl, $C_{1-3}$ alkyl-$C_{3-6}$ cycloalkyl-$C_{0-3}$ alkyl, $C_{3-6}$ cycloalkoxy, $C_{3-6}$ cycloalkyl-$C_{1-3}$ alkoxy-, $C_{3-6}$ cycloalkyl-$C_{1-3}$ deuteroalkoxy-, $C_{3-6}$ cycloalkoxy-$C_{1-3}$ alkyl-, phenyl $C_{1-4}$ alkyl-SO$_2$—, $C_{3-6}$ cycloalkyl-SO$_2$—, NR$^6$R$^6$CO—, NR$^6$—(CH$_2$)$_n$—, R$^5$—C(O)—, R$^6$—OC(O)—NH—, R$^7$—NHC(O)—O—, R$^7$—SO$_2$—, R$^5$—SO$_2$NH—, —(CH$_2$)$_n$-piperizinyl, —(CH$_2$)$_n$-morpholinyl, wherein each alkyl, cycloalkyl, phenyl, or heterocycle is substituted with 0-3 $R^{2b}$.

Another embodiment provides a compound of Formula (I), or stereoisomers, tautomers, isotopes, salts, pharmaceutically acceptable salts, solvates, or prodrugs thereof, wherein L-A- is —

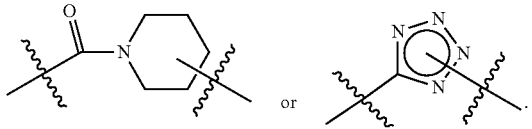

Another embodiment provides a compound of Formula (I), or stereoisomers, tautomers, isotopes, salts, pharmaceutically acceptable salts, solvates, or prodrugs thereof, wherein $R^a$ is H, Cl, F, or $C_{1-4}$ alkyl, $C_{1-4}$ alkoxy or $C_{1-4}$ deuteroalkoxy;

$R^b$ is H, $C_{1-3}$ alkyl, or $C_{1-3}$ alkoxy; and $R^c$ is H, or $C_{1-4}$ alkyl;

$R^1$ is $C_{1-6}$ alkyl, $C_{1-6}$ haloalkyl, $C_{1-6}$ deuteroalkyl, $C_{0-3}$ alkyl-$C_{3-6}$ cycloalkyl, $C_{0-3}$ alkyl-piperidinyl, $C_{0-3}$ alkyl-pyrrolidinyl, $C_{0-3}$ alkyl-morpholinyl, $C_{0-3}$ alkyl-pyrrolidinyl, wherein the alkyl, cycloalkyl, piperidinyl, pyrrolidinyl, or morpholinyl are independently substituted with 0-2 of =O, halo, OH, $C_{1-3}$ alkyl, $C_{1-3}$ deuteroalkyl, NR$^{1e}_2$;

$R^2$ is $C_{0-3}$alkyl-phenyl, $C_{0-3}$alkyl-$C_{3-6}$ cycloalkyl, or a $C_{0-3}$alkyl-3 to 6 membered heterocycle, wherein the heterocycle is selected from morpholinyl, tetrahydro-2H-pyranyl, or pyrrolidinyl, wherein any of the phenyl or heterocycle groups are substituted with 0-3 $R^{2a}$; and $R^{2a}$ is F, Cl, CN, =O, $C_{1-6}$ alkyl, $C_{1-6}$ alkoxy, $C_{1-6}$ deuteroalkyl, $C_{1-3}$ deuteroalkoxy, $C_{1-2}$ haloalkyl, $C_{1-3}$ alkyl-$C_{3-6}$ cycloalkyl-$C_{0-3}$ alkyl, $C_{3-6}$ cycloalkoxy, $C_{3-6}$ cycloalkyl-$C_{1-3}$ alkoxy-, $C_{3-6}$ cycloalkyl-$C_{1-3}$ deuteroalkoxy-, $C_{3-6}$ cycloalkoxy-$C_{1-3}$ alkyl-, phenyl $C_{1-4}$ alkyl-SO$_2$—, $C_{3-6}$ cycloalkyl-SO$_2$—, NR$^6$R$^6$CO—, NR$^6$—(CH$_2$)$_n$—, R$^5$—C(O)—, R$^6$—OC(O)—NH—, R$^7$—NHC(O)—O—, R$^7$—SO$_2$—, R$^5$—SO$_2$NH—, —(CH$_2$)$_n$-piperizinyl, —(CH$_2$)$_n$-morpholinyl, wherein each alkyl, cycloalkyl, phenyl, or heterocycle is substituted with 0-3 $R^{2b}$.

Another embodiment provides a compound of Formula (I), or stereoisomers, tautomers, isotopes, salts, pharmaceutically acceptable salts, solvates, or prodrugs thereof, wherein the compound is selected from the examples.

Another embodiment provides a compound of Formula (I), or stereoisomers, tautomers, isotopes, salts, pharmaceutically acceptable salts, solvates, or prodrugs thereof, wherein
  $R^1$ is $CH_2$-cyclopropyl, cyclopropyl, $CH_3$, $CD_3$, or $CD_2CD_3$.

Another embodiment provides a compound of Formula (I), or stereoisomers, tautomers, isotopes, salts, pharmaceutically acceptable salts, solvates, or prodrugs thereof, wherein
  L is —CONH—;
  A is $C_{1-6}$ alkyl substituted with 0-1 OH, $C_{1-6}$ deuteroalkyl substituted with 0-1 OH;
  $R^2$ is phenyl substituted with 0-3 $R^{2a}$.

Another embodiment provides a compound of Formula (I), or stereoisomers, tautomers, isotopes, salts, pharmaceutically acceptable salts, solvates, or prodrugs thereof, wherein
  $R^{2a}$ is F, $CH_3$, $OCH_3$, $CF_3$, or $OCF_3$.

Another embodiment provides a compound of Formula (I), or stereoisomers, tautomers, isotopes, salts, pharmaceutically acceptable salts, solvates, or prodrugs thereof, wherein
  L is —C(O)NH—;
  A is $A^1$, wherein $A^1$ is $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ deuteroalkyl, $C_{1-6}$ haloalkyl-, $C_{0-3}$ alkyl-$C_{3-10}$ cycloalkyl-$C_{0-3}$-alkyl-, $C_{0-3}$-alkyl-$C_{3-6}$ cycloalkyl-$C_{0-3}$-alkyl, —$C_{0-3}$-alkyl-imidazolyl-, —$C_{0-3}$-alkyl-pyrrolidinyl-, $C_{0-3}$-alkyl-tetrahydropyranyl-, —$C_{0-3}$-alkyl-pyridinyl-, wherein the pyrrolidinyl is substituted with 0-2 $R^8$ Another embodiment provides a compound of Formula (I), or stereoisomers, tautomers, isotopes, salts, pharmaceutically acceptable salts, solvates, or prodrugs thereof, wherein
  $R^{2a}$ is halo, CN, =O, $C_{1-6}$ alkyl, $C_{1-6}$ alkoxy, $C_{1-6}$ haloalkyl, $C_{1-6}$ haloalkoxy, $C_{3-6}$ cycloalkoxy, $C_{3-6}$ cycloalkyl-$C_{1-3}$ alkoxy-, phenyl-O—, $C_{1-4}$ alkyl-$SO_2$—, $C_{3-6}$ cycloalkyl-$SO_2$—, —C(O)—$R^5$, —NHC(O)—O—$R^7$, —$SO_2$—$R^7$, —$SO_2NH$—$R^5$, heterocycle-, heterocycle-O—, heterocycle-$CH_2$—, wherein the heterocycle is selected from tetrahdyro-2H-pyranyl, morpholinyl, piperidinyl, or piperazinyl, and wherein each alkyl, cycloalkyl, phenyl, or heterocycle is substituted with 0-3 $R^{2b}$;

Another embodiment provides a compound of Formula (I), or stereoisomers, tautomers, isotopes, salts, pharmaceutically acceptable salts, solvates, or prodrugs thereof, wherein
  L-A-$R^2$ is:

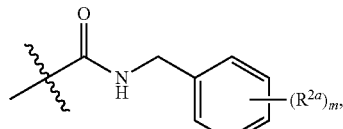

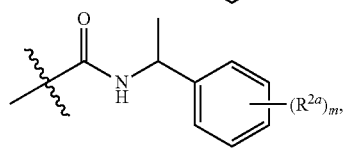

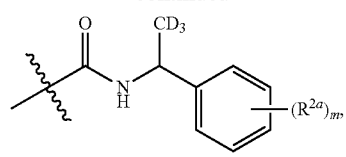

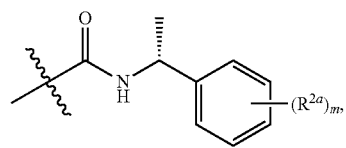

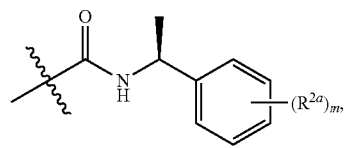

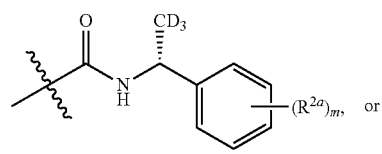

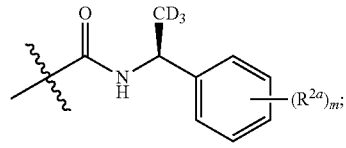

and m is 0, 1, 2 or 3.

Another embodiment provides a compound of Formula (I), or stereoisomers, tautomers, isotopes, salts, pharmaceutically acceptable salts, solvates, or prodrugs thereof, wherein
  L-A- is

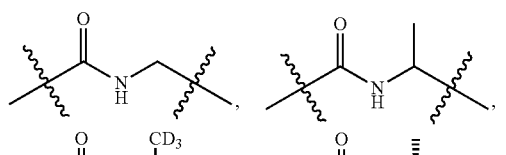

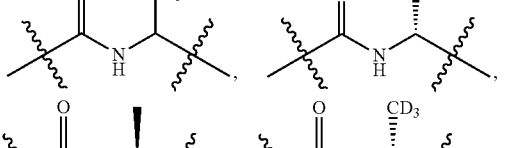

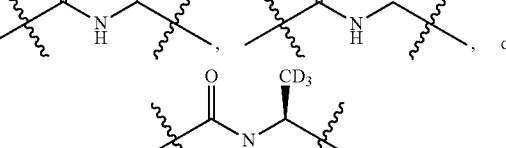

and R² is

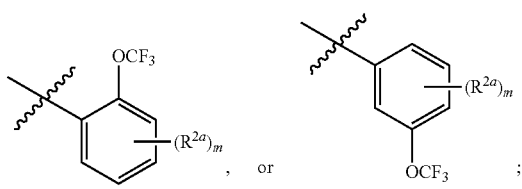

and m is 0, 1, or 2.

Another embodiment provides a compound of Formula (I), or stereoisomers, tautomers, isotopes, salts, pharmaceutically acceptable salts, solvates, or prodrugs thereof, wherein the compound is selected from the examples.

The present invention is also directed to pharmaceutical compositions useful in treating diseases associated with kinase modulation, including the modulation of receptor interacting protein kinases such as RIPK1, comprising compounds of formula (I), or pharmaceutically-acceptable salts thereof, and pharmaceutically-acceptable carriers or diluents.

The invention further relates to methods of treating diseases associated with kinase modulation, including the modulation of receptor interacting protein kinases such as RIPK1, comprising administering to a patient in need of such treatment a therapeutically-effective amount of a compound according to formula (I).

The present invention also provides processes and intermediates for making the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases and fibrotic diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease, comprising administering to a patient in need of such treatment a therapeutically-effective amount of a compound of formula (I), wherein the disease is inflammatory bowel disease, Crohn's disease or ulcerative colitis, poriasis, systemic lupus erythematosus (SLE), rheumatoid arthritis, multiple sclerosis (MS), transplant rejection, nonalcoholic steatohepatitis (NASH), or ischemia reperfusion.

The present invention also provides a method of treating a condition comprising administering to a patient in need of such treatment a therapeutically-effective amount of a compound of formula (I), wherein the condition is selected from systemic lupus erythematosus (SLE), multiple sclerosis (MS), transplant rejection, acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjogren's syndrome, peripheral neuropathies, pemphigus vulgaris, asthma, nonalcoholic steatohepatitis (NASH), or ischemia reperfusion.

The present invention also provides a method of treating a condition comprising administering to a patient in need of such treatment a therapeutically-effective amount of a compound of formula (I), wherein the condition is selected from macrophage necrosis in atheroscelerosis development, virus-induced inflammation, systemic inflammatory response syndrome and ethanol-induced liver injury, neurodegeneration such as detachment of the retina, retinal degeneration, wet and dry age-related macular degeneration (AMD), ischemia, amyotrophic lateral sclerosis (ALS), and Gaucher's disease.

The present invention also provides a method of treating a condition comprising administering to a patient in need of such treatment a therapeutically-effective amount of a compound of formula (I), wherein the condition is selected from inflammatory bowel disease, ulcerative colitis, Crohn's disease, psoriasis, rheumatoid arthritis (RA), heart failure, and nonalcoholic steatohepatitis (NASH).

The present invention also provides a method of treating a condition comprising administering to a patient in need of such treatment a therapeutically-effective amount of a compound of formula (I), wherein the condition is selected from inflammatory bowel disease, Crohn's disease, ulcerative colitis, and psoriasis.

The present invention also provides a method of treating a condition comprising administering to a patient in need of such treatment a therapeutically-effective amount of a compound of formula (I), wherein the condition is selected from nonalcoholic steatohepatitis (NASH), and ischemia reperfusion.

The present invention also provides a method for treating rheumatoid arthritis, comprising administering to a patient in need of such treatment a therapeutically-effective amount of a compound of formula (I), The present invention also provides a method of treating diseases, comprising administering to a patient in need of such treatment a therapeutically-effective amount of a compound of formula (I), or pharmaceutically acceptable salt thereof, in combination with other therapeutic agents.

The present invention also provides the compounds of the present invention or stereoisomers, tautomers, isotopes, salts, pharmaceutically acceptable salts, solvates, or prodrugs thereof, for use in therapy.

In another embodiment, compounds of formula (I), are selected from exemplified examples or combinations of exemplified examples or other embodiments herein.

The present invention also provides the use of the compounds of the present invention or stereoisomers, tautomers, isotopes, salts, pharmaceutically acceptable salts, solvates, or prodrugs thereof, for the manufacture of a medicament for the treatment of cancers, an allergic disease, an autoimmune disease or an inflammatory disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

The following are definitions of terms used in this specification and appended claims. The initial definition provided for a group or term herein applies to that group or term throughout the specification and claims, individually or as part of another group, unless otherwise indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula (I), (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "alkyl" or "alkylene" is intended to include both branched and straight-chain saturated aliphatic hydrocarbon groups having the specified number of carbon atoms. For example, "$C_{1-10}$ alkyl" (or alkyl ene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "carbocyclyl" or "carbocyclic" refers to a saturated or unsaturated, or partially unsaturated, monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Carbocycles, can include cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted. A preferred aryl group is optionally-substituted phenyl.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like, which optionally may be substituted at any available atoms of the ring(s).

The terms "heterocycloalkyl", "heterocyclo", "heterocycle", "heterocyclic", or "heterocyclyl" may be used interchangeably and refer to substituted and unsubstituted aromatic or non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like, including the exemplary groups listed under "heteroaryl". Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, and the like.

Exemplary tricyclic heteroaryl groups include carbazolyl, benzindolyl, phenanthrollinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents, as appropriate.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkyl" means a substituted alkyl having one or more halo substituents. For example, "haloalkyl" includes mono, bi, and trifluorom ethyl.

The term "haloalkoxy" means an alkoxy group having one or more halo substituents. For example, "haloalkoxy" includes OCF$_3$.

The term "deuteroalkyl" means a substituted alkyl having one or more deuterium atom. For example, the term "deuteroalkyl" includes mono, bi, and trideuteromethyl.

The term "heteroatoms" shall include oxygen, sulfur and nitrogen.

When the term "unsaturated" is used herein to refer to a ring or group, the ring or group may be fully unsaturated or partially unsaturated.

One skilled in the field will understand that, when the designation "$CO_2$" is used herein, this is intended to refer to the group

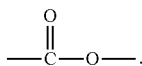

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwittertons (inner salts), e.g., when a compound of formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. In one embodiment, salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, PA, 1990, the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. As an example, an alkyl substituent is intended to cover alkyl groups have either hydrogen, deuterium, and/or some combination thereof. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All geometric isomers, tautomers, atropisomers, hydrates, solvates, polymorphs, and isotopically labeled forms of the compounds referred to herein, and mixtures thereof, are considered within the scope of the present invention. Methods of solvation are generally known in the art.

Utility

The compounds of the invention modulate kinase activity, including the modulation of RIPK1. Accordingly, compounds of formula (I) have utility in treating conditions associated with the modulation of kinase activity, and particularly the selective inhibition of RIPK1 activity. In another embodiment, compounds of formula (I) have advantageous selectivity for RIPK1 activity preferably from at least 20 fold to over 1,000 fold more selective over other kinases.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of RIPK1, compounds of Formula (I) are useful in treating RIPK1-associated conditions including, but not limited to, inflammatory diseases such as Crohn's disease and ulcerative colitis, inflammatory bowel disease, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, ALS, cerebral ischemias or neurodegenerative disease caused by traumatic injury, oncologic and viral diseases such as metastatic melanoma, Kaposi's sarcoma, multiple myeloma, and HIV infection and CMV retinitis, AIDS; fibrotic conditions such as, nonalcoholic steatohepatitis (NASH); and cardiac conditions such as, ischemia reperfusion; respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, ALS, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from inflammatory bowel disease, Crohn's disease and ulcerative colitis, allograft rejection, rheumatoid arthritis, psoriasis, ankylosing spondylitis, psoriatic arthritis, and pemphigus vulgaris, and nonalcoholic steatohepatitis (NASH), and ischemia reperfusion. Alternatively preferred methods of treatment are those wherein the condition is selected from ischemia reperfusion injury, including cerebral ischemia reperfusions injury arising from stroke and cardiac ischemia reperfusion injury arising from myocardial infarction.

When the terms "RIPK1-associated condition" or "RIPK1-associated disease or disorder" are used herein, each is intended to encompass all of the conditions identified above as if repeated at length, as well as any other condition that is affected by RIPK1 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit RIPK1.

The methods of treating RIPK1 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit RIPK1 and/or treat diseases associated with RIPK1.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; anti-inflammatory anti-bodies such as vedolizumab and ustekinumab, anti-inflammatory kinase inhibitors such as TYK2 inhibitors, antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, rapamycin (sirolimus or Rapamune) or derivatives thereof, and agonists of FGF21.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating RIPK1 kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals.

Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art.

Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methyl cellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of RIPK1 enzyme levels.

MLKL Phosphorylation High-Content Assay

HT29-L23 human colorectal adenocarcinoma cells were maintained in RPMI 1640 medium containing 10% heat-inactivated FBS, 1% Penicillin-Streptomycin and 10 mM HEPES. Cells were seeded at 2,000 cells/well in 384 well tissue culture-treated microplates (Greiner #781090-3B) and incubated at 37° C. (5% $CO_2$/95% $O_2$) for 2 d. On the day of the assay, the cells were treated with test compounds at final concentrations of 6.25 to 0.106 μM for 30 min at 37° C. (5% $CO_2$/95% $O_2$). Necroptopsis was induced using a mixture of human TNFα (35 ng/mL) (Peprotech #300-01A), SMAC mimetic (from US 2015/0322111 A1) (700 nM) and Z-VAD (140 nM) (BD pharmingen #51-6936). Following 6 h incubation at 37° C. (5% $CO_2$/95% $O_2$), the cells were fixed with 4% formaldehyde (ACROS 11969-0010) for 15 min at rt, then permeabilized with phosphate buffered saline (PBS) containing 0.2% Triton-X-100 for 10 min. MLKL phosphorylation was detected using anti-MLKL (phospho S358) antibody (Abeam #ab 187091) (1:1000 dilution in Blocking Buffer [PBS supplemented with 0.1% BSA]) with ON incubation at 4° C. After washing three times in PBS, goat anti-rabbit Alexa-488 (1:1000 dilution) (Life Technologies, A11008) and Hoechst 33342 (Life Technologies, H3570) (1:2000 dilution) in Blocking Buffer were added for 1 h at rt.

Following another three cycles of washes in PBS, the microplates were sealed, and cellular images were acquired in the Cellomics ArrayScan VTI high-content imager equipped with an X1 camera. Fluorescent images were taken using a 10× objective and the 386-23 BGRFRN_BGRFRN and 485-20 BGRFRN_BGRFRN filter sets, for nuclei and MLKL phosphorylation, respectively. The image sets were analyzed using the Compartmental Analysis Bioapplication software (Cellomics). The level of MLKL phosphorylation was quantified as MEAN_CircRingAvgIntenRatio. The maximal inhibitory response was defined by the activity induced by Neels (CAS #: 852391-15-2, 6.25 μM). The IC50 value was defined as the concentration of compound that produces 50% of the maximal inhibition. The data were fitted using the 4-parameter logistic equation to calculate the IC50 and Ymax values.

RIPK1 HTRF Binding Assay

A solution was prepared containing 0.2 nM Anti GST-Tb (Cisbio, 61GSTTLB), 90.6 nM probe and 1 nM His-GST-TVMV-hRIPK1 (1-324) in FRET Buffer (20 mM HEPES, 10 mM MgCl2, 0.015% Brij-35, 4 mM DTT, 0.05 mg/mL BSA). Using Formulatrix Tempest, the detection antibody/enzyme/probe solution (2 mL) was dispensed into wells of a 1536 plate (Black Low Binding Polystyrene 1536 Plate (Corning, 3724)) containing 10 nL of compounds of interest at appropriate concentration in DMSO. The plate was incubated at rt for 1 h. FRET was measured using the EnVision plate reader (Excitation: 340 nM, Emission: 520 nM/495 nM). Total signal (0% inhibition) was calculated from wells containing 10 nL DMSO only. Blank signal (100% inhibition) calculated from wells containing 10 nL of 15 nM staurosporine and internal controls.

Cloning and Baculovirus Expression of RIPK1 Construct

The coding region of human RIPK1(1-324) flanked by NdeI site at 5' end and stop codon TGA and XhoI site at 3' end was codon optimized and gene synthesized at GenScript USA Inc. (Piscataway, NJ) and subcloned into a modified pFastBac1 vector (Invitrogen, Carlsbad, CA) with N-terminal His-GST-TVMV tag, to generate His-GST-TVMV-hRIPK1(1-324)-pFB. The fidelity of the synthetic fragment was confirmed by sequencing.

Baculovirus was generated for the construct using the Bac-to-Bac baculovirus expression system (Invitrogen) according to the manufacturer's protocol. Briefly, recombinant bacmid was isolated from transformed DH10Bac E. coli competent cells (Invitrogen) and used to transfect Spodoptera frugiperda (Sf9) insect cells (Invitrogen). Baculovirus was harvested 72 hours post transfection and a virus stock was prepared by infecting fresh Sf9 cells at a 1/1000 (v/v) ratio for 66 hours.

For large scale protein production, Sf9 cells (Expression System, Davis, CA) grown in ESF921 insect medium (Expression System) at 2×106 cells/ml were infected with virus stock at a 1/100 (v/v) ratio for 66 hours. The production was carried out either at a 10 L scale in a 22 L cellbag (GE Healthcare Bioscience, Pittsburgh, PA) or at a 20 L scale in a 50 L cellbag using WAVE-Bioreactor System 20/50 (GE Healthcare Bioscience). The infected cells were harvested by centrifugation at 2000 rpm for 20 min at 4° C. in a SORVALL® RC12BP centrifuge. The cell pellets was stored at −70° C. before protein was purified.

Purification of his-GST-TVMV-hRIPK1(1-324) RIPK1 containing cell paste was resuspended in 50 mM Tris pH 7.5, 150 mM NaCl, 10 mM imidazole, 5% glycerol, 5 mM MgSO$_4$, 1 mM TCEP, 25 U/ml Benzonase, and Complete Protease Inhibitor tablets (1/50 ml, Roche Diagnostics, Indianapolis, IN). The cells were lysed by nitrogen cavitation using an unstirred pressure vessel @ 525 PSI (Parr Instrument Company, Moline, IL). The suspension was clarified by centrifugation at 136,000×g for 40 min, at 4° C. The lysate was decanted from the pellet and passed through a 5 ml NiNTA Superflow cartridge (Qiagen, Valencia, CA) using an AKTA Pure (GE Healthcare). Column was eluted with 10 CV linear gradient into 50 mM Tris 7.5, 150 mM NaCl, 500 mM imidazole, 5% glycerol, 1 mM TCEP. Peak fractions were pooled and loaded directly onto 5 ml GSTrap 4B column (GE Healthcare). Column was washed with 50 mM Tris 7.0, 150 mM NaCl, 5% glycerol, 1 mM DTT and eluted in 10 CV linear gradient into 50 mM Tris 8.0, 150 mM NaCl, 20 mM reduced glutathione, 5% glycerol, 1 mM DTT. Fractions identified by SDS-PAGE as containing RIPK1 were pooled and concentrated using 30 kDa MWCO spin concentrators (Amicon Ultra-15, Millipore, Billerica, MA) and loaded onto a HiLoad 26/600 Superdex 200 column (GE Healthcare) equilibrated in 25 mM Tris 7.5, 150 mM NaCl, 2 mM TCEP, 5% glycerol. The RIPK1 protein eluted as a dimer off the SEC column.

The yield was ~8 mg/L with a purity >95% as determined by Coomassie stain SDS-PAGE gel analysis. LCMS analysis of the protein showed that the protein had lost the N-terminal methionine, had one phosphorylated site, and was partially acetylated. Protein was aliquoted and stored at −80° C.

Using these assays, the $IC_{50}$ values of the following compounds were determined. See Table A.

TABLE A

| Ex | RIPK1 HTRF (IC50, nM) | pMLKL (IC50, nM) |
|---|---|---|
| 1 | 17 | 6.1 |
| 2 | 5.5 | 3.5 |
| 3 | 46 | 41 |
| 4 | 11 | 19 |
| 5 | 6.5 | 9.0 |
| 6 | 4.2 | 23 |
| 7 | 8.5 | 4.6 |
| 8 | 28 | 9.8 |
| 9 | 7.4 | 22 |
| 10 | 3.7 | 6.4 |
| 11 | 5.7 | 223 |
| 12 | 42 | 400 |
| 13 | 5.5 | 5.1 |
| 14 | 8.0 | 37 |
| 15 | 5.0 | 3.4 |
| 16 | 2.2 | 8.6 |
| 17 | 21 | 19 |
| 18-1 | 5.5 | 7.3 |
| 18-2 | 100 | 310 |
| 19-1 | 42 | 14 |
| 19-2 | 100 | 64 |
| 20 | 66 | 27 |
| 21-1 | 3.5 | 8.3 |
| 21-2 | 5.9 | 13 |
| 21-3 | 22 | 8.1 |
| 21-4 | 2.0 | 2.0 |
| 22 | 100 | 440 |
| 23 | 24 | 140 |
| 24 | 5.4 | 11 |
| 25 | 23 | 190 |
| 26 | 82 | 90 |
| 27 | 2.5 | 8.0 |
| 28 | 17 | 37 |
| 29 | 32 | 76 |
| 30 | 19 | 48 |
| 31 | 2.3 | 13 |
| 32 | 79 | 19 |
| 33 | 8.9 | 25 |
| 34 | 57 | 92 |
| 35 | 10 | 44 |
| 36 | 9.3 | 20 |
| 37 | 1.7 | 0.30 |
| 38 | NA | 13 |
| 39 | NA | 8.0 |
| 40 | NA | 5.7 |
| 41 | NA | 0.6 |
| 42 | NA | 88 |
| 43 | NA | 99 |
| 44 | 30 | 29 |
| 45 | NA | 5.0 |
| 46 | NA | 4.4 |
| 47 | NA | 38 |
| 48 | NA | 176 |
| 49 | NA | 21 |
| 50 | 2.4 | 7.0 |
| 51 | 0.7 | 0.9 |
| 52 | 1.8 | 10 |
| 53 | 2.6 | 10 |

TABLE A-continued

| Ex | RIPK1 HTRF (IC50, nM) | pMLKL (IC50, nM) |
|---|---|---|
| 54 | 28 | 120 |
| 55 | 12 | 27 |
| 56 | 8.4 | 26 |
| 57 | 3.4 | 110 |
| 58 | 14 | 5.6 |
| 59 | 2.9 | 1.1 |
| 60 | 48 | 16 |
| 61 | 21 | 28 |
| 62 | 6.8 | 26 |
| 63 | 2.3 | 16 |
| 64 | 8.1 | 3.0 |
| 65 | 8.3 | 1.6 |
| 66 | 5.0 | 350 |
| 67 | 4.7 | 39 |
| 68 | 4.6 | 28 |
| 69 | 4.5 | 26 |
| 70 | 21 | 36 |
| 71 | 80 | 77 |
| 72 | 390 | 400 |
| 73 | 4.7 | 120 |
| 74 | 28 | 62 |
| 75 | 1.8 | 4.4 |
| 76 | 98 | 100 |
| 77 | 3.8 | 78 |
| 78 | 2.7 | 11 |
| 79 | 1.8 | 21 |
| 80 | 1.4 | 20 |
| 81 | 3.1 | 22 |
| 82 | 0.4 | 41 |
| 83 | 7.6 | 47 |
| 84 | 45 | 180 |
| 85 | 3.7 | 72 |
| 86 | 2.4 | 4.1 |
| 87 | 3.9 | 13 |
| 88 | 52 | 250 |
| 89 | 7.7 | 85 |
| 90 | 16 | 47 |
| 91 | 1.8 | 16 |
| 92 | 2.8 | 12 |
| 93 | 1.3 | 8.3 |
| 94 | 9.9 | 96 |
| 95 | 17 | 9.3 |
| 96 | 34 | 4.6 |
| 97 | 8.5 | 12 |
| 98 | 26 | 46 |
| 99 | 11 | 14 |
| 100 | 18 | 63 |
| 101 | 4.5 | 19 |
| 102 | 21 | 73 |
| 103 | 70 | 40 |
| 104 | 40 | 93 |
| 105 | 54 | 180 |
| 106 | 9.8 | 29 |
| 107 | 53 | 72 |
| 108 | 11 | 110 |
| 109 | 5.9 | 15 |
| 110 | 6.3 | 7.3 |
| 111 | 7.0 | 20 |
| 112 | 4.8 | 7.6 |
| 113 | 27 | 9.7 |
| 114 | 38 | 200 |
| 115 | 0.040 | 100 |
| 116 | 9.6 | 54 |
| 117 | 2.6 | 11 |
| 118 | 6.2 | 2.6 |
| 119 | 33 | 110 |
| 120 | 11 | 100 |
| 121 | 6.1 | 7.5 |
| 122 | 12 | 120 |
| 123 | 21 | 75 |
| 124 | 26 | 83 |
| 125 | 12 | 8.8 |
| 126 | 4.2 | 6.9 |
| 127 | 2.3 | 3.7 |
| 128 | 2.3 | 3.1 |
| 129 | 6.8 | 9.0 |
| 130 | 1.9 | 3.9 |
| 131 | 10 | 2.3 |
| 132 | 35 | 140 |
| 133 | 12 | 57 |
| 134 | 17 | 7.3 |
| 135 | 89 | 200 |
| 136 | 19 | 480 |
| 137 | 1.6 | 2.9 |
| 138 | 12 | 89 |
| 139 | 13 | 28 |
| 140 | 6.9 | 18 |
| 141 | 25 | 41 |
| 142 | 53 | 120 |
| 143 | 28 | 26 |
| 144 | 46 | 100 |
| 145 | 9.6 | 200 |
| 146 | 69 | 400 |
| 147 | 31 | 110 |
| 148 | 54 | 96 |
| 149 | 33 | 74 |
| 150 | 32 | 110 |
| 151 | 9.8 | 24 |
| 152 | 20 | 3.3 |
| 153 | 2.9 | 6.3 |
| 154 | 2.9 | 58 |
| 155 | 13 | 22 |
| 156 | 3.7 | 7.9 |
| 157 | 2.1 | 6.8 |
| 158 | 35 | 21 |
| 159 | 34 | 110 |
| 160 | 27 | 120 |
| 161 | 25 | 74 |
| 162 | 43 | 74 |
| 163 | 47 | 180 |
| 164 | 5.4 | 3.7 |
| 165 | 140 | 15 |
| 166 | 83 | 34 |
| 167 | 12 | 12 |
| 168 | 38 | 17 |
| 169 | 22 | 31 |
| 170 | 7.9 | 23 |
| 171 | 71 | 120 |
| 172 | 14 | 28 |
| 173 | 5.7 | 66 |
| 174 | 6.4 | 14 |
| 175 | 9.9 | 29 |
| 176 | 10 | 16 |
| 177 | 2.9 | 15 |
| 178 | 38 | 120 |
| 179 | 37 | 73 |
| 180 | 19 | 39 |
| 181 | 27 | 82 |
| 182 | 12 | 83 |
| 183 | 5.9 | 15 |
| 184 | 7.0 | 88 |
| 185 | 13 | 110 |
| 186 | 95 | 13 |
| 187 | 28 | 78 |
| 188 | 23 | 130 |
| 189 | 9.6 | 30 |
| 190 | 100 | 290 |
| 191 | 120 | 89 |
| 192 | 110 | 430 |
| 193 | 260 | 480 |
| 194 | 67 | 52 |
| 195 | 36 | 39 |
| 196 | 84 | 19 |
| 197 | 52 | 52 |
| 198 | 6.5 | 23 |
| 199 | 340 | 99 |
| 200 | 130 | 79 |
| 201 | 11 | 110 |
| 202 | 36 | 53 |
| 203 | 12 | 95 |
| 204 | 12 | 84 |
| 205 | 20 | 60 |
| 206 | 220 | 3.8 |
| 207 | 53 | 110 |

TABLE A-continued

| Ex | RIPK1 HTRF (IC50, nM) | pMLKL (IC50, nM) |
|---|---|---|
| 208 | 27 | 18 |
| 209 | 33 | 74 |
| 210 | 450 | 88 |
| 211 | 25 | 27 |
| 212 | 15 | 28 |
| 213 | 13 | 21 |
| 214 | 9.8 | 36 |
| 215 | 3.9 | 16 |
| 216 | 37 | 30 |
| 217 | 8.8 | 13 |
| 218 | 45 | 32 |
| 219 | 12 | 18 |
| 220 | 30 | 100 |
| 221 | 36 | 92 |
| 222 | 5.7 | 14 |
| 223 | 14 | 28 |
| 224 | 17 | 12 |
| 225 | 43 | 91 |
| 226 | 57 | 41 |
| 227 | 11 | 69 |
| 228 | 58 | 51 |
| 229 | 210 | 82 |
| 230 | 11 | 55 |
| 231 | 48 | 10 |
| 232 | 33 | 26 |
| 233 | 54 | 77 |
| 234 | 8.7 | 20 |
| 235 | 34 | 48 |
| 236 | 37 | 40 |
| 237 | 6.3 | 14 |
| 238 | 47 | 41 |

Methods of Preparation

Compounds of Formula (I), and intermediates used in the preparation of compounds of Formula (I), can be prepared using procedures shown in the following examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations as used herein, are defined as follows: "1×" for once, "2×" for twice, "3×" for thrice, "aq" or "aq." for aqueous, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "ON" for overnight, "RT" for retention time, "atm" for atmosphere, "psi" for pounds per square inch, "conc." for concentrate, "sat" or "saturated" for saturated, "CVs" for column volumes, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" or "LC/MS" for liquid chromatography mass spectrometry, "HPLC" for high pressure liquid chromatography, "RP HPLC" for reverse phase HPLC, "TLC" or "tlc" for thin layer chromatography, "SFC" for supercritical fluid chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "MHz" for megahertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
i-Bu tert-butyl
Ph phenyl
Bn benzyl
Boc tert-butyloxycarbonyl
AcOH or HOAc acetic acid
$Ac_2O$ acetic anhydride
Boc (tert-butoxy)carbonyl
BOP benzotriazol-1-yloxytris(dimethyl amino)phosphonium hexafluorophosphate
CBz carbobenzyloxy
$CH_2Cl_2$ dichloromethane
$CH_3CN$ or ACN acetonitrile
$CDCl_3$ deutero-chloroform
$CHCl_3$ chloroform
$Cs_2CO_3$ cesium carbonate
DCE 1,2 dichloroethane
DCM dichloromethane
DIEA/DIPEA/Hünig's Base diisopropylethylamine
DMAP 4-dimethylaminopyridine
DME 1,2-dimethoxyethane
DMF dimethyl formamide
DMSO dimethyl sulfoxide
$Et_3N$ or TEA triethylamine
EtOAc ethyl acetate
$Et_2O$ diethyl ether
EtOH ethanol
HCl hydrochloric acid
Hex hexane
$K_2CO_3$ potassium carbonate
KOAc potassium acetate
$K_3PO_4$ potassium phosphate
LiOH lithium hydroxide
MeOH methanol
MeI iodomethane
$MgSO_4$ magnesium sulfate
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4Cl$ ammonium chloride
$NH_4OH$ ammonium hydroxide
Pd/C palladium on carbon
$PdCl_2$(dppf) [1,1'-bis(diphenylphosphino)-ferrocene]dichloropalladium(II)
PG protecting group
i-PrOH or IPA isopropanol
$SiO_2$ silica oxide
TBAI tetra-n-butylammonium iodide
TFA trifluoroacetic acid
THF tetrahydrofuran The compounds of the present invention may be synthesized by many methods available to those skilled in the art of organic chemistry (Maffrand, J. P. et al., Heterocycles, 16(1):35-7 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures.

Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Scheme 1 illustrates an approach to the synthesis of compounds exemplified by 6. Amide formation of starting material 1 can be achieved through BOP coupling reaction to yield 2. Other coupling reagents known to those in the art, including mixed anhydrides or carboxylic acid chlorides, could also be used for the transformation. Protection of 2 can be accomplished using $BOC_2O$ in conjunction with base to yield 3. A Suzuki coupling reaction (Miyaura, N. and Suzuki, A. Chemical Reviews, 95:2457-2483, 1995) of 3 and 7 can provide compound 4. Should 4 be an ester instead of a carboxylic acid, a hydrolysis step following the Suzuki reaction could be performed. Suitable bases may include lithium hydroxide monohydrate, sodium hydroxide or other known to those in the art. Compounds exemplified by 6 can be formed by an amide coupling mediated by BOP reagent as shown in the scheme or an alternative amide coupling reagent. Use of an anhydride or carboxylic acid chloride may also effect this transformation.

Scheme 1

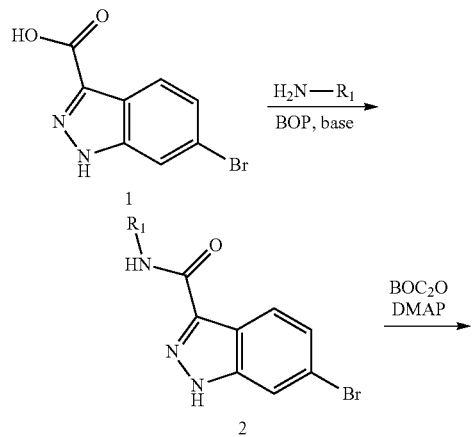

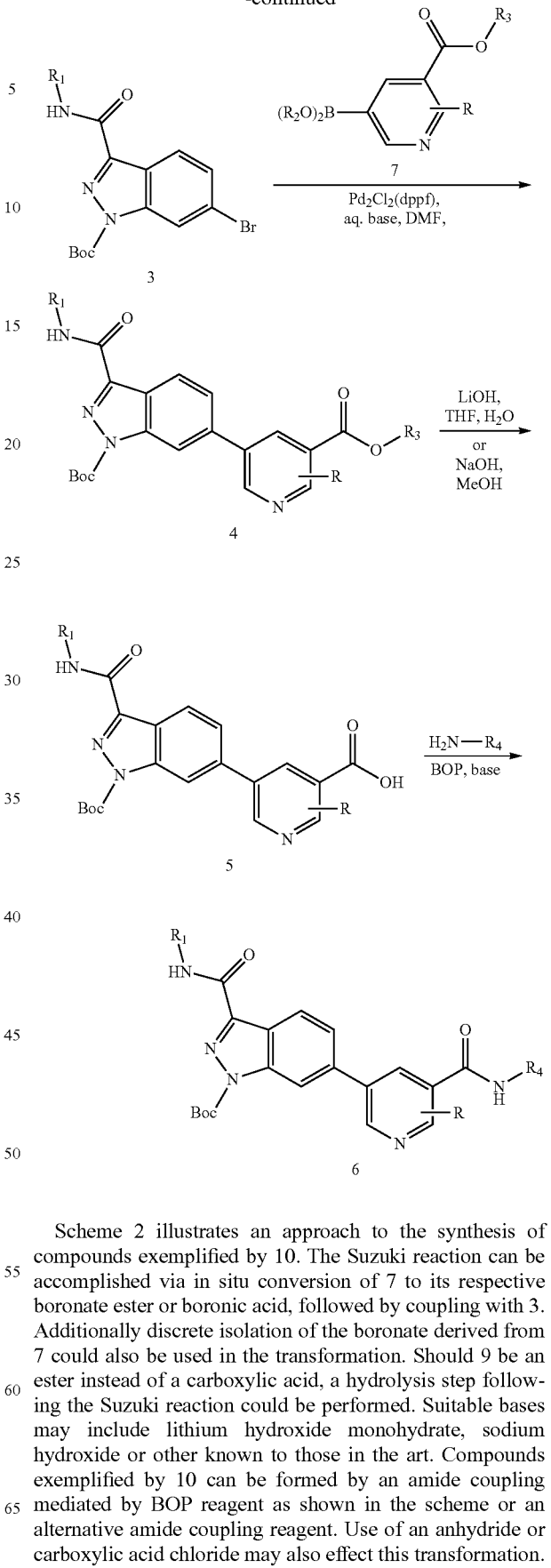

Scheme 2 illustrates an approach to the synthesis of compounds exemplified by 10. The Suzuki reaction can be accomplished via in situ conversion of 7 to its respective boronate ester or boronic acid, followed by coupling with 3. Additionally discrete isolation of the boronate derived from 7 could also be used in the transformation. Should 9 be an ester instead of a carboxylic acid, a hydrolysis step following the Suzuki reaction could be performed. Suitable bases may include lithium hydroxide monohydrate, sodium hydroxide or other known to those in the art. Compounds exemplified by 10 can be formed by an amide coupling mediated by BOP reagent as shown in the scheme or an alternative amide coupling reagent. Use of an anhydride or carboxylic acid chloride may also effect this transformation.

Scheme 2

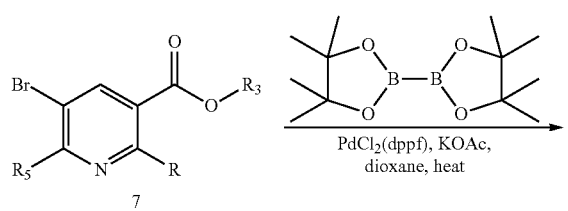

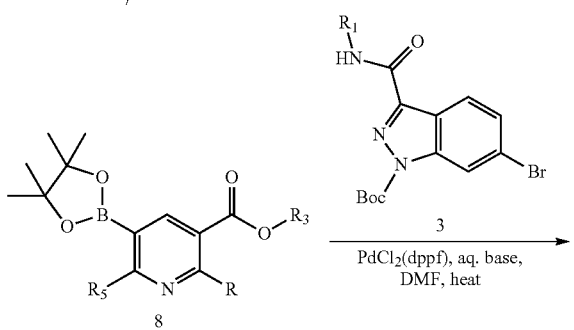

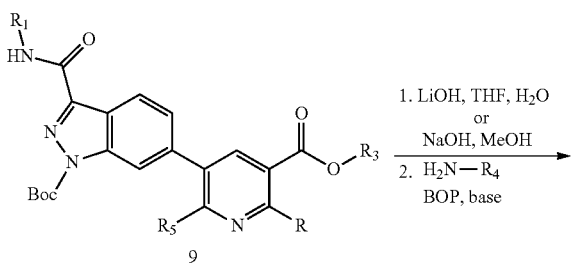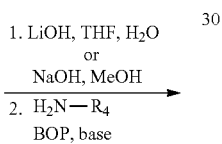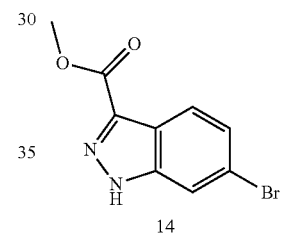

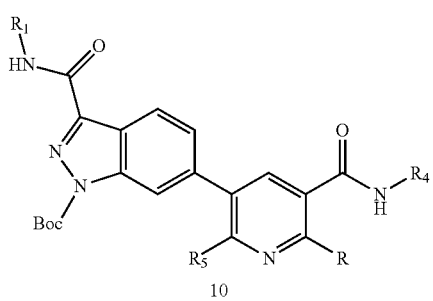

Scheme 3

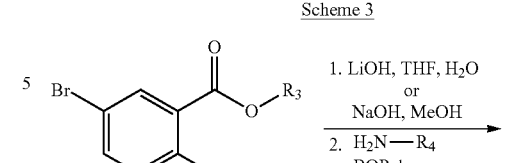

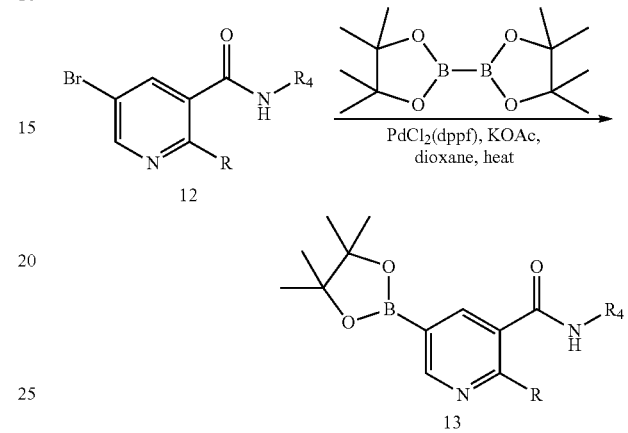

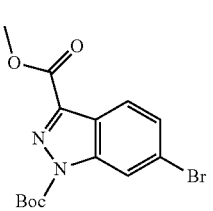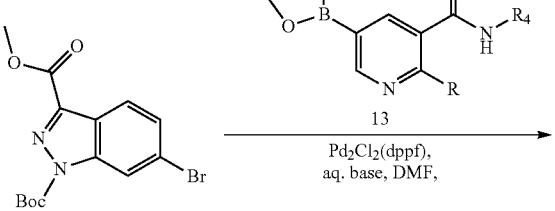

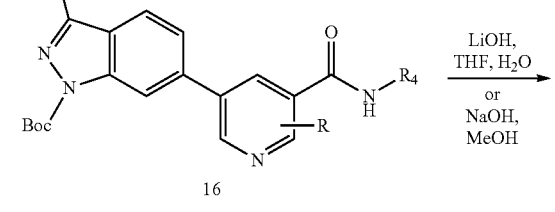

Scheme 3 highlights another route available to access compounds exemplified by 18. Nicotinate derivatives such as 11 can undergo hydrolysis with lithium hydroxide monohydrate or sodium hydroxide to yield a nicotinic acid derivative. In addition to amide coupling under a variety of conditions, 12 can also be accessed via coupling of the anhydride or acid chloride. Conversion of 12 to the corresponding boronate ester 13 can proceed under anhydrous Suzuki conditions. 13 can be isolated discreetly or used in situ in the subsequent Suzuki reaction with 15 to yield compound 16. As in previous examples, compound 16 can be hydrolyzed to compounds such as 17. Compounds exemplified by 18 can be formed by an amide coupling mediated by BOP reagent as shown in the scheme or an alternative amide coupling reagent.

-continued

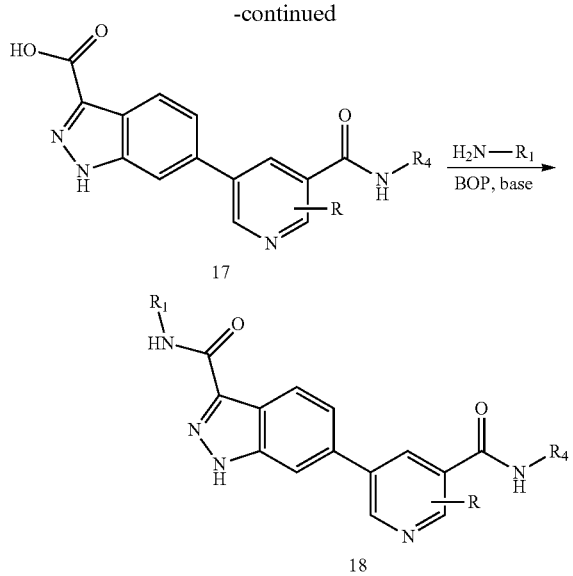

As shown in Scheme 3, compound 2 can be converted to 19 under Suzuki conditions with 20. An alkylation reaction with alkyl bromide under base conditions can provide compounds exemplified by 21.

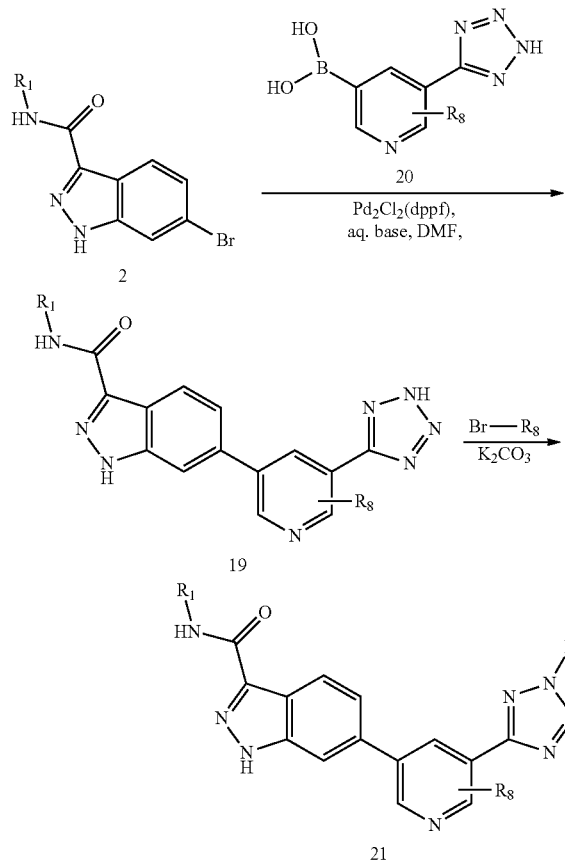

Purification of intermediates and final products was carried out via either normal or reverse phase chromatography. Normal phase chromatography on an ISCO system was carried out using prepacked $SiO_2$ cartridges eluting with either gradients of hexanes and ethyl acetate or dichloromethane and methanol unless otherwise indicated. Reverse phase preparative HPLC or LCMS was carried out using C18 columns eluting with gradients of Solvent A (90% water, 10% methanol, 0.1% TFA) and Solvent B (10% water, 90% methanol, 0.1% TFA, UV 220 nm), or with gradients of Solvent A (95% water, 5% acetonitrile, 0.1% TFA) and Solvent B (5% water, 95% acetonitrile, 0.1% TFA, UV 220 nm), or with gradients of Solvent A (98% water, 2% acetonitrile, 0.05% TFA) and Solvent B (98% acetonitrile, 2% water, 0.05% TFA, UV 254 nm), or with gradients of Solvent A (95% water, 5% acetonitrile with 10 mM ammonium acetate) and Solvent B (95% acetonitrile, 5% water with 10 mM ammonium acetate).

In the majority of examples, two analytical LCMS injections were used to determine final purity.

Method A: Column: Waters Acquity UPLC BEH C18, 2.1×50 mm, 1.7 µM particles; Mobile phase A: 5:95 acetonitrile:water with 10 mM ammonium acetate; Mobile phase B: 95:5 acetonitrile:water with 10 mM ammonium acetate; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 µm particles; Mobile phase A: 5:95 acetonitrile:water with 0.1% TFA; Mobile phase B: 95:5 acetonitrile:water with 0.1% TFA; Temperature: 50° C.; Gradient: 0-100% B over 3 min, then a 0.75 min hold at 100% B; Flow: 1.11 mL/min; Detection: UV at 220 nm. In a minority of examples analytical HPLC injections were used to determine final purity.

Method C: Column: Sunfire C18, 3.0×150 mm, 3.5 µM particles; Mobile phase A: 5:95 acetonitrile:water with 0.1% TFA; Mobile phase B: 95:5 acetonitrile:water with 0.1% TFA; Gradient: 0-100% B over 10 minutes; Flow: 1 mL/min; Detection: UV at 220 and 254 nm Method D: Column: Xbridge Phenyl, 3.0×150 mm, 3.5 µM particles; Mobile phase A: 5:95 acetonitrile:water with 0.1% TFA; Mobile phase B: 95:5 acetonitrile:water with 0.1% TFA; Gradient: 0-100% B over 10 minutes; Flow: 1 mL/min; Detection: UV at 220 and 254 nm Method E: Column: XBridge C18, 3.0×150 mm, 3.5 µM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

Method F: Column: XBridge Phenyl, 3.0×150 mm, 3.5 µM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

A majority of mass spectra runs were: LCMS (ESI) m/z: $[M+H]^+$ BEH C18, 2.11×50 mm, 1.7 µm; Mobile phase A: 2:98 water:acetonitrile with 0.1% TFA; Mobile phase B: 98:2 acetonitrile:water with 0.1% TFA; Gradient: 0-100% B over 2 minutes; Flow: 0.8 mL/min; Detection: UV at 220 nm.

NMR spectra were run with water suppression, unless otherwise noted. When water suppression affected characterization of the compounds by NMR, it is noted in the text.

Example 1 N-[(1,1,2,2,2-deuteroethyl]-6-(5-{[(1S)-1-[2-fluoro-5-(trifluoromethoxy)phenyl](2,2,2-deutero)ethyl]carbamoyl}-6-(deutero)methoxypyridin-3-yl)-1H-indazole-3-carboxamide

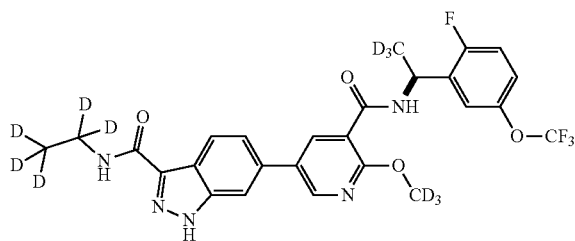

1A: (S,E)-N-(2-fluoro-5-(trifluoromethoxy)benzylidene)-2-methylpropane-2-sulfinamide: Titanium(IV) isopropoxide (5.69 mL, 19.22 mmol) was added to a THF (20 mL) solution of 2-fluoro-5-(trifluoromethoxy)benzaldehyde (2.0 g, 9.61 mmol) and (S)-(−)-2-methyl-2-propoansulfinamide (1.165 g, 9.61 mmol) at rt and stirred for 72 h. The reaction was quenched by adding brine (10 mL) and hexanes (10 mL) at 0° C. The mixture was filtered through a pad of Celite and the pad was rinsed with ethyl acetate (2×10 mL). The combined organic solutions were dried over sodium sulfate, filtered and concentrated under reduced pressure to give crude product which was purified on a silica gel column with Hexanes/EtOAc (100/0 to 50/50) to give (S,E)-N-(2-fluoro-5-(trifluoromethoxy) benzylidene)-2-methylpropane-2-sulfinamide (2.83 g, 8.73 mmol, 91% yield).

MS ESI m/z 312.0 (M+H)

$^1$H NMR (400 MHz, CD$_3$OD) δ 8.83 (s, 1H), 7.90 (dd, J=4.7, 3.4 Hz, 1H), 7.64-7.53 (m, 1H), 7.48-7.35 (m, 1H), 1.30 (s, 9H).

1B: (S)—N—((R)-1-(2-fluoro-5-(trifluoromethoxy)phenyl)ethyl-2,2,2-d3)-2-methylpropane-2-sulfinamide (a) and (S)—N—((S)-1-(2-fluoro-5-(trifluoromethoxy)phenyl) ethyl-2,2,2-d3)-2-methylpropane-2-sulfinamide (b): To a solution of (S,E)-N-(2-fluoro-5-(trifluoromethoxy)benzylidene)-2-methylpropane-2-sulfinamide (2.827 g, 9.08 mmol) in THF (40 mL) was added methyl-d$_3$-magnesium iodide (1 M in Et$_2$O) (13.62 mL, 13.62 mmol) dropwise at −40° C. which was maintained for 6 h, then warmed to 23° C. for 12 h. The reaction mixture was concentrated to a volume of 10 mL and quenched with saturated NH$_4$Cl solution (50 mL) at 0° C. The aqueous layer was extracted with EtOAc (50 mL×3). The combined organic phases were washed with brine (50 mL) and dried over Na$_2$SO$_4$. Filtration and concentration yielded (S)—N—((R.S)-1-(2-fluoro-5-(trifluoromethoxy)phenyl)ethyl-2,2,2-d3)-2-methylpropane-2-sulfinamide (3.2 g, 9.12 mmol, 100% yield). (S)—N—((R.S)-1-(2-Fluoro-5-(trifluoromethoxy)phenyl)ethyl-2,2,2-d$_3$)-2-methylpropane-2-sulfinamide (3.2 g, 9.12 mmol) was separated via preparative SFC with the following conditions: Preparative Column: (R,R)Whelk-O1 (5×50 cm, 10 µm), BPR pressure: 100 bars, Temperature: 49° C., Flow rate: 320 mL/min, Mobile Phase: CO$_2$/IPA:heptane [60:40 (v/v)] (85/15), Detector Wavelength: 215 nm. Fractions from peak 1 were combined to yield (S)—N—((R)-1-(2-fluoro-5-(trifluoromethoxy)phenyl)ethyl-2,2,2-d$_3$)-2-methylpropane-2-sulfinamide (1.61 g, 4.84 mmol, 50% yield, chiral purity: 99.9%).

MS ESI m/z 331.0 (M+H).

Fractions from peak 2 were combined to yield (S)—N—((S)-1-(2-fluoro-5-(trifluoromethoxy)phenyl)ethyl-2,2,2-d3)-2-methylpropane-2-sulfinamide (0.97 g, 2.87 mmol, 30% yield, chiral purity: 99.9%).

MS ESI m/z 331.0 (M+H).

1C(a): (R)-1-(2-fluoro-5-(trifluoromethoxy)phenyl)ethan-2,2,2-d$_3$-1-amine, HCl: A solution of (S)—N—((R)-1-(2-fluoro-5-(trifluoromethoxy)phenyl)ethyl-2,2,2-d$_3$)-2-methylpropane-2-sulfinamide (1.61 g, 4.87 mmol) and HCl (4 M in dioxane) (7.30 mL, 29.2 mmol) in THF (10 mL) was stirred at 23° C. for 1 h. The reaction mixture was concentrated and triturated in ether (10 mL). The solid was collected as (R)-1-(2-fluoro-5-(trifluoromethoxy)phenyl)ethan-2,2,2-d$_3$-1-amine, HCl (996 mg, 3.79 mmol, 78% yield).

MS ESI m/z 227.1 (M+H)

$^1$H NMR (400 MHz, CD$_3$OD) δ 7.57-7.34 (m, 3H), 4.75 (s, 1H).

(b): (S)-1-(2-fluoro-5-(trifluoromethoxy)phenyl)ethan-2,2,2-d3-1-amine, HCl: A solution of (S)—N—((S)-1-(2-fluoro-5-(trifluoromethoxy)phenyl)ethyl-2,2,2-d$_3$)-2-methylpropane-2-sulfinamide (0.97 g, 2.94 mmol) and HCl (4 M in dioxane) (4.40 mL, 17.62 mmol) in THF (8 mL) was stirred at 23° C. for 1 h. The reaction mixture was concentrated and triturated in ether (10 mL). The solid was collected as (S)-1-(2-fluoro-5-(trifluoromethoxy) phenyl)ethan-2,2,2-d$_3$-1-amine, HCl (592 mg, 2.25 mmol, 77% yield).

MS ESI m/z 227.1 (M+H).

$^1$H NMR (400 MHz, CD$_3$OD) δ 7.50 (dd, J=5.8, 2.8 Hz, 1H), 7.47-7.42 (m, 1H), 7.41-7.34 (m, 1H), 4.75 (s, 1H).

1D: 2-ethyl d$_5$-isoindoline-1,3-dione: A solution of potassium phthalamide (1.0 g, 5.40 mmol) and iodoethane-d$_5$ (0.446 mL, 5.40 mmol) in NMP (15 mL) was heated to 150° C. for 60 min under microwave. The reaction mixture was diluted with EtOAc (120 mL), then washed with water (50 mL), 10% LiCl solution (50 mL) and brine (50 mL).

The organics were dried over Na$_2$SO$_4$. Filtration and concentration yielded a crude product which was purified on a silica gel column with hexanes/EtOAc (100/0 to 50/50) to afford 2-ethyl d$_5$-isoindoline-1,3-dione (637.3 mg, 3.54 mmol, 66% yield).

MS ESI m/z 181.1 (M+H).

1E: ethan-d$_5$-1-amine, HCl: A solution of 2-ethyl d$_5$-isoindoline-1,3-dione (637.3 mg, 3.54 mmol) in HCl (6N solution) (0.589 mL, 3.54 mmol) was heated to 160° C. for 60 min under microwave. The reaction mixture was filtered and the aqueous phase concentrated. The crude material was triturated in ether (20 mL). The solid was collected as ethan-d$_5$-1-amine, HCl (319.3 mg, 3.69 mmol, 100% yield).

1F: 6-bromo-N-(ethyl-d$_5$)-1H-indazole-3-carboxamide: To a solution of 6-bromo-1H-indazole-3-carboxylic acid (0.5 g, 2.074 mmol), ethan-d$_5$-1-amine, HCl (0.180 g, 2.074 mmol) and DIPEA (0.906 mL, 5.19 mmol) in DMF (10 mL) was added BOP (1.147 g, 2.59 mmol). The reaction mixture was stirred at 23° C. for 16 h. The reaction mixture was concentrated and transferred to a separatory funnel with EtOAc (100 mL). The organics were washed with water (20 mL×2) and brine (20 mL) and dried over Na$_2$SO$_4$. Filtration and concentration yielded a crude product which was triturated in MeOH (3 mL) The solid was collected as the desired product. The filtrate was concentrated and purified on silica gel column with hexanes/EtOAc (100/0 to 0/100) to yield the second batch of desired product. The product was combined as 6-bromo-N-(ethyl-d$_5$)-1H-indazole-3-carboxamide (416 mg, 1.52 mmol, 74% yield).

MS ESI m/z 273.1 (M+H).

1G: tert-butyl 6-bromo-3-((ethyl-d$_5$)carbamoyl)-1H-indazole-1-carboxylate: To a solution of 6-bromo-N-(ethyl-d$_5$)-

1H-indazole-3-carboxamide (416 mg, 1.523 mmol), DMAP (18.61 mg, 0.152 mmol) and TEA (0.212 mL, 1.523 mmol) in $CH_2Cl_2$ (6 mL) was added Boc anhydride (0.354 mL, 1.523 mmol) at 0° C., and the reaction mixture was warmed to 23° C. and stirred for 6 h. The reaction mixture was concentrated and purified on silica gel column with hexanes/ EtOAc (100/0 to 0/100) to yield tert-butyl 6-bromo-3-((ethyl-$d_5$)carbamoyl)-1H-indazole-1-carboxylate (430 mg, 1.149 mmol, 75% yield).

MS ESI m/z 373.1 (M+H)

$^1$H NMR (400 MHz, $CD_3OD$) δ 8.38 (d, J=1.1 Hz, 1H), 8.22 (d, J=8.6 Hz, 1H), 7.60 (dd, J=8.6, 1.6 Hz, 1H), 1.76 (s, 9H).

1H: methyl $d_3$ 5-bromo-2-methoxy $d_3$-nicotinate: Sodium (1.156 g, 50.3 mmol) was added to $CD_3OD$ (20 mL) and stirred until the reaction was complete. To the mixture was added methyl 5-bromo-2-chloronicotinate (4.5 g, 17.97 mmol) and stirring was continued for 16 h. The reaction mixture was acidified with concentrated HCl solution until pH7. The solution was diluted with $CH_2Cl_2$ (100 mL) and washed with water (20 mL) and brine (20 mL) and dried over $Na_2SO_4$. Filtration and concentration yielded methyl $d_3$ 5-bromo-2-methoxy $d_3$-nicotinate (4.189 g, 15.99 mmol, 89% yield).

MS ESI m/z 251.1 (M+H).

1I: Methyl-d3 2-(methoxy-d3)-5-(4,4,5,5-tetramethyl-1,3,2-dioxaborolan-2-yl)nicotinate: A degassed solution of methyl $d_3$ 5-bromo-2-methoxy $d_3$-nicotinate (330 mg, 1.309 mmol), 4,4,4',4',5,5,5',5'-octamethyl-2,2'-bi(1,3,2-dioxaborolane) (399 mg, 1.571 mmol), potassium acetate (193 mg, 1.964 mmol) and $PdCl_2$(dppf)-$CH_2Cl_{1-2}$ adduct (64.1 mg, 0.079 mmol) in dioxane (6 mL) was heated to 65° C. for 16 h. The reaction mixture was filtered through Celite. The solution was concentrated to afford the product which was used as-is.

MS ESI m/z 218.1 (M+H of boronic acid).

1J: tert-butyl 3-((ethyl-$d_5$)carbamoyl)-6-(6-(methoxy-$d_3$)-5-((methoxy-$d_3$)carbonyl)pyridin-3-yl)-1H-indazole-1-carboxylate: A degassed solution of tert-butyl 6-bromo-3-((ethyl-$d_5$)carbamoyl)-1H-indazole-1-carboxylate (430 mg, 1.152 mmol), (6-methoxy $d_3$-5-(methoxy $d_3$-carbonyl)pyridin-3-yl)boronic acid (275 mg, 1.267 mmol), $PdCl_2$(dppf)-$CH_2Cl_2$ adduct (56.4 mg, 0.069 mmol) and potassium phosphate tribasic, 2M solution (1.728 mL, 3.46 mmol) in DMF (6 mL) was stirred at 23° C. for 2 h. EtOAc (100 mL) was added to the reaction mixture. The organics were washed with 10% LiCl solution (20 mL×2) and brine (20 mL) and dried over $Na_2SO_4$. Filtration and concentration yielded a crude product which was purified on a silica gel column with $CH_2Cl_{1-2}$/MeOH (100/0 to 90/10) to give tert-butyl 3-((ethyl-$d_5$)carbamoyl)-6-(6-(methoxy-$d_3$)-5-((methoxy-$d_3$)carbonyl)pyridin-3-yl)-1H-indazole-1-carboxylate (536 mg, 1.152 mmol, 100% yield).

MS ESI m/z 466.3 (M+H).

1K: 5-(3-((ethyl-d5)carbamoyl)-1H-indazol-6-yl)-2-(methoxy-d3)nicotinic acid, sodium salt: A solution of tert-butyl 3-((ethyl-$d_5$)carbamoyl)-6-(6-(methoxy-$d_3$)-5-((methoxy-$d_3$)carbonyl)pyridin-3-yl)-1H-indazole-1-carboxylate (536 mg, 1.151 mmol) and NaOH (1 M solution) (2.88 mL, 2.88 mmol) in MeOH (10 mL) was heated to 110° C. for 15 min under microwave. The reaction mixture was concentrated to yield 5-(3-((ethyl-$d_5$)carbamoyl)-1H-indazol-6-yl)-2-(methoxy-$d_3$)nicotinic acid, sodium salt (651 mg, 1.76 mmol, quantitative crude yield).

MS ESI m/z 349.1 (M+H).

1: To a solution of 5-(3-((ethyl-$d_5$)carbamoyl)-1H-indazol-6-yl)-2-(methoxy-$d_3$)nicotinic acid, sodium salt (20 mg, 0.057 mmol), (S)-1-(2-fluoro-5-(trifluoromethoxy)phenyl) ethan-2,2,2-d3-1-amine, HCl (15.08 mg, 0.057 mmol) and DIPEA (0.030 mL, 0.172 mmol) in DMF (1 mL) was added BOP (30.5 mg, 0.069 mmol). The reaction mixture was stirred at 23° C. for 2 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 34-74% B over 20 min, then a 4-min hold at 100% B; Flow: 20 mL/min. Fractions containing the desired product were combined and dried via centrifugal evaporation. N—[(1,1,2,2,2-deutero)ethyl]-6-(5-{[(1S)-1-[2-fluoro-5-(trifluoromethoxy)phenyl](2,2,2-deutero)ethyl]carbamoyl}-6-(deutero) methoxypyridin-3-yl)-1H-indazole-3-carboxamide (7.3 mg, 13.1 μmol, 23% yield) was isolated.

MS ESI m/z 557.3 (M+H)

$^1$H NMR (500 MHz, DMSO-$d_6$) δ 8.89 (br d, J=7.6 Hz, 1H), 8.72 (d, J=2.1 Hz, 1H), 8.40 (s, 1H), 8.31-8.23 (m, 2H), 7.85 (s, 1H), 7.62-7.53 (m, 2H), 7.42-7.29 (m, 2H), 5.37 (br d, J=7.3 Hz, 1H).

Example 2 (R)—N-(ethyl-d5)-6-(6-(methoxy-d3)-5-((1-(2-(trifluoromethoxy)phenyl)ethyl) carbamoyl) pyridin-3-yl)-1H-indazole-3-carboxamide

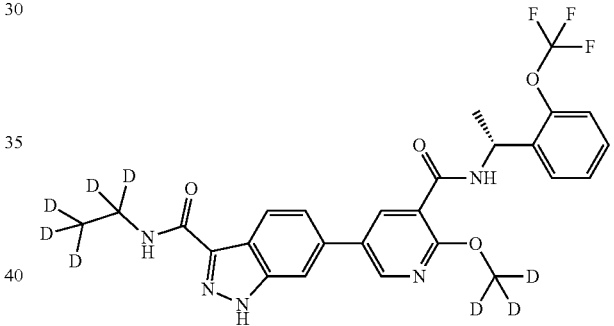

2A: (R,E)-2-methyl-N-(2-(trifluoromethoxy)benzylidene)propane-2-sulfinamide: A method substantially similar to that described in 1A, was used to afford (R,E)-2-methyl-N-(2-(trifluoromethoxy)benzylidene)propane-2-sulfinamide (2.61 g, 8.89 mmol, 85% yield).

MS ESI m/z 294.1 (M+H)

$^1$H NMR (400 MHz, $CDCl_3$) δ 8.93 (s, 1H), 8.12 (dd, J=7.8, 1.7 Hz, 1H), 7.64-7.51 (m, 1H), 7.47-7.33 (m, 2H), 1.30 (s, 9H).

2B: (R)-2-methyl-N—((S)-1-(2-(trifluoromethoxy)phenyl)ethyl)propane-2-sulfinamide (a) and (R)-2-methyl-N—((R)-1-(2-(trifluoromethoxy)phenyl)ethyl)propane-2-sulfinamide (b): A method substantially similar to that described in 1B, was used to afford (R)-2-methyl-N—((S)-1-(2-(trifluoromethoxy)phenyl)ethyl)propane-2-sulfinamide (a) (1.67 g, 5.40 mmol, 60% yield, chiral purity: 99.8%)

MS ESI m/z 310.1 (M+H)

$^1$H NMR (400 MHz, $CDCl_3$) δ 7.51-7.46 (m, 1H), 7.34-7.25 (m, 3H merge with chloroform), 4.98 (dd, J=6.7, 4.6 Hz, 1H), 1.59-1.55 (m, 3H), 1.21 (s, 9H).

(R)-2-methyl-N—((R)-1-(2-(trifluoromethoxy)phenyl) ethyl)propane-2-sulfinamide (b) (0.773 g, 2.474 mmol, 27% yield, chiral purity: 98.5%.

MS ESI m/z 310.1 (M+H)

¹H NMR (400 MHz, CDCl₃) δ 7.55-7.48 (m, 1H), 7.36-7.25 (m, 3H merge with chloroform), 4.92 (qd, J=6.6, 4.6 Hz, 1H), 3.55-3.42 (m, 1H), 1.53 (d, J=6.6 Hz, 3H), 1.25 (s, 9H).

2C (a): (S)-1-(2-(trifluoromethoxy)phenyl)ethanamine, HCl: A method substantially similar to that described in 2C, was used to afford (S)-1-(2-(trifluoromethoxy)phenyl) ethanamine, HCl (1.3 g, 5.38 mmol, 100% yield).

MS ESI m/z 206.1 (M+H)

¹H NMR (400 MHz, CD₃OD) δ 7.66 (dd, J=7.5, 2.0 Hz, 1H), 7.60-7.49 (m, 2H), 7.48-7.44 (m, 1H), 4.80 (q, J=6.8 Hz, 1H), 1.64 (d, J=7.0 Hz, 3H).

(b): (R)-1-(2-(trifluoromethoxy)phenyl)ethanamine, HCl: (R)-1-(2-(trifluoromethoxy)phenyl)ethanamine, HCl (548 mg, 2.27 mmol, 91% yield).

MS ESI m/z 206.1 (M+H)

¹H NMR (400 MHz, CD₃OD) δ 7.66 (dd, J=7.5, 2.0 Hz, 1H), 7.60-7.49 (m, 2H), 7.48-7.44 (m, 1H), 4.81 (q, J=6.8 Hz, 1H), 1.64 (d, J=6.8 Hz, 3H) 2: To a solution of 5-(3-((ethyl-d5)carbamoyl)-1H-indazol-6-yl)-2-(methoxy-d3)nicotinic acid (1H) (20 mg, 0.057 mmol), (R)-1-(2-(trifluoromethoxy)phenyl)ethan-1-amine, HCl (2C-b) (13.87 mg, 0.057 mmol) and DIPEA (0.030 mL, 0.172 mmol) in DMF (1 mL) was added BOP (30.5 mg, 0.069 mmol). The reaction mixture was stirred at 23° C. for 2 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 34-74% B over 20 minutes, then a 4-minute hold at 100% B; Flow: 20 mL/min. Fractions containing the desired product were combined and dried via centrifugal evaporation. (R)—N-(ethyl-d5)-6-(6-(methoxy-d3)-5-((1-(2-(trifluoromethoxy)phenyl)ethyl)carbamoyl)pyridin-3-yl)-1H-indazole-3-carboxamide (9.2 mg, 17.2 μmol, 30% yield) was isolated.

MS ESI m/z 536.2 (M+H)

¹H NMR (500 MHz, DMSO-d₆) δ 8.80 (br d, J=7.6 Hz, 1H), 8.71 (d, J=2.4 Hz, 1H), 8.40 (s, 1H), 8.33 (d, J=2.1 Hz, 1H), 8.26 (d, J=8.2 Hz, 1H), 7.85 (s, 1H), 7.71-7.66 (m, 1H), 7.58 (d, J=8.5 Hz, 1H), 7.46-7.40 (m, 2H), 7.38 (br s, 1H), 5.44 (br t, J=1.2 Hz, 1H), 1.48 (d, J=7.0 Hz, 3H)

Example 3 (R)-6-(6-(methoxy-d3)-5-((1-(3-(trifluoromethyl)phenyl)ethyl)carbamoyl)pyridin-3-yl)-N-(methyl-d3)-1H-indazole-3-carboxamide

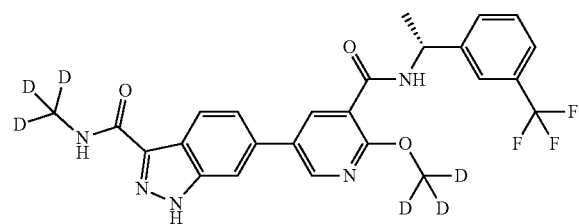 [SMILES: [2H]C([2H])([2H])NC(=O)c1n[nH]c2cc(-c3cnc(OC([2H])([2H])[2H])c(C(=O)N[C@H](C)c4cccc(C(F)(F)F)c4)c3)ccc12]

3A: (R)-1-(3-(trifluoromethyl)phenyl)ethan-1-amine, HCl: The similar protocols leading to 1C(a) were used to afford (R)-1-(3-(trifluoromethyl)phenyl) ethan-1-amine, HCl (201 mg, 0.836 mmol, 80% yield).

MS ESI m/z 190.1 (M+H)

¹H NMR (400 MHz, CD₃OD) δ 7.83 (s, 1H), 7.79-7.74 (m, 2H), 7.73-7.66 (m, 1H), 4.59 (q, J=6.8 Hz, 1H), 1.67 (d, J=6.8 Hz, 3H).

3B: 2-(methoxy-d3)-5-(3-((methyl-d3)carbamoyl)-1H-indazol-6-yl)nicotinic acid: Similar protocols leading to 1H were used to afford 2-(methoxy-d3)-5-(3-((methyl-d3)carbamoyl)-1H-indazol-6-yl)nicotinic acid (283 mg, 0.852 mmol).

3: A method substantially similar to that mentioned in 1, was used to afford (R)-6-(6-(methoxy-d3)-5-((1-(3-(trifluoromethyl)phenyl)ethyl)carbamoyl)pyridin-3-yl)-N-(methyl-d3)-1H-indazole-3-carboxamide (10.9 mg, 21.6 μmol, 48% yield).

MS ESI m/z 504.3 (M+H)

¹H NMR (500 MHz, DMSO-d₆) δ 8.85 (br d, J=7.9 Hz, 1H), 8.70 (d, J=2.1 Hz, 1H), 8.35 (s, 1H), 8.28 (d, J=2.4 Hz, 1H), 8.25 (d, J=8.5 Hz, 1H), 7.86 (s, 1H), 7.82 (s, 1H), 7.76 (br d, J=6.7 Hz, 1H), 7.66-7.56 (m, 3H), 5.26 (quin, J=7.2 Hz, 1H), 1.52 (d, J=7.0 Hz, 3H).

Example 4 (R)-6-(5-((1-(2-fluoro-5-(trifluoromethyl)phenyl)ethyl-2,2,2-d3)carbamoyl)-6-(methoxy-d3)pyridin-3-yl)-N-methyl-1H-indazole-3-carboxamide, TFA

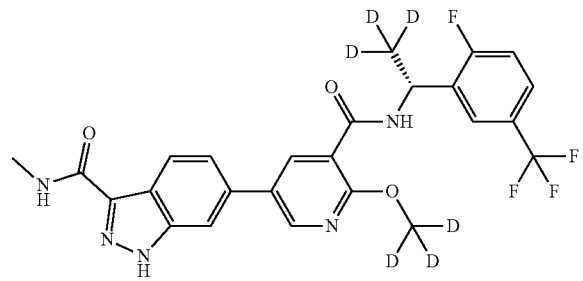 [SMILES: [2H]C([2H])([2H])Oc1ncc(-c2ccc3c(C(=O)NC)n[nH]c3c2)cc1C(=O)N[C@@H](c1cc(C(F)(F)F)ccc1F)C([2H])([2H])[2H]]

4A: (R)-1-(2-fluoro-5-(trifluoromethyl)phenyl)ethan-2,2,2-d3-1-amine, HCl: The similar protocols leading to 1C(a) were used to afford (R)-1-(2-fluoro-5-(trifluoromethyl) phenyl)ethan-2,2,2-d3-1-amine, HCl (624 mg, 2.472 mmol, 98% yield).

MS ESI m/z 211.1 (M+H)

¹H NMR (400 MHz, CD₃OD) δ 7.91 (br d, J=6.6 Hz, 1H), 7.88-7.82 (m, 1H), 7.48 (t, J=9.4 Hz, 1H), 4.82 (s, 1H).

4B: 2-(methoxy-d3)-5-(3-(methylcarbamoyl)-1H-indazol-6-yl)nicotinic acid: The similar protocols leading to 1H were used to afford 2-(methoxy-d3)-5-(3-(methylcarbamoyl)-1H-indazol-6-yl)nicotinic acid (266 mg, 0.808 mmol).

MS ESI m/z 330.1 (M+H).

4: A method substantially similar to that mentioned in 1, was used to afford (R)-6-(5-((1-(2-fluoro-5-(trifluoromethyl)phenyl)ethyl-2,2,2-d3)carbamoyl)-6-(methoxy-d3) pyridin-3-yl)-N-methyl-1H-indazole-3-carboxamide, TFA (7.2 mg, 11.3 μmol, 25% yield).

MS ESI m/z 522.2 (M+H)

¹H NMR (500 MHz, DMSO-d₆) δ 8.92 (d, J=7.6 Hz, 1H), 8.66 (d, J=2.1 Hz, 1H), 8.34 (br d, J=4.9 Hz, 1H), 8.25-8.18 (m, 2H), 7.90 (br d, J=5.2 Hz, 1H), 7.81 (s, 1H), 7.74-7.66

(m, 1H), 7.53 (d, J=8.5 Hz, 1H), 7.43 (t, J=93 Hz, 1H), 5.37 (d, J=7.6 Hz, 1H), 2.80 (d, J=4.6 Hz, 3H).

Example 5 (S)-6-(5-((1-(2-fluoro-5-(trifluoromethoxy)phenyl)ethyl) carbamoyl)-6-(methoxy-d3)pyridin-3-yl)-N-(methyl-d3)-1H-indazole-3-carboxamide

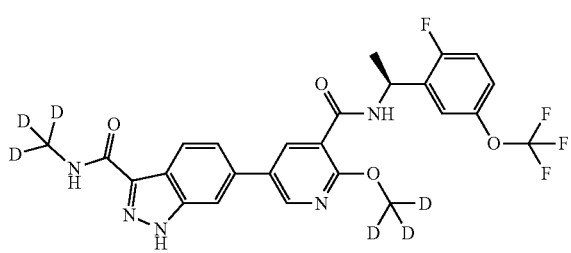 [SMILES: [2H]C([2H])([2H])NC(=O)c1n[nH]c2cc(-c3cnc(OC([2H])([2H])[2H])c(C(=O)N[C@@H](C)c4cc(OC(F)(F)F)ccc4F)c3)ccc12]

5A: (S)-1-(2-fluoro-5-(trifluoromethoxy)phenyl)ethan-1-amine, HCl: Similar protocols leading to 1C(b) were used to afford (S)-1-(2-fluoro-5-(trifluoromethoxy)phenyl)ethan-1-amine, HCl.

5: A method substantially similar to that described in 1 was used to afford (S)-6-(5-((1-(2-fluoro-5-(trifluoromethoxy)phenyl)ethyl)carbamoyl)-6-(methoxy-d3)pyridin-3-yl)-N-(methyl-d3)-1H-indazole-3-carboxamide (10.4 mg, 19.3 µmol, 43% yield).

MS ESI m/z 538.2 (M+H)

$^1$H NMR (500 MHz, DMSO-d$_6$) δ 8.90 (br d, J=7.6 Hz, 1H), 8.72 (d, J=2.1 Hz, 1H), 8.35 (s, 1H), 8.30-8.24 (m, 2H), 7.86 (s, 1H), 7.61-7.51 (m, 2H), 7.44-7.30 (m, 2H), 5.39 (br t, J=12 Hz, 1H), 1.50 (d, J=7.0 Hz, 3H).

Example 6 (R)-6-(5-((1-(2-fluoro-5-(trifluoromethyl)phenyl) ethyl)carbamoyl)-6-(methoxy-d3)pyridin-3-yl)-N-(methyl-d3)-1H-indazole-3-carboxamide

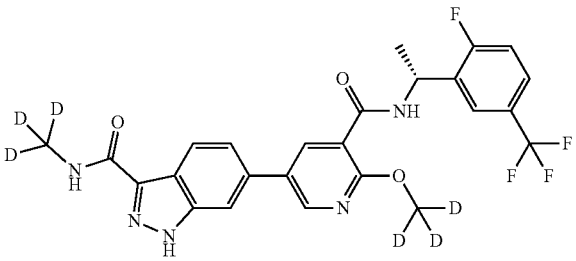 [SMILES: [2H]C([2H])([2H])NC(=O)c1n[nH]c2cc(-c3cnc(OC([2H])([2H])[2H])c(C(=O)N[C@H](C)c4cc(C(F)(F)F)ccc4F)c3)ccc12]

6A: (R)-1-(2-fluoro-5-(trifluoromethyl)phenyl)ethan-1-amine, HCl: Similar protocols leading to 1C(a) were used to afford (R)-1-(2-fluoro-5-(trifluoromethyl)phenyl)ethan-1-amine, HCl.

6: A method substantially similar to that described in 1 was used to afford (R)-6-(5-((1-(2-fluoro-5-(trifluoromethyl)phenyl) ethyl)carbamoyl)-6-(methoxy-d3)pyridin-3-yl)-N-(methyl-d3)-1H-indazole-3-carboxamide (9.2 mg, 17.6 µmol, 39% yield).

MS ESI m/z 522.3 (M+H)

$^1$H NMR (500 MHz, DMSO-d$_6$) δ 8.96 (br d, J=7.6 Hz, 1H), 8.72 (d, J=2.1 Hz, 1H), 8.35 (s, 1H), 8.30-8.19 (m, 2H), 7.96 (br d, J=5.2 Hz, 1H), 7.86 (s, 1H), 7.75 (br d, J=3.1 Hz, 1H), 7.58 (d, J=8.5 Hz, 1H), 7.48 (br t, J=9.3 Hz, 1H), 5.44 (br t, J=7.3 Hz, 1H), 1.51 (d, J=7.0 Hz, 3H).

Example 7 (R)-6-(6-(methoxy-d3)-5-((1-(2-(trifluoromethoxy)phenyl) ethyl)carbamoyl)pyridin-3-yl)-N-(methyl-d3)-1H-indazole-3-carboxamide

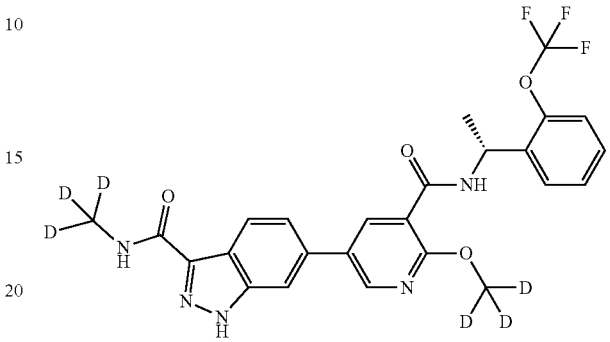

A method substantially similar to that described in 1 was used to afford (R)-6-(6-(methoxy-d3)-5-((1-(2-(trifluoromethoxy)phenyl) ethyl)carbamoyl)pyridin-3-yl)-N-(methyl-d3)-1H-indazole-3-carboxamide (21.1 mg, 40.6 µmol, 90% yield).

MS ESI m/z 520.4 (M+H)

$^1$H NMR (500 MHz, DMSO-d$_6$) δ 8.80 (br d, J=7.6 Hz, 1H), 8.71 (d, J=2.4 Hz, 1H), 8.37-8.30 (m, 2H), 8.26 (d, J=8.5 Hz, 1H), 7.85 (s, 1H), 7.71-7.65 (m, 1H), 7.58 (br d, J=8.5 Hz, 1H), 7.46-7.40 (m, 2H), 7.38 (br s, 1H), 5.49-5.38 (m, 1H), 1.48 (d, J=7.0 Hz, 3H).

Example 8 (R)-6-(6-(methoxy-d3)-5-((1-(3-(trifluoromethoxy) phenyl)ethyl)carbamoyl)pyridin-3-yl)-N-(methyl-d3)-1H-indazole-3-carboxamide, TFA

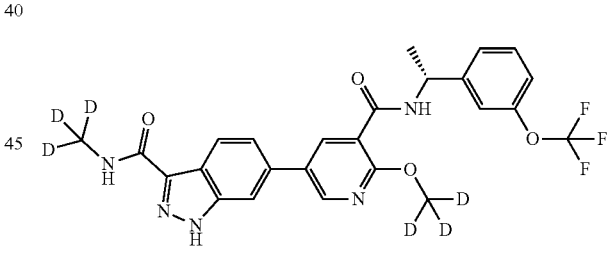

8A: (R)-1-(3-(trifluoromethoxy)phenyl)ethan-1-amine, HCl: Similar protocols leading to 1C(a) were used to afford (R)-1-(3-(trifluoromethoxy) phenyl)ethan-1-amine, HCl (R)-1-(3-(trifluoromethoxy)phenyl)ethan-1-amine, HCl (542 mg, 2.158 mmol, 90% yield).

MS ESI m/z 206.1 (M+H)

$^1$H NMR (400 MHz, CD$_3$OD) δ 7.65-7.56 (m, 1H), 7.50 (d, J=7.8 Hz, 1H), 7.44 (s, 1H), 7.38 (br d, J=8.2 Hz, 1H), 4.56 (q, J=6.8 Hz, 1H), 1.66 (d, J=6.8 Hz, 3H).

8: A method substantially similar to that described in 1 was used to afford (R)-6-(6-(methoxy-d3)-5-((1-(3-(trifluoromethoxy) phenyl)ethyl)carbamoyl)pyridin-3-yl)-N-(methyl-d3)-1H-indazole-3-carboxamide, TFA (11 mg, 17.4 µmol, 39% yield).

MS ESI m/z 520.2 (M+H)

$^1$H NMR (500 MHz, DMSO-d$_6$) δ 8.72-8.64 (m, 2H), 8.31 (d, J=2.4 Hz, 1H), 8.27 (d, J=8.4 Hz, 1H), 8.19 (s, 1H), 7.83 (s, 1H), 7.56 (d, J=8.5 Hz, 1H), 7.54-7.46 (m, 2H), 7.44 (s, 1H), 7.24 (br d, J=7.5 Hz, 1H), 5.29-5.17 (m, 1H), 1.52 (d, J=7.1 Hz, 3H).

Example 9 (R)-6-(5-((1-(2-fluoro-5-(trifluoromethoxy)phenyl)ethyl-2,2,2-d3)carbamoyl)-6-(methoxy-d3)pyridin-3-yl)-N-methyl-1H-indazole-3-carboxamide, TFA

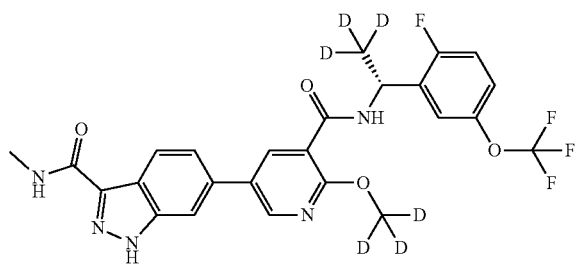 [SMILES: [2H]C([2H])([2H])Oc1ncc(-c2ccc3c(C(=O)NC)n[nH]c3c2)cc1C(=O)N[C@@H](c1cc(OC(F)(F)F)ccc1F)C([2H])([2H])[2H]]

A method substantially similar to that described in 1 was used to afford (R)-6-(5-((1-(2-fluoro-5-(trifluoromethoxy)phenyl)ethyl-2,2,2-d3)carbamoyl)-6-(methoxy-d3)pyridin-3-yl)-N-methyl-1H-indazole-3-carboxamide, TFA (3.1 mg, 4.8 μmol, 10% yield).

MS ESI m/z 537.9 (M+H)

¹H NMR (500 MHz, DMSO-d₆) δ 8.89 (d, J=7.6 Hz, 1H), 8.71 (d, J=2.1 Hz, 1H), 8.38 (br d, J=4.9 Hz, 1H), 8.30-8.23 (m, 2H), 7.85 (s, 1H), 7.63-7.51 (m, 2H), 7.43-7.33 (m, 2H), 5.37 (d, J=7.6 Hz, 1H), 2.84 (d, J=4.6 Hz, 3H).

Example 10 (S)-6-(5-((1-(2-fluoro-5-(trifluoromethoxy)phenyl)ethyl-2,2,2-d3)carbamoyl)-6-(methoxy-d3)pyridin-3-yl)-N-methyl-1H-indazole-3-carboxamide

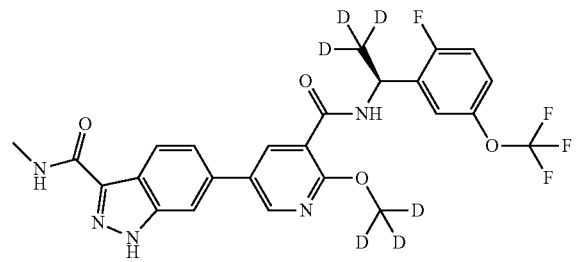 [SMILES: [2H]C([2H])([2H])Oc1ncc(-c2ccc3c(C(=O)NC)n[nH]c3c2)cc1C(=O)N[C@H](c1cc(OC(F)(F)F)ccc1F)C([2H])([2H])[2H]]

A method substantially similar to that described in 1 was used to afford (S)-6-(5-((1-(2-fluoro-5-(trifluoromethoxy)phenyl)ethyl-2,2,2-d3)carbamoyl)-6-(methoxy-d3)pyridin-3-yl)-N-methyl-1H-indazole-3-carboxamide (5 mg, 9.3 μmol, 20% yield).

MS ESI m/z 538 (M+H)

¹H NMR (500 MHz, DMSO-d₆) δ 8.89 (br d, J=7.6 Hz, 1H), 8.72 (d, J=2.4 Hz, 1H), 8.38 (br d, J=4.9 Hz, 1H), 8.30-8.20 (m, 2H), 7.85 (s, 1H), 7.62-7.54 (m, 2H), 7.44-7.32 (m, 2H), 5.37 (br d, J=7.6 Hz, 1H), 2.85 (d, J=4.6 Hz, 3H).

Example 11 (R)-6-(6-(methoxy-d3)-5-((1-(3-(trifluoromethoxy)phenyl) ethyl-2,2,2-d3)carbamoyl) pyridin-3-yl)-N-methyl-1H-indazole-3-carboxamide, TFA

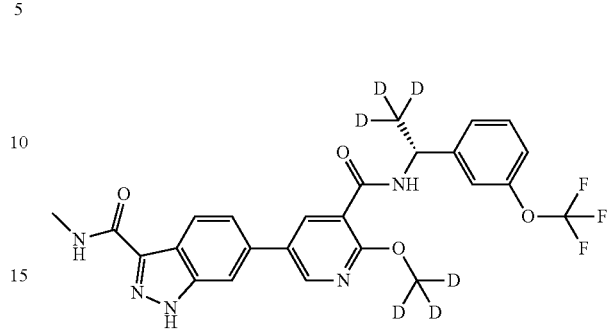

11A: (R)-1-(3-(trifluoromethoxy)phenyl)ethan-2,2,2-d3-1-amine: Similar protocols used to access 1C(a) were used to afford (R)-1-(3-(trifluoromethoxy) phenyl)ethan-2,2,2-d3-1-amine (345.2 mg, 1.636 mmol, 90% yield).

MS ESI m/z 209.1 (M+H)

¹H NMR (400 MHz, CD₃OD) δ 7.64-7.57 (m, 1H), 7.49 (d, J=7.8 Hz, 1H), 7.44 (s, 1H), 7.37 (dt, J=8.2, 1.1 Hz, 1H), 4.53 (s, 1H).

11: A method substantially similar to that described in 1 was used to afford (R)-6-(6-(methoxy-d3)-5-((1-(3-(trifluoromethoxy)phenyl) ethyl-2,2,2-d3)carbamoyl)pyridin-3-yl)-N-methyl-1H-indazole-3-carboxamide, TFA (7.6 mg, 12 μmol, 25% yield).

MS ESI m/z 520.2 (M+H)

¹H NMR (500 MHz, DMSO-d₆) δ 8.78 (br d, J=7.9 Hz, 1H), 8.70 (d, J=2.1 Hz, 1H), 8.37 (br d, J=4.6 Hz, 1H), 8.31-8.22 (m, 2H), 7.85 (s, 1H), 7.58 (br d, J=8.5 Hz, 1H), 7.54-7.40 (m, 3H), 7.26 (br d, J=7.3 Hz, 1H), 5.20 (br d, J=7.6 Hz, 1H), 2.84 (d, J=4.9 Hz, 3H).

Example 12 6-(5-(((3R,4S)-1-(3,3-difluorocyclobutanecarbonyl)-4-fluoropyrrolidin-3-yl)carbamoyl)-6-methoxy d3-pyridin-3-yl)-N-methyl d3-1H-indazole-3-carboxamide

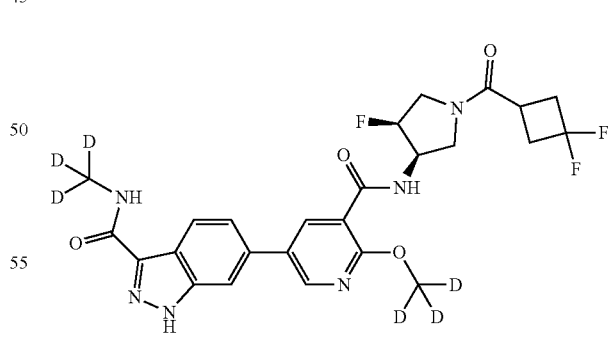

12A: 1-tert-butyl 3-methyl 6-bromo-1H-indazole-1,3-dicarboxylate: To a solution of methyl 6-bromo-1H-indazole-3-carboxylate (0.5 g, 1.960 mmol), DMAP (0.024 g, 0.196 mmol) and TEA (0.478 mL, 3.43 mmol) in CH₂Cl₂ (14 mL) was added Boc anhydride (0.683 mL, 2.94 mmol) at 0° C. The reaction mixture was warmed up to 23° C. and stirred for 24 h. The reaction mixture was concentrated and triturated in MeOH (5 mL). The solid was collected as 1-tertbutyl 3-methyl 6-bromo-1H-indazole-1,3-dicarboxylate (520 mg, 1.45 mmol, 74% yield).

MS ESI m/z 355.1 (M+H)

12B: methyl d3 5-bromo-2-methoxy d3-nicotinate: Sodium (0.51 g, 22.36 mmol) was added to CD$_3$OD (10 mL) and stirred until the reaction was complete. To the reaction mixture was added methyl 5-bromo-2-chloronicotinate (2.0 g, 7.98 mmol) and stirring was continued for 16 h. The reaction mixture was acidified with concentrated HCl solution and diluted with dichloromethane (100 mL). The organics were washed with water (20 mL), brine (20 mL) and dried over Na$_2$SO$_4$. Filtration and concentration yielded methyl d3 5-bromo-2-methoxy d3-nicotinate (1.67 g, 6.62 mmol, 83% yield).

MS ESI m/z 251.1 (M+H)

$^1$H NMR (400 MHz, CD$_3$OD) δ 8.40 (d, J=2.6 Hz, 1H), 8.28 (d, J=2.6 Hz, 1H).

12C: 5-bromo-2-methoxy d3-nicotinic acid, sodium salt: A solution of methyl d3 5-bromo-2-methoxy d3-nicotinate (800 mg, 3.17 mmol) and NaOH (4.76 mL, 4.76 mmol) in MeOH (15 mL) was heated to 100° C. for 30 min under microwave. The reaction mixture was concentrated to yield 5-bromo-2-methoxy d3-nicotinic acid, sodium salt. Material was used as is in subsequent reaction.

MS ESI m/z 236.9 (M+H).

12D: (3R,4S)-tert-butyl 3-(5-bromo-2-methox d3-ynicotinamido)-4-fluoropyrrolidine-1-carboxylate: To a solution of 5-bromo-2-methoxy d3-nicotinic acid, sodium salt (750 mg, 3.19 mmol), cis-1-boc-3-amino-4-fluoropyrrolidine (652 mg, 3.19 mmol) and DIPEA (0.669 mL, 3.83 mmol) in DMF (15 mL) was added BOP (1693 mg, 3.83 mmol). The reaction mixture was stirred at 23° C. for 1 h. The reaction mixture was concentrated. EtOAc (150 mL) was added to the crude material. The organics were washed with water (50 mL), brine (50 mL) and dried over Na$_2$SO$_4$. Filtration and concentration yielded a crude product which was triturated in water (50 mL). The solid was collected as (3R,4S)-tert-butyl 3-(5-bromo-2-methox d3-ynicotinamido)-4-fluoropyrrolidine-1-carboxylate (1.23 g, 2.92 mmol, 92% yield) as the mixture of cis isomers.

MS ESI m/z 421.1 (M+H)

$^1$H NMR (400 MHz, CD$_3$OD) δ 8.43-8.31 (m, 2H), 5.34-5.07 (m, 1H), 4.80-4.64 (m, 1H), 3.99-3.85 (m, 1H), 3.78-3.54 (m, 2H), 3.22 (td, J=10.3, 4.8 Hz, 1H), 1.49 (s, 9H).

The racemic mixture was separated using chiral SFC conditions to yield two peaks, 12D-1 (414.6 mg, 0.984 mmol) and 12D-2 (426.0 mg, 1.011 mmol). 12D-2 was carried forward into subsequent chemistry.

12D-1:

MS ESI m/z 421.1 (M+H)

$^1$H NMR (400 MHz, CD$_3$OD) δ 8.41-8.39 (m, 1H), 8.38 (d, J=2.6 Hz, 1H), 5.33-5.11 (m, 1H), 4.81-4.65 (m, 1H), 3.98-3.87 (m, 1H), 3.77-3.55 (m, 2H), 3.22 (td, J=10.3, 5.0 Hz, 1H), 1.49 (s, 9H).

12D-2:

MS ESI m/z 421.1 (M+H)

$^1$H NMR (400 MHz, CD$_3$OD) δ 8.41-8.39 (m, 1H), 8.38 (d, J=2.6 Hz, 1H), 5.33-5.08 (m, 1H), 4.80-4.64 (m, 1H), 3.97-3.88 (m, 1H), 3.77-3.55 (m, 2H), 3.22 (td, J=10.4, 5.0 Hz, 1H), 1.49 (s, 9H).

12E: 5-bromo-N-((3R,4S)-4-fluoropyrrolidin-3-yl)-2-methoxy d3-nicotinamide, TFA: To a solution of (3R,4S)-tert-butyl 3-(5-bromo-2-methoxy d3-nicotinamido)-4-fluoropyrrolidine-1-carboxylate (200 mg, 0.475 mmol) in CH$_2$Cl$_2$ (2 mL) was added TFA (0.914 mL, 11.87 mmol). After stirring at 23° C. for 1 h, the reaction mixture was concentrated and triturated in diethyl ether (5 mL). The solid was collected as 5-bromo-N-((3R,4S)-4-fluoropyrrolidin-3-yl)-2-methoxy d3-nicotinamide, TFA.

MS ESI m/z 320.9 (M+H).

12F: 5-bromo-N-((3R,4S)-1-(3,3-difluorocyclobutanecarbonyl)-4-fluoropyrrolidin-3-yl)-2-methoxy d3-nicotinamide: To a solution of 5-bromo-N-((3R,4S)-4-fluoropyrrolidin-3-yl)-2-methoxy d3-nicotinamide, TFA (207 mg, 0.476 mmol), 3,3-difluorocyclobutanecarboxylic acid (64.7 mg, 0.476 mmol) and DIPEA (0.291 mL, 1.665 mmol) in DMF (3 mL) was added BOP (252 mg, 0.571 mmol). The reaction mixture was stirred at rt ON. The reaction mixture was concentrated and transferred to a separatory funnel with EtOAc (80 mL). The organics were washed with water (20 mL×3), brine (20 mL) and dried over Na$_2$SO$_4$. Filtration and concentration yielded a crude product which was purified on a silica gel column with Hexanes/EtOAc (100/0 to 0/100) to yield 5-bromo-N-((3R,4S)-1-(3,3-difluorocyclobutanecarbonyl)-4-fluoropyrrolidin-3-yl)-2-methoxy d3-nicotinamide (183 mg, 0.417 mmol, 88% yield).

MS ESI m/z 439.1 (M+H)

$^1$H NMR (400 MHz, CD$_3$OD) δ 8.43-8.35 (m, 2H), 5.40-5.14 (m, 1H), 4.82-4.68 (m, 1H), 4.14-4.02 (m, 1H), 3.95-3.63 (m, 2H), 3.44 (t, J=10.2 Hz, 1H), 3.24-3.10 (m, 1H), 2.92-2.76 (m, 4H).

12G: N-((3R,4S)-1-(3,3-difluorocyclobutanecarbonyl)-4-fluoropyrrolidin-3-yl)-2-methoxy d3-5-(4,4,5,5-tetramethyl-1,3,2-dioxaborolan-2-yl)nicotinamide: A degassed solution of 5-bromo-N-((3R,4S)-1-(3,3-difluorocyclobutanecarbonyl)-4-fluoropyrrolidin-3-yl)-2-methoxy d3-nicotinamide (183 mg, 0.417 mmol), 4,4,4',4',5,5,5',5'-octamethyl-2,2'-bi (1,3,2-dioxaborolane) (138 mg, 0.542 mmol), potassium acetate (65.4 mg, 0.667 mmol) and PdCl$_2$(dppf)-CH$_2$C$_{1-2}$ adduct (27.2 mg, 0.033 mmol) in dioxane (3 mL) was heated to 65° C. for 8 h. The reaction mixture was filtered through Celite. The solution was concentrated to afford the product which was used as-is.

MS ESI m/z 405.1 (M+H of boronic acid).

12H: 1-tert-butyl 3-methyl 6-(5-(((3R,4S)-1-(3,3-difluorocyclobutanecarbonyl)-4-fluoropyrrolidin-3-yl)carbamoyl)-6-methoxy d3-pyridin-3-yl)-1H-indazole-1,3-dicarboxylate: A degassed solution of N-((3R,4S)-1-(3,3-difluorocyclobutanecarbonyl)-4-fluoropyrrolidin-3-yl)-2-methoxy d3-5-(4,4,5,5-tetramethyl-1,3,2-dioxaborolan-2-yl)nicotinamide (205 mg, 0.421 mmol), 1-tert-butyl 3-methyl 6-bromo-1H-indazole-1,3-dicarboxylate (136 mg, 0.383 mmol), potassium phosphate tribasic 2 M solution (0.57 mL, 1.149 mmol) and 1,1'-bis(diphenylphosphino) ferrocene-palladium(II)dichloride dichloromethane complex (18.76 mg, 0.023 mmol) in DMF (3 mL) was stirred at 23° C. for 2 h. The reaction mixture was concentrated. EtOAc (80 mL) was added to the residue which was washed with water (20 mL), brine (20 mL) and dried over Na$_2$SO$_4$. Filtration and concentration yielded a crude product which was triturated with MeOH (2 mL). The solid was collected as 1-tert-butyl 3-methyl 6-(5-(((3R,4S)-1-(3,3-difluorocyclobutanecarbonyl)-4-fluoropyrrolidin-3-yl)carbamoyl)-6-methoxy d3-pyridin-3-yl)-1H-indazole-1,3-dicarboxylate (167.6 mg, 0.264 mmol, 69% yield).

MS ESI m/z 635.1 (M+H)

$^1$H NMR (400 MHz, DMSO-d$_6$) δ 8.78 (dd, J=5.1, 2.6 Hz, 1H), 8.57 (dd, J=10.0, 7.9 Hz, 1H), 8.45 (dd, J=7.0, 2.6 Hz, 1H), 8.41 (s, 1H), 8.27 (dd, J=8.4, 2.0 Hz, 1H), 7.91 (d, J=8.6 Hz, 1H), 5.46-5.18 (m, 1H), 4.92-4.61 (m, 1H), 4.09-3.58 (m, 6H), 3.42-3.26 (m, 1H merge with water), 3.24-3.11 (m, 1H), 2.92-2.70 (m, 4H), 1.71 (s, 9H).

12I: 6-(5-(((3R,4S)-1-(3,3-difluorocyclobutanecarbonyl)-4-fluoropyrrolidin-3-yl)carbamoyl)-6-methoxy d3-pyridin-3-yl)-1H-indazole-3-carboxylic acid: A method substantially similar to that described in 1H was used to afford 6-(5-(((3R,4S)-1-(3,3-difluorocyclobutanecarbonyl)-4-fluoropyrrolidin-3-yl)carbamoyl)-6-methoxy d3-pyridin-3-yl)-1H-indazole-3-carboxylic acid (130 mg, 0.245 mmol, 93% yield).

MS ESI m/z 521.1 (M+H)

¹H NMR (400 MHz, CD₃OD) δ 8.71 (t, J=3.0 Hz, 1H), 8.68-8.63 (m, 1H), 8.32 (d, J=8.4 Hz, 1H), 7.84 (s, 1H), 7.59 (d, J=8.6 Hz, 1H), 5.45-5.23 (m, 1H), 4.94-4.81 (m, 1H merge with MeOH), 4.21-3.68 (m, 4H), 3.28-3.18 (m, 1H), 2.91-2.78 (m, 4H).

12: A method substantially similar to that described in 1 was used to afford 6-(5-(((3R,4S)-1-(3,3-difluorocyclobutanecarbonyl)-4-fluoropyrrolidin-3-yl)carbamoyl)-6-methoxy d3-pyridin-3-yl)-N-methyl d3-1H-indazole-3-carboxamide (3.9 mg, 7.3 μmol, 38% yield).

MS ESI m/z 537.3 (M+H)

¹H NMR (500 MHz, DMSO-d₆) δ 8.72 (dd, J=5.5, 2.4 Hz, 1H), 8.49 (br dd, J=11.9, 7.7 Hz, 1H), 8.44 (dd, J=8.6, 2.5 Hz, 1H), 8.27 (dd, J=8.4, 2.4 Hz, 1H), 8.20 (s, 1H), 7.85 (s, 1H), 7.57 (br d, J=8.4 Hz, 1H), 5.42-5.22 (m, 1H), 4.87-4.62 (m, 1H), 4.12-3.29 (m, 4H under water peak), 3.24-3.11 (m, 1H), 2.87-2.71 (m, 4H).

Example 13 (R)—N-cyclopropyl-6-(6-methoxy d3-5-((1-(2-(trifluoromethoxy)phenyl)ethyl)carbamoyl)pyridin-3-yl)-1H-indazole-3-carboxamide Similar protocols used to access 1 were used to afford (R)—N-cyclopropyl-6-(6-methoxy d3-5-((1-(2-(trifluoromethoxy)phenyl)ethyl)carbamoyl)pyridin-3-yl)-1H-indazole-3-carboxamide (6.5 mg, 12 μmol, 29% yield).

MS ESI m/z 543.3 (M+H)

¹H NMR (500 MHz, DMSO-d₆) δ 8.81 (d, J=1.1 Hz, 1H), 8.70 (d, J=2.4 Hz, 1H), 8.45 (d, J=4.4 Hz, 1H), 8.31 (d, J=2.4 Hz, 1H), 8.25 (d, J=8.5 Hz, 1H), 7.84 (s, 1H), 7.69-7.65 (m, 1H), 7.58 (dd, J=8.5, 1.0 Hz, 1H), 7.46-7.39 (m, 2H), 7.36 (dd, J=3.8, 1.7 Hz, 1H), 5.43 (t, J=1.2 Hz, 1H), 2.95-2.85 (m, 1H), 1.47 (d, J=7.0 Hz, 3H), 0.74-0.62 (m, 4H).

Example 14 (R)-6-(6-methoxy d3-5-((1-(3-(trifluoromethoxy)phenyl) ethyl)carbamoyl)pyridin-3-yl)-N-methyl-1H-indazole-3-carboxamide

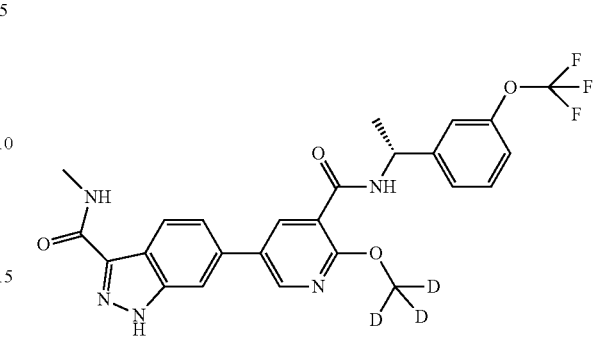

Similar protocols used to access 8 were used to afford (R)-6-(6-methoxy d3-5-((1-(3-(trifluoromethoxy)phenyl) ethyl)carbamoyl)pyridin-3-yl)-N-methyl-1H-indazole-3-carboxamide (25.8 mg, 50 μmol, 26% yield).

MS ESI m/z 517.1 (M+H)

¹H NMR (400 MHz, CD₃OD) δ 8.66 (d, J=2.6 Hz, 1H), 8.49 (d, J=2.6 Hz, 1H), 8.33 (d, J=8.4 Hz, 1H), 7.80 (s, 1H), 7.56 (dd, J=8.5, 1.4 Hz, 1H), 7.52-7.44 (m, 2H), 7.39 (s, 1H), 7.24-7.17 (m, 1H), 5.31 (q, J=7.1 Hz, 1H), 3.00 (s, 3H), 1.62 (d, J=7.1 Hz, 3H).

Example 15 6-(6-methoxy d3-5-((1-(2-(trifluoromethoxy)phenyl) ethyl)carbamoyl)pyridin-3-yl)-N-methyl-1H-indazole-3-carboxamide, homochiral, unknown enantiomer

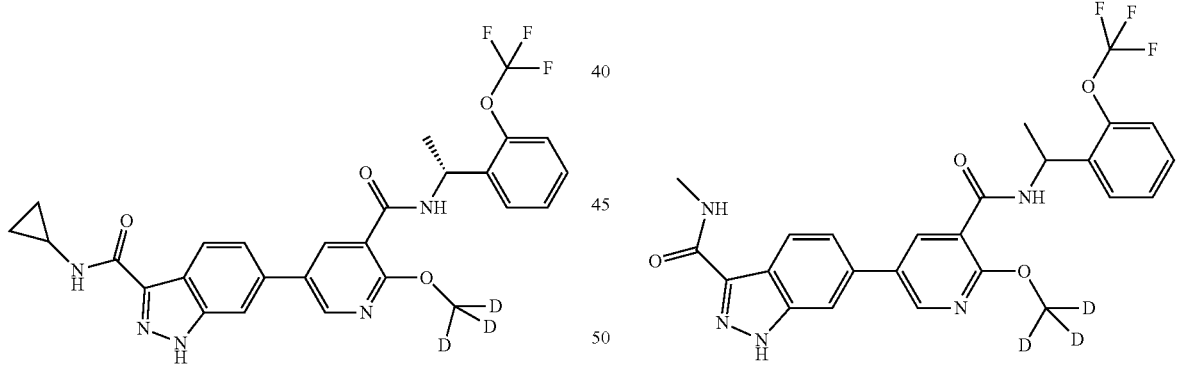

15A: (+/−)-1-(2-(trifluoromethoxy)phenyl)ethanamine, HCl: A solution of 1-(2-(trifluoromethoxy)phenyl)ethanone (3.82 g, 18.71 mmol), ammonium acetate (8.65 g, 112 mmol) and sodium cyanoborohydride (2.94 g, 46.8 mmol) in ethanol (37 mL) was heated to 80° C. for 16 h. The reaction mixture was filtered to remove the solid and the filtrate concentrated. A saturated brine solution (80 mL) was added. The aqueous layer was extracted with ether (50 mL×3). The combined organics were dried over Na₂SO₄. Filtration and concentration yielded a crude product. The crude product was dissolved in ether (100 mL). To the reaction mixture was added HCl 4.0 M in 1,4-dioxane (7.02 mL, 28.1 mmol) and it was stirred for 30 min. The white solid was collected as (+/−)-1-(2-(trifluoromethoxy)phenyl)ethanamine, HCl (1.36 g, 5.63 mmol, 30% yield).

MS ESI m/z 206.1 (M+H)

¹H NMR (400 MHz, CD₃OD) δ 7.66 (dd, J=7.6, 2.0 Hz, 1H), 7.60-7.49 (m, 2H), 7.48-7.44 (m, 1H), 4.84-4.78 (m, 1H), 1.64 (d, J=6.8 Hz, 3H).

15: Similar protocols leading to 1 were used to afford (+/−)-6-(6-methoxy d3-5-((1-(2-(trifluoromethoxy)phenyl)ethyl)carbamoyl)pyridin-3-yl)-N-methyl-1H-indazole-3-carboxamide (123 mg, 0.237 mmol, 65% yield).

MS ESI m/z 517.4 (M+H)

¹H NMR (500 MHz, DMSO-d₆) δ 8.79 (br d, J=7.6 Hz, 1H), 8.67 (s, 1H), 8.38 (br d, J=4.6 Hz, 1H), 8.30 (s, 1H), 8.23 (br d, J=8.5 Hz, 1H), 7.84 (s, 1H), 7.64 (br d, J=4.6 Hz, 1H), 7.56 (br d, J=8.2 Hz, 1H), 7.45-7.30 (m, 3H), 5.41 (br t, J=7.2 Hz, 1H), 2.83 (br d, J=4.3 Hz, 3H), 1.46 (br d, J=7.0 Hz, 3H).

6-(6-methoxy d3-5-((1-(2-(trifluoromethoxy)phenyl)ethyl)carbamoyl)pyridin-3-yl)-N-methyl-1H-indazole-3-carboxamide (123 mg, 0.237 mmol) was separated via preparative SFC with the following conditions: Cellulose-4 (3×25 cm, 5 μm, #637399), BPR pressure: 100 bars, Temperature: 35° C., Flow rate: 200 mL/min, Mobile Phase: CO₂/MeOH (65/35), Detector Wavelength: 220 nm. Fractions from peak 1 were combined to yield 6-(6-methoxy d3-5-((1-(2-(trifluoromethoxy) phenyl) ethyl)carbamoyl) pyridin-3-yl)-N-methyl-1H-indazole-3-carboxamide (26.9 mg, 52.1 μmol, 22.1%. chiral purity: 99.5%).

MS ESI m/z 517.1 (M+H)

¹H NMR (400 MHz, CD₃OD) δ 8.67 (d, J=2.6 Hz, 1H), 8.54 (d, J=2.6 Hz, 1H), 8.33 (d, J=8.6 Hz, 1H), 7.80 (s, 1H), 7.65-7.60 (m, 1H), 7.56 (dd, J=8.6, 1.4 Hz, 1H), 7.43-7.31 (m, 3H), 5.57 (q, J=7.0 Hz, 1H), 3.00 (s, 3H), 1.61 (d, J=7.0 Hz, 3H).

Example 16 6-(6-methoxy D3-5-((2-(trifluoromethoxy)benzyl D2) carbamoyl)pyridin-3-yl)-N-methyl-1H-indazole-3-carboxamide

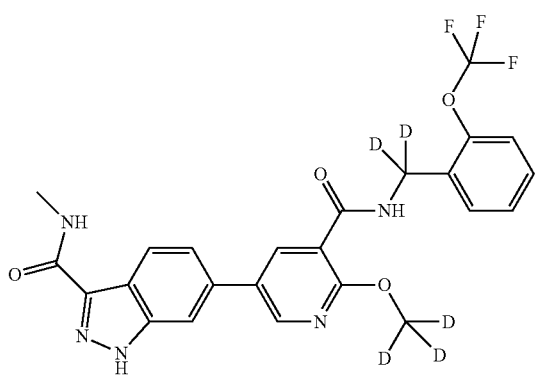 [SMILES: [2H]C([2H])([2H])Oc1ncc(-c2ccc3c(C(=O)NC)n[nH]c3c2)cc1C(=O)NC([2H])([2H])c1ccccc1OC(F)(F)F]

A method substantially similar to that described in 1 was used to afford 6-(6-methoxy D3-5-((2-(trifluoromethoxy) benzyl D2) carbamoyl)pyridin-3-yl)-N-methyl-1H-indazole-3-carboxamide (7.8 mg, 12.6 μmol, 27% yield).

MS ESI m/z 505 (M+H)

¹H NMR (500 MHz, DMSO-d₆) δ 8.92 (s, 1H), 8.73 (d, J=2.1 Hz, 1H), 8.46 (d, J=2.1 Hz, 1H), 8.38 (br d, J=4.6 Hz, 1H), 8.26 (d, J=8.5 Hz, 1H), 7.85 (s, 1H), 7.58 (br d, J=8.5 Hz, 1H), 7.53 (dd, J=7.0, 1.8 Hz, 1H), 7.45-7.36 (m, 3H), 2.84 (d, J=4.6 Hz, 3H).

Example 17 6-(6-methoxy-5-((3-pivalamidocyclohexyl)carbamoyl) pyridin-3-yl)-N-methyl-1H-indazole-3-carboxamide, chiral, unknown isomer

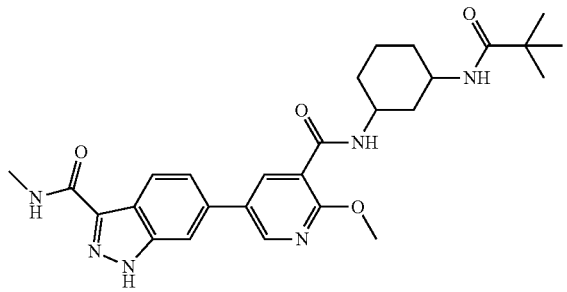 [SMILES: CNC(=O)c1n[nH]c2cc(-c3cnc(OC)c(C(=O)NC4CCCC(NC(=O)C(C)(C)C)C4)c3)ccc12]

17A: tert-butyl (3-(2-methoxy-5-(3-(methylcarbamoyl)-1H-indazol-6-yl)nicotinamido) cyclohexyl)carbamate (diastereomer mixture): To a solution of 2-methoxy-5-(3-(methylcarbamoyl)-1H-indazol-6-yl)nicotinic acid (300 mg, 0.919 mmol), 1-N-Boc-1,3-cyclohexyl diamine (236 mg, 1.10 mmol) and DIPEA (0.482 mL, 2.76 mmol) in DMF (4 mL) was added BOP (488 mg, 1.103 mmol). The reaction mixture was stirred at 23° C. for 1 h. The reaction mixture was concentrated to yield a crude product which was triturated in water (30 mL). The solid was collected as tert-butyl (3-(2-methoxy-5-(3-(methylcarbamoyl)-1H-indazol-6-yl) nicotinamido) cyclohexyl)carbamate (diastereomer mixture)

MS ESI m/z 523.1 (M+H)

17B: 6-(5-((3-aminocyclohexyl)carbamoyl)-6-methoxypyridin-3-yl)-N-methyl-1H-indazole-3-carboxamide, 2 TFA (diastereomer mixture): To a solution of tert-butyl (3-(2-methoxy-5-(3-(methylcarbamoyl)-1H-indazol-6-yl)nicotinamido) cyclohexyl) carbamate (480 mg, 0.918 mmol) in CH₂Cl₂ (5 mL) was added TFA (1.769 mL, 22.96 mmol). The reaction mixture was stirred at 23° C. for 2 h. The reaction mixture was concentrated to yield 6-(5-((3-aminocyclohexyl)carbamoyl)-6-methoxypyridin-3-yl)-N-methyl-1H-indazole-3-carboxamide, 2 TFA (diastereomer mixture, 517 mg, 0.793 mmol, 86% yield).

MS ESI m/z 423.3 (M+H).

17: A method substantially similar to that described in 1 was used to afford 6-(6-methoxy-5-((3-pivalamidocyclohexyl)carbamoyl) pyridin-3-yl)-N-methyl-1H-indazole-3-carboxamide (Diastereomer mixture, 331 mg, 0.653 mmol).

The crude mixture was separated via preparative SFC with the following conditions chiral IC (3×25 cm, 5 um), BPR pressure: 100 bars, temperature: 35° C., flow rate: 250 mL/min, mobile phase: CO₂/MeOH (65/35), detector wavelength: 220 nm. Fractions from peak 3 were combined to yield 6-(6-methoxy-5-((3-pivalamidocyclohexyl)carbamoyl)pyridin-3-yl)-N-methyl-1H-indazole-3-carboxamide (32.7 mg, 65 μm of 9.88%, chiral purity: 92%).

MS ESI m/z 507.4 (M+H)

¹H NMR (500 MHz, DMSO-d₆) δ 8.71 (d, J=2.4 Hz, 1H), 8.40 (br d, J=2.3 Hz, 2H), 8.34 (br d, J=7.2 Hz, 1H), 8.25 (d, J=8.5 Hz, 1H), 7.86 (s, 1H), 7.58 (d, J=8.5 Hz, 1H), 7.17 (br d, J=4.8 Hz, 1H), 4.25 (br s, 1H), 4.08 (s, 3H), 3.99-3.90 (m, 1H), 2.83 (d, J=4.6 Hz, 3H), 1.77 (br d, J=13.0 Hz, 1H), 1.70-1.52 (m, 6H), 1.35 (br d, J=9.5 Hz, 1H), 1.11-1.07 (m, 9H).

Example 18 6-(6-methoxy-5-(2-(1-phenylpropyl)-2H-tetrazol-5-yl)pyridin-3-yl)-N-methyl-1H-indazole-3-carboxamide, homochiral, unknown enantiomers

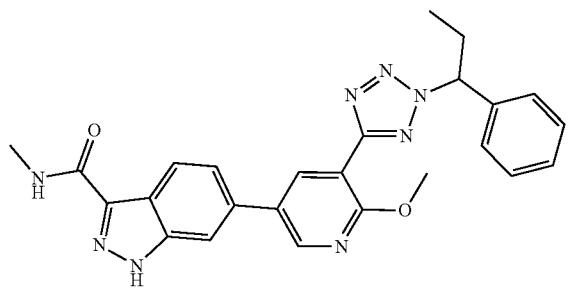 [SMILES: CCC(c1ccccc1)n1nnc(-c2cc(-c3ccc4c(C(=O)NC)n[nH]c4c3)cnc2OC)n1]

18A: (rac)-(1-bromopropyl)benzene: A solution of 1-phenylpropan-1-ol (0.5 g, 3.67 mmol) and phosphorus tribromide (0.693 mL, 7.34 mmol) in CHCl₃ (10 mL) was heated at 70° C. for 16 h. The reaction mixture was quenched with ice (20 mL) and diluted with ethyl acetate (100 mL). The organic layer was separated and washed with water (20 mL) followed by brine (20 mL). The organics were dried over anhydrous sodium sulfate and concentrated in vacuo to obtain the crude product which was purified using silica gel chromatography with Hexanes/CH₂Cl₂ (4/1) to afford (rac)-(1-bromopropyl)benzene (540 mg, 2.71 mmol, 74% yield).

¹H NMR (400 MHz, CDCl₃) δ 7.45-7.29 (m, 5H), 4.91 (dd, J=7.9, 7.0 Hz, 1H), 2.41-2.12 (m, 2H), 1.03 (t, J=7.2 Hz, 3H).

18B: 5-bromo-2-methoxy-3-(1H-tetrazol-5-yl)pyridine: A solution of 5-bromo-2-methoxynicotinonitrile (1.09 g, 5.12 mmol) and azidotributyltin (1.402 mL, 5.12 mmol) in DMF (15 mL) was heated to 150° C. for 2.5 h under microwave. The reaction mixture was concentrated and diluted with a mixture of MeOH (19 mL)/water (13.5 mL)/HOAc (5.5 mL). A white solid precipitated. The mixture was stirred at rt for 1 h. The solid was collected and triturated in toluene (10 mL). The white solid was collected as 5-bromo-2-methoxy-3-(1H-tetrazol-5-yl)pyridine (1.172 g, 4.45 mmol, 87% yield).

MS ESI m/z 256.0 (M+H)

¹H NMR (400 MHz, DMSO-d₆) δ 8.57-8.53 (m, 2H), 4.04 (s, 3H). 18C: (rac)-(5-bromo-2-methoxy-3-(2-(l-phenylpropyl)-2H-tetrazol-5-yl)pyridine: A solution of 5-bromo-2-methoxy-3-(1H-tetrazol-5-yl)pyridine (300 mg, 1.172 mmol), (+/−)-(1-bromopropyl)benzene (292 mg, 1.465 mmol) and K₂CO₃ (243 mg, 1.757 mmol) in DMF (8 mL) was stirred at 23° C. for 24 h. The reaction mixture was concentrated and diluted with EtOAc (100 mL). The organics were washed with 10% LiCl solution (30 mL), brine (30 mL) and dried over Na₂SO₄. Filtration and concentration yielded a crude product which was purified using silica gel chromatography with Hexanes/EtOAc (2/1) to yield (rac)-(5-bromo-2-methoxy-3-(2-(l-phenylpropyl)-2H-tetrazol-5-yl)pyridine (286.7 mg, 0.738 mmol, 63% yield).

MS ESI m/z 374.0 (M+H)

¹H NMR (400 MHz, CDCl₃) δ 8.41 (d, J=2.6 Hz, 1H), 8.33 (d, J=2.4 Hz, 1H), 7.54-7.47 (m, 2H), 7.43-7.31 (m, 3H), 5.87 (dd, J=8.9, 6.8 Hz, 1H), 4.08 (s, 3H), 2.76-2.57 (m, 1H), 2.50-2.30 (m, 1H), 0.98 (t, J=7.3 Hz, 3H).

18D: (rac)-2-methoxy-3-(2-(l-phenylpropyl)-2H-tetrazol-5-yl)-5-(4,4,5,5-tetramethyl-1,3,2-dioxaborolan-2-yl)pyridine: A degassed solution of (rac)-5-bromo-2-methoxy-3-(2-(l-phenylpropyl)-2H-tetrazol-5-yl)pyridine (276 mg, 0.738 mmol), bis(pinacolato)diboron (225 mg, 0.885 mmol), potassium acetate (109 mg, 1.106 mmol) and 1,1'-bis(diphenylphosphino)ferrocene-palladium(II) dichloride dichloromethane complex (60.2 mg, 0.074 mmol) in dioxane (5 mL) was heated to 80° C. for 16 h. The reaction mixture was concentrated and purified on a silica gel column with Hexanes/EtOAc (100/0 to 60/40) to yield (rac)-2-methoxy-3-(2-(l-phenylpropyl)-2H-tetrazol-5-yl)-5-(4,4,5,5-tetramethyl-1,3,2-dioxaborolan-2-yl)pyridine (312 mg, 0.741 mmol, 100% yield).

MS ESI m/z 422.1 (M+H)

¹H NMR (400 MHz, CD₃OD) δ 8.60 (d, J=1.8 Hz, 1H), 8.54 (d, J=1.8 Hz, 1H), 7.56-7.50 (m, 2H), 7.45-7.28 (m, 3H), 6.01 (dd, J=8.9, 6.6 Hz, 1H), 4.08 (s, 3H), 2.76-2.26 (m, 2H), 1.39 (s, 12H), 0.97 (t, J=7.3 Hz, 3H).

18E: tert-butyl 6-bromo-3-(methylcarbamoyl)-1H-indazole-1-carboxylate: Similar protocols leading to 1G were used to afford tert-butyl 6-bromo-3-(methyl carbamoyl)-1H-indazole-1-carboxylate (346 mg, 0.978 mmol, 34% yield).

MS ESI m/z 354.1 (M+H)

18: (rac)-6-(6-methoxy-5-(2-(l-phenylpropyl)-2H-tetrazol-5-yl)pyridin-3-yl)-N-methyl-1H-indazole-3-carboxamide: A degassed solution of tert-butyl 6-bromo-3-(methylcarbamoyl)-1H-indazole-1-carboxylate (130 mg, 0.367 mmol), 2-methoxy-3-(2-(l-phenylpropyl)-2H-tetrazol-5-yl)-5-(4,4,5,5-tetramethyl-1,3,2-dioxaborolan-2-yl)pyridine (155 mg, 0.367 mmol), PdCl₂(dppf)-CH₂Cl₂ adduct (17.98 mg, 0.022 mmol) and potassium phosphate tribasic 2M solution (0.551 mL, 1.101 mmol) in DMF (2 mL) was heated to 100° C. for 2 h. The reaction mixture was concentrated and purified on a Combiflash RF200 with Column: 100 g C18 RediSep Rf High performance Gold, solvent A: 0.1% TFA in water/MeOH (90/10), solvent B: 0.1% TFA in water/MeOH (10/90), flow rate: 60 mL/min., start % B: 10%, final % B: 100%, wavelength 1: 254, wavelength 1: 220 to yield (rac)-6-(6-methoxy-5-(2-(l-phenylpropyl)-2H-tetrazol-5-yl)pyridin-3-yl)-N-methyl-1H-indazole-3-carboxamide (92.7 mg, 0.198 mmol, 54% yield).

MS ESI m/z 469.0 (M+H)

¹H NMR (400 MHz, DMSO-d₆) δ 7.85 (d, J=2.6 Hz, 1H), 7.80 (d, J=2.4 Hz, 1H), 7.53 (dd, J=8.5, 0.7 Hz, 1H), 7.03 (s, 1H), 6.78 (dd, J=8.4, 1.5 Hz, 1H), 6.76-6.72 (m, 2H), 6.65-6.53 (m, 3H), 5.23 (dd, J=8.9, 6.7 Hz, 1H), 3.32 (s, 3H), 2.20 (s, 3H), 1.95-1.81 (m, 1H), 1.65 (dt, J=14.2, 6.9 Hz, 1H), 0.18 (t, J=7.3 Hz, 3H).

The material was separated via preparative SFC with the following conditions: chiralcel OJ-H (3×25 cm, 5 μm), BPR pressure: 100 bars, temperature: 40° C., flow rate: 160 mL/min, mobile Phase: CO₂/MeOH w 0.1% NH4OH (78/22), detector wavelength: 250 nm.

18-1: Fractions from peak 1 were combined to yield 6-(6-methoxy-5-(2-(l-phenylpropyl)-2H-tetrazol-5-yl)pyridin-3-yl)-N-methyl-1H-indazole-3-carboxamide (a) (32 mg, 0.068 mmol, 35%, chiral purity: 99.5%).

MS ESI m/z 469.1 (M+H)

¹H NMR (400 MHz, CD₃OD) δ 8.66 (d, J=2.4 Hz, 1H), 8.61 (d, J=2.6 Hz, 1H), 8.35 (d, J=8.7 Hz, 1H), 7.84 (s, 1H), 7.62-7.53 (m, 3H), 7.45-7.35 (m, 3H), 6.04 (dd, J=9.0, 6.7 Hz, 1H), 4.13 (s, 3H), 3.01 (s, 3H), 2.74-2.64 (m, 1H), 2.52-2.40 (m, 1H), 0.99 (t, J=7.3 Hz, 3H).

18-2: Fractions from peak 2 were combined to yield 6-(6-methoxy-5-(2-(l-phenylpropyl)-2H-tetrazol-5-yl)pyridin-3-yl)-N-methyl-1H-indazole-3-carboxamide (b) (32 mg, 0.068 mmol, 35%, chiral purity: 99.4%).

MS ESI m/z 469.1 (M+H)

¹H NMR (400 MHz, DMSO-d₆) δ 8.77 (d, J=2.6 Hz, 1H), 8.57 (d, J=2.6 Hz, 1H), 8.37 (q, J=4.4 Hz, 1H), 8.26 (d, J=8.4 Hz, 1H), 7.89 (s, 1H), 7.61 (dd, J=8.6, 1.5 Hz, 1H), 7.55-7.49 (m, 2H), 7.46-7.34 (m, 3H), 6.17 (dd, J=8.8, 6.6 Hz, 1H), 4.03 (s, 3H), 2.84 (d, J=4.8 Hz, 3H), 2.62-2.50 (m, 1H merge with DMSO), 2.41-2.29 (m, 1H), 0.90 (t, J=7.2 Hz, 3H).

Example 19 6-(5-(2-(1-(4-fluorophenyl)ethyl)-2H-tetrazol-5-yl)-6-methoxypyridin-3-yl)-N-(methyl-d3)-1H-indazole-3-carboxamide, homochiral, unknown enantiomers

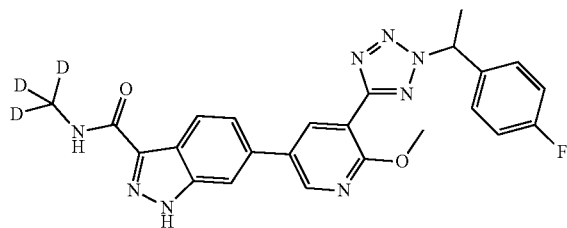 [SMILES: [2H]C([2H])([2H])NC(=O)c1n[nH]c2cc(-c3cnc(OC)c(-c4nnn(C(C)c5ccc(F)cc5)n4)c3)ccc12]

19A: 6-bromo-N-(methyl-d3)-1H-indazole-3-carboxamide: Similar protocols leading to 1F were used to afford 6-bromo-N-(methyl-d3)-1H-indazole-3-carboxamide (231 mg, 0.895 mmol).
MS ESI m/z 257.1 (M+H)

19B: tert-butyl 6-bromo-3-((methyl-d3)carbamoyl)-1H-indazole-1-carboxylate: Similar protocols leading to 1G were used to afford tert-butyl 6-bromo-3-((methyl-d3)carbamoyl)-1H-indazole-1-carboxylate (149 mg, 0.414 mmol, 79% yield).
MS ESI m/z 357.0 (M+H)
¹H NMR (400 MHz, CD₃OD) δ 8.43-8.37 (m, 1H), 8.26-8.19 (m, 1H), 7.61 (dd, J=8.6, 1.6 Hz, 1H), 1.76 (s, 9H).

19C: 6-(5-cyano-6-methoxypyridin-3-yl)-N-(methyl-d3)-1H-indazole-3-carboxamide: A method substantially similar to that described in 1 L was used to afford 6-(5-cyano-6-methoxypyridin-3-yl)-N-(methyl-d3)-1H-indazole-3-carboxamide (97 mg, 0.305 mmol, 73% yield).
MS ESI m/z 311.1 (M+H)

19D: 6-(6-methoxy-5-(1H-tetrazol-5-yl)pyridin-3-yl)-N-(methyl-d3)-1H-indazole-3-carboxamide: A method substantially similar to that described in 18B was used to afford 6-(6-methoxy-5-(1H-tetrazol-5-yl)pyridin-3-yl)-N-(methyl-d3)-1H-indazole-3-carboxamide (32 mg, 0.091 mmol, 29% yield).
MS ESI m/z 354.1 (M+H)

19E: (+/−)-6-(5-(2-(1-(4-fluorophenyl)ethyl)-2H-tetrazol-5-yl)-6-methoxypyridin-3-yl)-N-(methyl-d3)-1H-indazole-3-carboxamide: A method substantially similar to that described in 18C was used to afford (+/−)-6-(5-(2-(1-(4-fluorophenyl)ethyl)-2H-tetrazol-5-yl)-6-methoxypyridin-3-yl)-N-(methyl-d3)-1H-indazole-3-carboxamide (16 mg, 0.033 mmol, 37% yield).
MS ESI m/z 476.1 (M+H).

19-1: A method substantially similar to that described in 18O was used to afford 6-(5-(2-(1-(4-fluorophenyl)ethyl)-2H-tetrazol-5-yl)-6-methoxypyridin-3-yl)-N-(methyl-d3)-1H-indazole-3-carboxamide PK1 (a) (2.1 mg, 0.0042 mmol, 13% yield).
MS ESI m/z 476.1 (M+H)
¹H NMR (400 MHz, CDCl₃) δ 10.41 (br s, 1H), 8.57 (q, J=2.5 Hz, 2H), 8.51 (d, J=8.4 Hz, 1H), 7.66 (s, 1H), 7.56 (dd, J=8.5, 1.3 Hz, 1H), 7.50-7.44 (m, 2H), 7.14-7.00 (m, 3H), 6.18 (q, J=1.2 Hz, 1H), 4.15 (s, 3H), 2.15 (d, J=1.1 Hz, 3H).

19-2: PK2 (b): 6-(5-(2-(1-(4-fluorophenyl)ethyl)-2H-tetrazol-5-yl)-6-methoxypyridin-3-yl)-N-(methyl-d3)-1H-indazole-3-carboxamide PK2(b) (4.6 mg, 0.0097 mmol, 29% yield).
MS ESI m/z 476.1 (M+H)
¹H NMR (400 MHz, CD3OD) δ 8.65 (d, J=2.6 Hz, 1H), 8.59 (d, J=2.6 Hz, 1H), 8.33 (dd, J=8.4, 0.6 Hz, 1H), 7.82 (s, 1H), 7.61-7.51 (m, 3H), 7.19-7.12 (m, 2H), 6.32 (q, J=7.1 Hz, 1H), 4.11 (s, 3H), 2.12 (d, J=1.1 Hz, 3H).

Example 20 6-[5-(2-benzyl-2H-1,2,3,4-tetrazol-5-yl)-6-methoxypyridin-3-yl]-N-methyl-1H-indazole-3-carboxamide

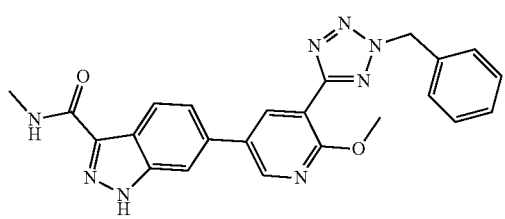 [SMILES: CNC(=O)c1n[nH]c2cc(-c3cnc(OC)c(-c4nnn(Cc5ccccc5)n4)c3)ccc12]

Similar protocols leading to 19 were used to afford 6-[5-(2-benzyl-2H-1,2,3,4-tetrazol-5-yl)-6-methoxypyridin-3-yl]-N-methyl-1H-indazole-3-carboxamide (6.0 mg, 0.013 mmol, 19c % yield).
MS ESI m/z 441.2 (M+H)
¹H NMR (500 MHz, DMSO-d₆) δ 13.69 (s, 1H), 8.75 (s, 1H), 8.56 (s, 1H), 8.41 (br d, J=4.5 Hz, 1H), 8.26 (br d, J=8.3 Hz, 1H), 7.89 (s, 1H), 7.61 (br d, J=8.4 Hz, 1H), 7.47-7.33 (m, 5H), 6.04 (s, 2H), 4.01 (s, 3H), 2.83 (br d, J=4.4 Hz, 3H).

Example 21 6-{6-methoxy-5-[(3-phenylcyclohexyl)carbamoyl]pyridin-3-yl}-N-methyl-1H-indazole-3-carboxamide, homochiral, Unknown Isomers

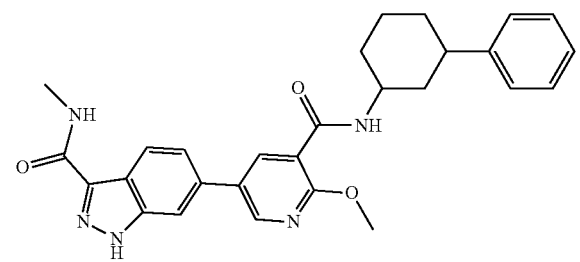 [SMILES: CNC(=O)c1n[nH]c2cc(-c3cnc(OC)c(C(=O)NC4CCCC(c5ccccc5)C4)c3)ccc12]

21A: 2-methoxy-5-(3-(methylcarbamoyl)-1H-indazol-6-yl)nicotinic acid: Similar protocols leading to 1H were used to afford 2-methoxy-5-(3-(methylcarbamoyl)-1H-indazol-6-yl)nicotinic acid (735 mg, 2.072 mmol, 96% yield).
MS ESI m/z 327.1 (M+H)

21: A method substantially similar to that described in 1 was used to afford 6-{6-methoxy-5-[(3-phenylcyclohexyl)carbamoyl]pyridin-3-yl}-N-methyl-1H-indazole-3-carboxamide (diastereomer mixture, 251 mg, 0.510 mmol, 83% yield). The crude mixture was separated via preparative SFC with the following conditions chiralpak OD (3×25 cm, 5 μm), BPR pressure: 100 bars, temperature: 40° C., flow rate: 170 mL/min, mobile Phase: CO₂/MeOH (68/32), detector wavelength: 220 nm.

21-1: Fractions from peak 1 were combined to yield 6-{6-methoxy-5-[(3-phenylcyclohexyl)carbamoyl]pyridin- 3-yl}-N-methyl-1H-indazole-3-carboxamide (78 mg, 158 µmol, 30%, chiral purity: 98.7%).

MS ESI m/z 484.1 (M+H)

¹H NMR (400 MHz, DMSO-d₆) δ 13.65 (br s, 1H), 8.72 (d, J=2.6 Hz, 1H), 8.44-8.34 (m, 3H), 8.26 (d, J=8.4 Hz, 1H), 7.86 (s, 1H), 7.59 (dd, J=8.5, 1.4 Hz, 1H), 7.35-7.25 (m, 4H), 7.23-7.15 (m, 1H), 4.37-4.26 (m, 1H), 4.10 (s, 3H), 2.96-2.80 (m, 4H), 2.02-1.47 (m, 8H).

21-2: Fractions from peak 3 were combined to yield 6-{6-methoxy-5-[(3-phenylcyclohexyl)carbamoyl] pyridin-3-yl}-N-methyl-1H-indazole-3-carboxamide (11.4 mg, 24 µmol, 4.5%, chiral purity: 99.5%).

MS ESI m/z 484.1 (M+H)

¹H NMR (400 MHz, DMSO-d₆) δ 13.64 (br s, 1H), 8.68 (d, J=2.6 Hz, 1H), 8.40-8.32 (m, 2H), 8.27-8.22 (m, 1H), 8.19 (d, J=7.8 Hz, 1H), 7.83 (s, 1H), 7.57 (dd, J=8.5, 1.4 Hz, 1H), 7.36-7.24 (m, 4H), 7.23-7.16 (m, 1H), 4.02 (s, 3H), 3.97 (dq, J=11.7, 3.9 Hz, 1H), 2.83 (d, J=4.8 Hz, 3H), 2.75-2.65 (m, 1H), 2.09-1.95 (m, 2H), 1.93-1.85 (m, 1H), 1.83-1.76 (m, 1H), 1.58-1.32 (m, 4H).

21-3: Fractions from peak 2 were combined to yield 6-{6-methoxy-5-[(3-phenylcyclohexyl)carbamoyl] pyridin-3-yl}-N-methyl-1H-indazole-3-carboxamide (63 mg, 130 µmol, 25%, chiral purity: 98.7%).

MS ESI m/z 484.1 (M+H)

¹H NMR (400 MHz, DMSO-d₆) δ 13.65 (s, 1H), 8.72 (d, J=2.6 Hz, 1H), 8.44-8.34 (m, 3H), 8.26 (d, J=8.6 Hz, 1H), 7.86 (s, 1H), 7.59 (dd, J=8.5, 1.4 Hz, 1H), 7.35-7.25 (m, 4H), 7.22-7.15 (m, 1H), 4.36-4.28 (m, 1H), 4.11 (s, 3H), 2.84 (d, J=4.8 Hz, 4H), 2.01-1.47 (m, 8H).

21-4: Fractions from peak 4 were combined to yield 6-{6-methoxy-5-[(3-phenylcyclohexyl)carbamoyl] pyridin-3-yl}-N-methyl-1H-indazole-3-carboxamide (8.4 mg, 17 µmol, 3.4%, chiral purity: 92.6%).

MS ESI m/z 484.1 (M+H)

¹H NMR (400 MHz, DMSO-d₆) δ 13.64 (br s, 1H), 8.68 (d, J=2.6 Hz, 1H), 8.43-8.31 (m, 2H), 8.27-8.22 (m, 1H), 8.19 (d, J=1.1 Hz, 1H), 7.83 (s, 1H), 7.57 (dd, J=8.6, 1.5 Hz, 1H), 7.35-7.24 (m, 4H), 7.23-7.16 (m, 1H), 4.02 (s, 3H), 4.00-3.91 (m, 1H), 2.83 (d, J=4.8 Hz, 3H), 2.76-2.65 (m, 1H), 2.10-1.94 (m, 2H), 1.93-1.85 (m, 1H), 1.83-1.76 (m, 1H), 1.59-1.10 (m, 4H).

Example 22 (rac)-N-isopropyl-6-(6-methoxy d3-5-((1-(2-(trifluoromethoxy)phenyl)ethyl)carbamoyl) pyridin-3-yl)-1H-indazole-3-carboxamide

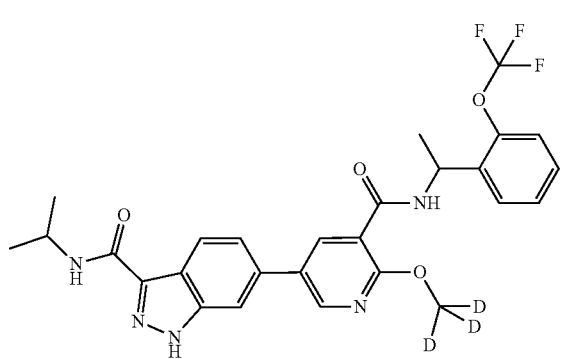 [SMILES: [2H]C([2H])([2H])Oc1ncc(-c2ccc3c(C(=O)NC(C)C)n[nH]c3c2)cc1C(=O)NC(C)c1ccccc1OC(F)(F)F]

22A: 5-(3-(isopropylcarbamoyl)-1H-indazol-6-yl)-2-methoxy d3-nicotinic acid: Similar protocols leading to 1H were used to afford 5-(3-(isopropylcarbamoyl)-1H-indazol-6-yl)-2-methoxy d3-nicotinic acid (273 mg).

MS ESI m/z 358.2 (M+H)

22: A method substantially similar to that described in 1 was used to afford (rac)-N-isopropyl-6-(6-methoxy d3-5-((1-(2-(trifluoromethoxy)phenyl)ethyl)carbamoyl)pyridin-3-yl)-1H-indazole-3-carboxamide (5.1 mg, 8.99 µmol, 21% yield).

MS ESI m/z 545.1 (M+H)

¹H NMR (500 MHz, DMSO-d₆) δ 8.79 (br d, J=7.3 Hz, 1H), 8.69 (d, J=2.1 Hz, 1H), 8.31 (d, J=1.8 Hz, 1H), 8.24 (br d, J=8.2 Hz, 1H), 8.10 (br d, J=8.2 Hz, 1H), 7.84 (s, 1H), 7.70-7.62 (m, 1H), 7.56 (br d, J=8.5 Hz, 1H), 7.45-7.28 (m, 4H), 5.48-5.36 (m, 1H), 4.18 (dq, J=13.7, 6.5 Hz, 1H), 1.47 (br d, J=7.0 Hz, 3H), 1.21 (br d, J=6.7 Hz, 6H).

Example 23 N-(4-(dimethyl d6-amino)cyclohexyl)-6-(6-methoxy d3-5-((1-(3-(trifluoromethoxy)phenyl) ethyl)carbamoyl)pyridin-3-yl)-1H-indazole-3-carboxamide (Diastereomer Mixture)

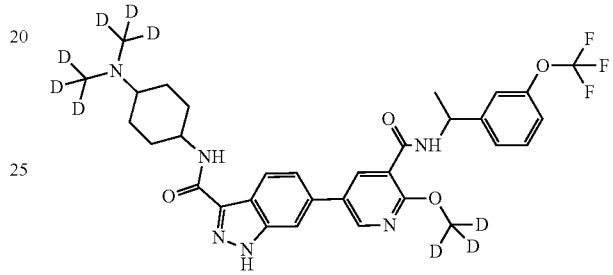

23A: tert-butyl (4-(bis(methyl-d3)amino)cyclohexyl)carbamate (diastereomer mixture): To a solution of N-4-Boc-aminocyclohexanone (100 mg, 0.469 mmol), dimethyl d6-amine (103 mg, 1.172 mmol) and triethylamine (0.163 mL, 1.172 mmol) in MeOH (2 mL) and THF (2 mL) at 23° C. was added sodium cyanoborohydride (73.7 mg, 1.172 mmol). The reaction mixture was stirred for 16 h and concentrated. The residue was partitioned between EtOAc (30 mL) and aqueous saturated sodium bicarbonate solution (20 mL). The organic layer was washed with brine (20 mL) and dried over anhydrous sodium sulfate. The dried solution was filtered, and the filtrate was concentrated in vacuo to yield tert-butyl (4-(bis(methyl-d3)amino)cyclohexyl)carbamate (diastereomer mixture, 93 mg, 372 µmol, 79% yield).

MS ESI m/z 249.4 (M+H)

23B: N1,N1-bis(methyl-d3)cyclohexane-1,4-diamine (diastereomer mixture): A solution of tert-butyl (4-(dimethyl d6-amino)cyclohexyl)carbamate (92.5 mg, 0.372 mmol) and TFA (0.717 mL, 9.31 mmol) in CH₂Cl₂ (2 mL) was stirred at 23° C. for 1 h. The reaction mixture was concentrated to yield N1,N1-bis(methyl-d3)cyclohexane-1,4-diamine (diastereomer mixture, 148 mg, 393 µmol, 100% yield).

23C: 5-(3-((4-(bis(methyl-d3)amino)cyclohexyl)carbamoyl)-1H-indazol-6-yl)-2-(methoxy-d3)nicotinic acid (diastereomer mixture): Similar protocols leading to 1H were used to afford 5-(3-((4-(bis(methyl-d3)amino)cyclohexyl)carbamoyl)-1H-indazol-6-yl)-2-(methoxy-d3)nicotinic acid (diastereomer mixture, 93 mg).

MS ESI m/z 447.1 (M+H)

23: A method substantially similar to that described in 1 was used to afford N-(4-(bis(methyl-d3)amino)cyclohexyl)-6-(6-(methoxy-d3)-5-((1-(3-(trifluoromethoxy)phenyl) ethyl)carbamoyl) pyridin-3-yl)-1H-indazole-3-carboxamide (diastereomer mixture, 4.4 mg, 6.80 µmol, 17% yield).

MS ESI m/z 634.3 (M+H)

¹H NMR (500 MHz, DMSO-d₆) δ 8.79 (br d, J=7.6 Hz, 1H), 8.70 (s, 1H), 8.36-8.04 (m, 3H), 7.87 (br d, J=7.0 Hz, 1H), 7.63-7.56 (m, 3H), 7.53-7.42 (m, 3H), 7.25 (br d, J=7.3 Hz, 1H), 5.21 (br t, J=7.2 Hz, 1H), 4.27-3.82 (m, 1H), 2.10-1.93 (m, 3H), 1.90-1.76 (m, 2H), 1.76-1.44 (m, 7H).

Example 24 4-fluoro-6-[6-methoxy-5-({1-[2-(trifluoromethoxy)phenyl]ethyl}carbamoyl)pyridin-3-yl]-N-methyl-1H-indazole-3-carboxamide

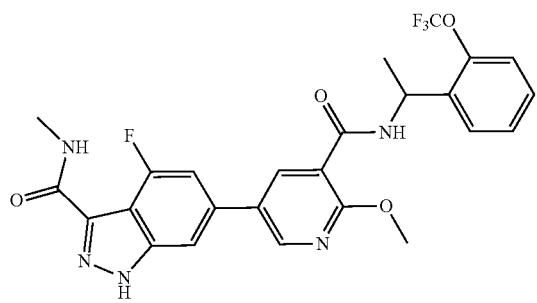 [SMILES: CNC(=O)c1n[nH]c2cc(-c3cnc(OC)c(C(=O)NC(C)c4ccccc4OC(F)(F)F)c3)cc(F)c12]

A method substantially similar to that described in 1 was used to afford 4-fluoro-6-[6-methoxy-5-({1-[2-(trifluoromethoxy)phenyl]ethyl}carbamoyl)pyridin-3-yl]-N-methyl-1H-indazole-3-carboxamide (racemate, 6.3 mg, 11 μmol, 34% yield).

MS ESI m/z 532.3 (M+H)

$^1$H NMR (500 MHz, DMSO-d$_6$) δ 8.80 (br d, J=7.6 Hz, 1H), 8.72 (d, J=1.8 Hz, 1H), 8.38 (br d, J=4.6 Hz, 1H), 8.32 (d, J=1.8 Hz, 1H), 7.70 (s, 1H), 7.67-7.63 (m, 1H), 7.46-7.33 (m, 4H), 5.47-5.36 (m, 1H), 4.04 (s, 3H), 2.82 (d, J=4.6 Hz, 3H), 1.47 (d, J=7.0 Hz, 3H).

TABLE 1

Compounds in Table 1 were made in a similar fashion to example 1. Non-delineated stereochemistry is racemic unless otherwise noted in the text.

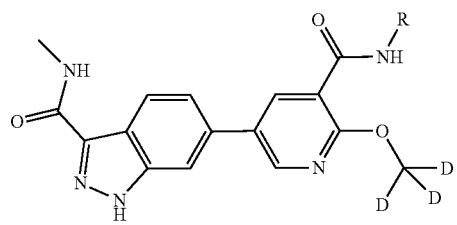

| Ex | Name | R | M + H |
|----|------|---|-------|
| 25 | 6-[6-(deutero)methoxy-5-{[(1S)-1-[3-trifluoromethoxy)phenyl]-ethyl]carbamoyl}pyridin-3-yl]-N-methyl-1H-indazole-3-carboxamide | (S)-1-[3-(trifluoromethoxy)phenyl]ethyl | 517.1 |
| 26 | tert-butyl 3-{[2-(deutero)methoxy-5-[3-(methylcarbamoyl)-1H-indazol-6-yl]pyridin-3-yl]formamido}propanoate | -CH₂CH₂C(O)O-tBu | 457.2 |
| 27 | 6-(5-{[(3S)-3-(4-chlorophenyl)-3-hydroxypropyl]carbamoyl}-6-(deutero)methoxypyridin-3-yl)-N-methyl-1H-indazole-3-carboxamide, TFA | (S)-3-(4-chlorophenyl)-3-hydroxypropyl | 497.3 |
| 28 | tert-butyl 3-{[2-(deutero)methoxy-5-[3-(methylcarbamoyl)-1H-indazol-6-yl]pyridin-3-yl]formamido}-2,2-dimethylpropanoate, TFA | -CH₂C(CH₃)₂C(O)O-tBu | 485.1 |
| 29 | tert-butyl (3R)-3-{[2-(deutero)methoxy-5-[3-(methylcarbamoyl)-1H-indazol-6-yl]pyridin-3-yl]formamido}butanoate | (R)-CH(CH₃)CH₂C(O)O-tBu | 471.4 |

TABLE 1-continued

Compounds in Table 1 were made in a similar fashion to example 1. Non-delineated stereochemistry is racemic unless otherwise noted in the text.

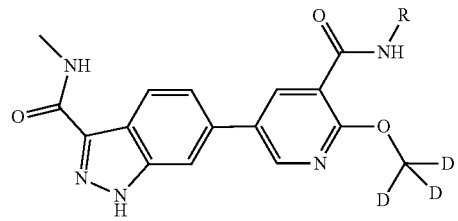

| Ex | Name | R | M + H |
|---|---|---|---|
| 30 | 6-(5-{[(1R)-1-[2-fluoro-5-(trifluoromethoxy)phenyl]ethyl]-carbamoyl}-6-(deutero)methoxypyridin-3-yl)-N-methyl-1H-indazole-3-carboxamide | 2-F, 5-OCF₃ phenyl (1R) | 535.2 |
| 31 | 6-(5-{[(1R)-1-[2-fluoro-5-(trifluoromethyl)phenyl]ethyl]-carbamoyl}-6-(deutero)methoxypyridin-3-yl)-N-methyl-1H-indazole-3-carboxamide | 2-F, 5-CF₃ phenyl (1R) | 519.1 |
| 32 | 6-(5-{[(1S)-1-[2-fluoro-5-(trifluoromethyl)phenyl]ethyl]-carbamoyl}-6-(deutero)methoxypyridin-3-yl)-N-methyl-1H-indazole-3-carboxamide | 2-F, 5-CF₃ phenyl (1S) | 519.3 |
| 33 | 6-[6-(deutero)methoxy-5-{[(1R)-1-[2-(trifluoromethyl)phenyl]-ethyl]carbamoyl}pyridin-3-yl]-N-methyl-1H-indazole-3-carboxamide | 2-CF₃ phenyl (1R) | 501.2 |
| 34 | 6-[6-(deutero)methoxy-5-{[(1R)-1-[3-(trifluoromethyl)phenyl]-ethyl]carbamoyl}pyridin-3-yl]-N-methyl-1H-indazole-3-carboxamide | 3-CF₃ phenyl (1R) | 501.2 |
| 35 | 6-[6-(deutero)methoxy-5-{[(1S)-1-[3-(trifluoromethyl)phenyl]-ethyl]carbamoyl}pyridin-3-yl]-N-methyl-1H-indazole-3-carboxamide | 3-CF₃ phenyl (1S) | 501.0 |
| 36 | 6-[5-({1-[5-fluoro-2-(trifluoromethyl)phenyl]ethyl}carbamoyl)-6-(deutero)methoxypyridin-3-yl]-N-methyl-1H-indazole-3-carboxamide | 5-F, 2-CF₃ phenyl | 519.0 |

TABLE 2

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|---|---|---|---|
| 37 | 6-{6-methoxy-5-[(3-phenylbutyl)-carbamoyl]pyridin-3-yl}-N-methyl-1H-indazole-3-carboxamide | | 461.3 |
| 38 | 6-(5-{[3-hydroxy-3-(4-methoxyphenyl)propyl]carbamoyl}-6-methoxypyridin-3-yl)-N-methyl-1H-indazole-3-carboxamide | | 490.3 |
| 39 | 6-(5-{[3-(3,4-difluorophenyl)-3-hydroxypropyl]carbamoyl}-6-methoxypyridin-3-yl)-N-methyl-1H-indazole-3-carboxamide | | 496.4 |
| 40 | 6-(5-{[3-(4-fluorophenyl)-3-hydroxypropyl]carbamoyl}-6-methoxypyridin-3-yl)-N-methyl-1H-indazole-3-carboxamide | | 478.0 |
| 41 | 6-(5-{[3-(4-fluorophenyl)-butyl]carbamoyl}-6-methoxy-pyridin-3-yl)-N-methyl-1H-indazole-3-carboxamide | | 476.0 |
| 42 | 6-[5-({[2-(3-fluorophenyl)cyclopropyl]methyl}carbamoyl)-6-methoxypyridin-3-yl]-N-methyl-1H-indazole-3-carboxamide | | 474.1 |
| 43 | 6-[5-({[(1S,2S)-2-(4-fluorophenyl)cyclopropyl]methyl}-carbamoyl)-6-methoxypyridin-3-yl]-N-methyl-1H-indazole-3-carboxamide, homochiral | | 474.0 |
| 44 | 6-[5-({[(1S,2S)-2-(4-fluorophenyl)cyclopropyl]methyl}-carbamoyl)-6-methoxypyridin-3-yl]-N-methyl-1H-indazole-3-carboxamide, homochiral | | 474.0 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|----|------|---|-------|
| 45 | 6-(6-methoxy-5-{[(1R,2S)-2-phenylcyclopropyl]carbamoyl}-pyridin-3-yl)-N-methyl-1H-indazole-3-carboxamide | | 442.0 |
| 46 | 6-(6-methoxy-5-{[(1S,2R)-2-phenylcyclopropyl]carbamoyl}-pyridin-3-yl)-N-methyl-1H-indazole-3-carboxamide | | 442.0 |
| 47 | 6-(6-methoxy-5-{[2-(phenylsulfamoyl)ethyl]carbamoyl}-pyridin-3-yl)-N-methyl-1H-indazole-3-carboxamide | | 509.0 |
| 48 | 6-[5-({[2-(3-fluorophenyl)-cyclopropyl]methyl}carbamoyl)-6-methoxypyridin-3-yl]-N-methyl-1H-indazole-3-carboxamide, cis, homochiral | | 474.3 |
| 49 | 6-[5-({[2-(3-fluorophenyl)-cyclopropyl]methyl}carbamoyl)-6-methoxypyridin-3-yl]-N-methyl-1H-indazole-3-carboxamide, cis, homochiral | | 474.1 |
| 50 | 6-[5-({[4-fluoro-2-(oxan-4-yloxy)phenyl]methyl}carbamoyl)-6-methoxypyridin-3-yl]-N-methyl-1H-indazole-3-carboxamide | | 534.1 |
| 51 | 6-[6-methoxy-5-({[(1S,2R)-2-phenylcyclopropyl]methyl}-carbamoyl)pyridin-3-yl]-N-methyl-1H-indazole-3-carboxamide | | 456.3 |
| 52 | 6-[6-methoxy-5-({[(1R,2S)-2-phenylcyclopropyl]methyl}-carbamoyl)pyridin-3-yl]-N-methyl-1H-indazole-3-carboxamide | | 456.1 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

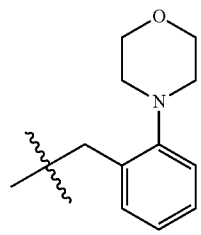 [SMILES: *Cc1ccccc1N1CCOCC1]

| Ex | Name | R | M + H |
|---|---|---|---|
| 53 | 6-[6-methoxy-5-({2-(morpholin-4-yl)phenyl]methyl}carbamoyl)pyridin-3-yl]-N-methyl-1H-indazole-3-carboxamide | 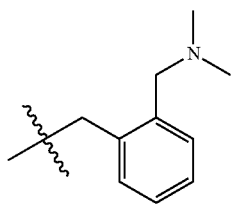 [SMILES: *Cc1ccccc1CN(C)C] | 500.9 |
| 54 | 6-{5-[({2-[(dimethylamino)-methyl]phenyl}methyl)carbamoyl]-6-methoxypyridin-3-yl}-N-methyl-1H-indazole-3-carboxamide | 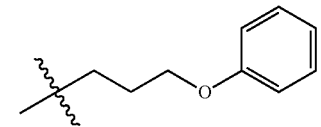 [SMILES: *CCCOc1ccccc1] | 472.9 |
| 55 | 6-{6-methoxy-5-[(3-phenoxypropyl)carbamoyl]pyridin-3-yl}-N-methyl-1H-indazole-3-carboxamide | 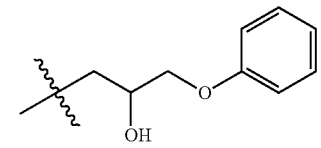 [SMILES: *CC(O)COc1ccccc1] | 460.2 |
| 56 | 6-{5-[(2-hydroxy-3-phenoxypropyl)carbamoyl]-6-methoxypyridin-3-yl}-N-methyl-1H-indazole-3-carboxamide | 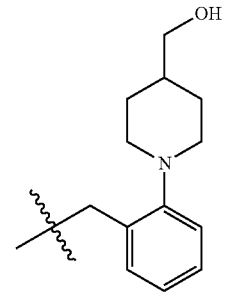 [SMILES: *Cc1ccccc1N1CCC(CO)CC1] | 476.1 |
| 57 | 6-{5-[({2-[4-(hydroxymethyl)-piperidin-1-yl]phenyl}methyl)-carbamoyl]-6-methoxypyridin-3-yl}-N-methyl-1H-indazole-3-carboxamide |  | 529.2 |
| 58 | 6-(6-methoxy-5-{[(2-methoxyphenyl)methyl]carbamoyl}-pyridin-3-yl)-N-methyl-1H-indazole-3-carboxamide | 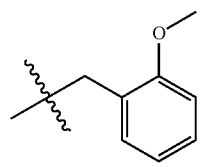 [SMILES: *Cc1ccccc1OC] | 446.2 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

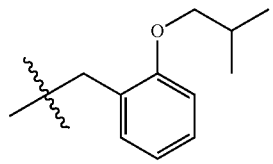 [SMILES: *Cc1ccccc1OCC(C)C]

| Ex | Name | R | M + H |
|----|------|---|-------|
| 59 | 6-[6-methoxy-5-({[2-(2-methylpropoxy)phenyl]methyl}carbamoyl)pyridin-3-yl]-N-methyl-1H-indazole-3-carboxamide | 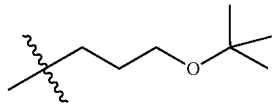 [SMILES: *CCCOC(C)(C)C] | 488.0 |
| 60 | 6-(5-{[3-(tert-butoxy)propyl]carbamoyl}-6-methoxypyridin-3-yl)-N-methyl-1H-indazole-3-carboxamide | 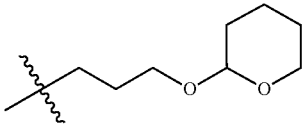 [SMILES: *CCCOC1CCCCO1] | 440.3 |
| 61 | 6-(6-methoxy-5-{[3-(oxan-2-yloxy)propyl]carbamoyl}pyridin-3-yl)-N-methyl-1H-indazole-3-carboxamide | 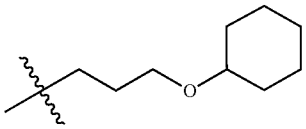 [SMILES: *CCCOC1CCCCC1] | 468.2 |
| 62 | 6-(5-{[3-(cyclohexyloxy)propyl]carbamoyl}-6-methoxypyridin-3-yl)-N-methyl-1H-indazole-3-carboxamide | 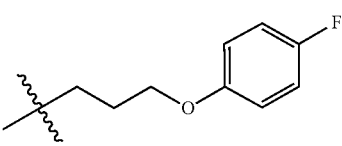 [SMILES: *CCCOc1ccc(F)cc1] | 466.3 |
| 63 | 6-(5-{[3-(4-fluorophenoxy)propyl]carbamoyl}-6-methoxypyridin-3-yl)-N-methyl-1H-indazole-3-carboxamide | 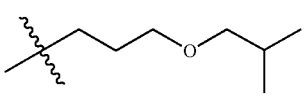 [SMILES: *CCCOCC(C)C] | 478.3 |
| 64 | 6-(6-methoxy-5-{[3-(2-methylpropoxy)propyl]carbamoyl}pyridin-3-yl)-N-methyl-1H-indazole-3-carboxamide | 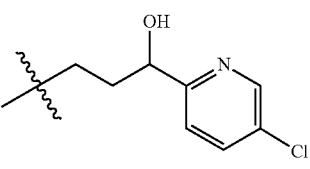 [SMILES: *CCC(O)c1ccc(Cl)cn1] | 440.3 |
| 65 | 6-(5-{[3-(5-chloropyridin-2-yl)-3-hydroxypropyl]carbamoyl}-6-methoxypyridin-3-yl)-N-methyl-1H-indazole-3-carboxamide | 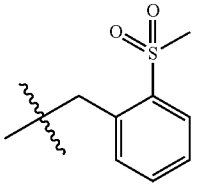 [SMILES: *Cc1ccccc1S(C)(=O)=O] | 495.0 |
| 66 | 6-(5-{[(2-methanesulfonylphenyl)methyl]carbamoyl}-6-methoxypyridin-3-yl)-N-methyl-1H-indazole-3-carboxamide | | 494.1 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

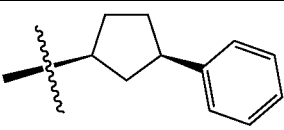

| Ex | Name | R | M + H |
|----|------|---|-------|
| 67 | 6-(6-methoxy-5-{[(1S,3R)-3-phenylcyclopentyl]carbamoyl}-pyridin-3-yl)-N-methyl-1H-indazole-3-carboxamide | 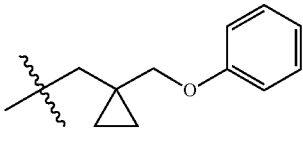 [SMILES: *CC1(COc2ccccc2)CC1] | 470.0 |
| 68 | 6-[6-methoxy-5-({[1-(phenoxymethyl)cyclopropyl]methyl}-carbamoyl)-pyridin-3-yl]-N-methyl-1H-indazole-3-carboxamide | 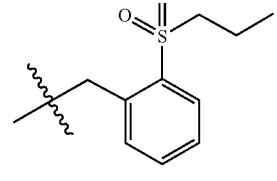 | 486.2 |
| 69 | 6-[6-methoxy-5-({[2-(propane-1-sulfonyl)phenyl]methyl}-carbamoyl)pyridin-3-yl]-N-methyl-1H-indazole-3-carboxamide | 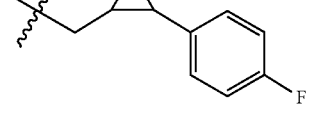 | 521.9 |
| 70 | 6-[5-({[(1R,2R)-2-(4-fluorophenyl)cyclopropyl]methyl}-carbamoyl)-6-methoxypyridin-3-yl]-N-methyl-2H-indazole-3-carboxamide, trans, homochiral | 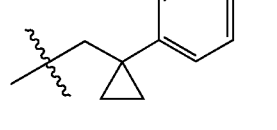 | 474.2 |
| 71 | 6-[5-({[1-(4-fluorophenyl)cyclopropyl]methyl}carbamoyl)-6-methoxypyridin-3-yl]-N-methyl-1H-indazole-3-carboxamide | 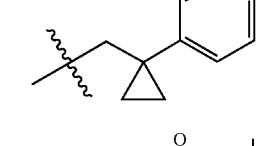 | 474.2 |
| 72 | 6-{6-methoxy-5-[({1-[2-(trifluoromethoxy)phenyl]cyclopropyl}methyl)carbamoyl]-pyridin-3-yl}-N-methyl-1H-indazole-3-carboxamide | 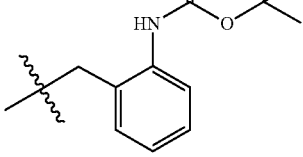 | 540.3 |
| 73 | tert-butyl-N-{2-[({2-methoxy-5-[3-(methylcarbamoyl)-1H-indazol-6-yl]pyridin-3-yl}-formamido)methyl]phenyl}-carbamate | 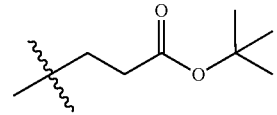 [SMILES: *CCC(=O)OC(C)(C)C] | 531.4 |
| 74 | tert-butyl 3-({2-methoxy-5-[3-(methylcarbamoyl)-1H-indazol-6-yl]pyridin-3-yl}formamido)-propanoate | | 454.1 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

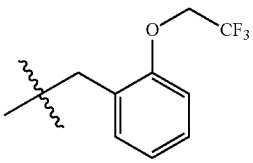 [SMILES: *Cc1ccccc1OCC(F)(F)F]

| Ex | Name | R | M + H |
|----|------|---|-------|
| 75 | 6-[6-methoxy-5-({[2-(2,2,2-trifluoroethoxy)phenyl]methyl}carbamoyl)pyridin-3-yl]-N-methyl-1H-indazole-3-carboxamide, TFA | 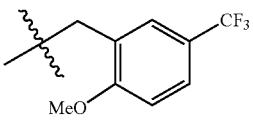 [SMILES: *Cc1cc(C(F)(F)F)ccc1OC] | 514.4 |
| 76 | 6-[6-methoxy-5-({[2-methoxy-5-(trifluoromethyl)phenyl]methyl}carbamoyl)pyridin-3-yl]-N-methyl-1H-indazole-3-carboxamide | 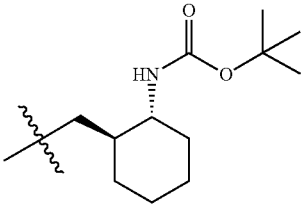 [SMILES: *C[C@@H]1CCCC[C@H]1NC(=O)OC(C)(C)C] | 514.3 |
| 77 | tert-butyl N-[(1R,2S)-2-[({2-methoxy-5-[3-(methylcarbamoyl)-1H-indazol-6-yl]pyridin-3-yl}formamido)methyl]cyclohexyl]carbamate | 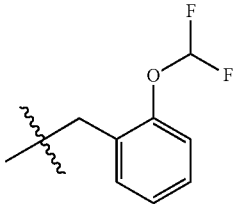 [SMILES: *Cc1ccccc1OC(F)F] | 537.1 |
| 78 | 6-[5-({[2-(difluoromethoxy)phenyl]methyl}carbamoyl)-6-methoxypyridin-3-yl]-N-methyl-1H-indazole-3-carboxamide | 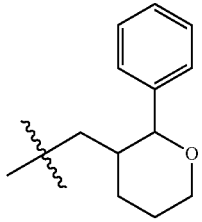 [SMILES: *CC1CCCOC1c1ccccc1] | 482.2 |
| 79 | 6-(6-methoxy-5-{[(2-phenyl-oxan-3-yl)methyl]carbamoyl}-pyridin-3-yl)-N-methyl-1H-indazole-3-carboxamide | 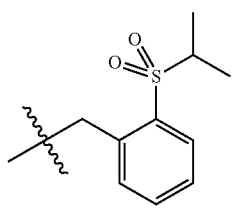 [SMILES: *Cc1ccccc1S(=O)(=O)C(C)C] | 500.3 |
| 80 | 6-[6-methoxy-5-({[2-(propane-2-sulfonyl)phenyl]methyl}carbamoyl)pyridin-3-yl]-N-methyl-1H-indazole-3-carboxamide |  | 522.2 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

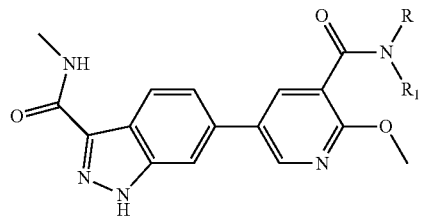

| Ex | Name | R | M + H |
|----|------|---|-------|
| 81 | 6-(5-{[(2,2-dimethylcyclohexyl)methyl]carbamoyl}-6-methoxypyridin-3-yl)-N-methyl-1H-indazole-3-carboxamide | | 450.1 |
| 82 | 6-(5-{[(2-ethylphenyl)methyl]-carbamoyl}-6-methoxy-pyridin-3-yl)-N-methyl-1H-indazole-3-carboxamide | | 444.2 |
| 83 | 6-(5-{[(2-tert-butyloxan-3-yl)-methyl]carbamoyl}-6-methoxy-pyridin-3-yl)-N-methyl-1H-indazole-3-carboxamide | | 480.1 |
| 84 | 6-(5-{[(2-cyanophenyl)methyl]-carbamoyl}-6-methoxypyridin-3-yl)-N-methyl-1H-indazole-3-carboxamide | | 441.0 |
| 85 | 6-[5-({[2-(cyclopropylsulfamoyl)phenyl]methyl}carbamoyl)-6-methoxypyridin-3-yl]-N-methyl-1H-indazole-3-carboxamide | | 535.2 |
| 86 | 6-[5-({[2-(cyclobutylmethoxy)-phenyl]methyl}carbamoyl)-6-methoxypyridin-3-yl]-N-methyl-1H-indazole-3-carboxamide | | 500.2 |
| 87 | 6-(6-methoxy-5-{[3-(2,2,2-trifluoroethoxy)cyclohexyl]-carbamoyl}pyridin-3-yl)-N-methyl-1H-indazole-3-carboxamide | | 506.3 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|----|------|---|-------|
| 88 | ethyl 3-({2-methoxy-5-[3-(methylcarbamoyl)-1H-indazol-6-yl]pyridin-3-yl}-formamido)-2,2-dimethyl-propanoate | | 454.2 |
| 89 | 6-(5-{[(3,5-difluoro-2-methoxy-phenyl)methyl]carbamoyl}-6-methoxy-pyridin-3-yl)-N-methyl-1H-indazole-3-carbox-amide | | 482.2 |
| 90 | tert-butyl 3-({2-methoxy-5-[3-(methylcarbamoyl)-1H-indazol-6-yl]pyridin-3-yl}-formamido)-2,2-dimethyl-propanoate | | 482.2 |
| 91 | 6-{5-[(2-{[(4-fluorophenyl)-methyl]carbamoyl}-2,2-dimethylethyl)carbamoyl]-6-methoxypyridin-3-yl}-N-methyl-1H-indazole-3-carboxamide | | 533.3 |
| 92 | 6-[6-methoxy-5-({[3-(trifluoro-methoxy)phenyl]methyl}-carbamoyl)pyridin-3-yl-N-methyl-1H-indazole-3-carbox-amide | | 500.2 |
| 93 | 6-[6-methoxy-5-({[2-(propan-2-yloxy)phenyl]methyl}-carbamoyl)pyridin-3-yl]-N-methyl-1H-indazole-3-carbox-amide | | 473.9 |
| 94 | 6-(6-methoxy-5-{[(2-methoxy-pyridin-3-yl)methyl]carbam-oyl}pyridin-3-yl)-N-methyl-1H-indazole-3-carboxamide, TFA | | 447.2 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|----|------|---|-------|
| 95 | 6-{6-methoxy-5-[(3-phenyl-adamantan-1-yl)carbamoyl]-pyridin-3-yl}-N-methyl-1H-indazole-3-carboxamide | | 536.3 |
| 96 | 6-[6-methoxy-5-({[1-(3,3,3-trifluoro-2,2-dimethylpropan-oyl)pyrrolidin-2-yl]methyl}-carbamoyl)pyridin-3-yl]-N-methyl-1H-indazole-3-carboxamide | | 547.2 |
| 97 | 6-[6-methoxy-5-({1-[3-(tri-fluoromethoxy)phenyl]ethyl}-carbamoyl)pyridin-3-yl]-N-methyl-1H-indazole-3-carbox-amide | | 514.1 |
| 98 | 6-(6-methoxy-5-{[3-(morpho-line-4-carbonyl)cyclohexyl]-carbamoyl}pyridin-3-yl)-N-methyl-1H-indazole-3-carbox-amide | | 521.4 |
| 99 | 6-(6-methoxy-5-{[3-(pyrrol-idine-1-carbonyl)cyclohexyl]-carbamoyl}pyridin-3-yl)-N-methyl-1H-indazole-3-carbox-amide | | 505.3 |
| 100 | 6-[6-methoxy-5-({3-[methyl-(propyl)carbamoyl]cyclo-hexyl}carbamoyl)pyridin-3-yl]-N-methyl-1H-indazole-3-carboxamide | | 507.0 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|---|---|---|---|
| 101 | 6-[6-methoxy-5-({1-[3-(tri-fluoromethyl)phenyl]ethyl}-carbamoyl)pyridin-3-yl]-N-methyl-1H-indazole-3-carboxamide | | 498.2 |
| 102 | 6-[6-methoxy-5-({[3-(trifluoro-methyl)phenyl]methyl}carbam-oyl)pyridin-3-yl]-N-methyl-1H-indazole-3-carboxamide | | 484.2 |
| 103 | 6-(5-{[2,2-difluoro-3-(propan-2-yloxy)propyl]carbamoyl}-6-methoxypyridin-3-yl)-N-methyl-1H-indazole-3-carbox-amide | | 462.0 |
| 104 | 6-[5-({[4-fluoro-3-(trifluoro-methyl)phenyl]methyl}carbam-oyl)-6-methoxypyridin-3-yl]-N-methyl-1H-indazole-3-carboxamide | | 502.0 |
| 105 | 6-[5-({1-[4-fluoro-3-(trifluoro-methyl)phenyl]ethyl}carbam-oyl)-6-methoxypyridin-3-yl]-N-methyl-1H-indazole-3-carboxamide | | 516.3 |
| 106 | 6-[5-({[3-(cyclopropylmeth-oxy)phenyl]methyl}carbamoyl)-6-methoxypyridin-3-yl]-N-methyl-1H-indazole-3-carbox-amide | | 486.1 |
| 107 | 6-[5-({[3-(cyclopentyloxy)-phenyl]methyl}carbamoyl)-6-methoxypyridin-3-yl]-N-methyl-1H-indazole-3-carbox-amide | | 500.3 |
| 108 | 6-[6-methoxy-5-({[2-(trifluoro-methyl)phenyl]methyl}carbam-oyl)pyridin-3-yl]-N-methyl-1H-indazole-3-carboxamide | | 484.2 |
| 109 | 6-[6-methoxy-5-({1-[2-(tri-fluoromethyl)phenyl]ethyl}-carbamoyl)pyridin-3-yl]-N-methyl-1H-indazole-3-carbox-amide | | 498.0 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|----|------|---|-------|
| 110 | 6-[5-({[2-(cyclopentylmeth-oxy)phenyl]methyl}carbam-oyl)-6-methoxypyridin-3-yl]-N-methyl-1H-indazole-3-carboxamide | | 514.0 |
| 111 | 6-[6-methoxy-5-({[3-(propan-2-yloxy)phenyl]methyl}-carbamoyl)pyridin-3-yl]-N-methyl-1H-indazole-3-carbox-amide, TFA | | 474.0 |
| 112 | 6-[5-({[2-(cyclobutylmeth-oxy)pyridin-3-yl]methyl}-carbamoyl)-6-methoxypyridin-3-yl]-N-methyl-1H-indazole-3-carboxamide | | 501.2 |
| 113 | 6-[5-({[2-(cyclohexyloxy)-phenyl]methyl}carbamoyl)-6-methoxypyridin-3-yl]-N-methyl-1H-indazole-3-carbox-amide | | 514.1 |
| 114 | 6-[5-({[2-fluoro-3-(trifluoro-methyl)phenyl]methyl}carbam-oyl)-6-methoxypyridin-3-yl]-N-methyl-1H-indazole-3-carboxamide | | 502.0 |
| 115 | 6-[5-({[3-(cyclobutylmeth-oxy)phenyl]methyl}carbam-oyl)-6-methoxypyridin-3-yl]-N-methyl-1H-indazole-3-carboxamide | | 500.2 |
| 116 | 6-(5-{[(2,2-dimethylcyclo-pentyl)methyl]carbamoyl}-6-methoxypyridin-3-yl)-N-methyl-1H-indazole-3-carbox-amide | | 436.0 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|----|------|---|-------|
| 117 | 6-[5-({[3-(cyclobutylmethoxy)-pyridin-2-yl]methyl}carbamoyl)-6-methoxypyridin-3-yl]-N-methyl-1H-indazole-3-carboxamide, TFA | | 500.9 |
| 118 | 6-{6-methoxy-5-[(3-phenoxycyclohexyl)carbamoyl]pyridin-3-yl}-N-methyl-1H-indazole-3-carboxamide | | 500.0 |
| 119 | 6-[5-({[2-fluoro-3-(trifluoromethoxy)phenyl]methyl}-carbamoyl)-6-methoxy-pyridin-3-yl]-N-methyl-1H-indazole-3-carboxamide | | 518.1 |
| 120 | 6-(5-{[3-(dimethylcarbamoyl)cyclohexyl]carbamoyl}-6-methoxypyridin-3-yl)-N-methyl-1H-indazole-3-carboxamide | | 479.0 |
| 121 | 6-(5-{[3-(diethylcarbamoyl)-cyclohexyl]carbamoyl}-6-methoxypyridin-3-yl)-N-methyl-1H-indazole-3-carboxamide | | 507.1 |
| 122 | 6-[5-({3-[ethyl(methyl)carbamoyl]cyclohexyl}carbamoyl)-6-methoxypyridin-3-yl]-N-methyl-1H-indazole-3-carboxamide | | 493.0 |
| 123 | 6-[5-({3-[(cyclopropylmethyl)(propyl)carbamoyl]cyclohexyl}-carbamoyl)-6-methoxypyridin-3-yl]-N-methyl-1H-indazole-3-carboxamide | | 547.2 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|----|------|---|-------|
| 124 | 6-[5-({3-[(cyclobutylmethyl)-(ethyl)carbamoyl]cyclohexyl}-carbamoyl)-6-methoxypyridin-3-yl]-N-methyl-1H-indazole-3-carboxamide | | 547.2 |
| 125 | 6-[5-({3-[cyclopropyl(methyl)-carbamoyl]cyclohexyl}carbam-oyl)-6-methoxypyridin-3-yl]-N-methyl-1H-indazole-3-carbox-amide | | 505.2 |
| 126 | 6-[5-({[3,5-difluoro-2-(propan-2-yloxy)phenyl]methyl}-carbamoyl)-6-methoxypyridin-3-yl]-N-methyl-1H-indazole-3-carboxamide | | 510.1 |
| 127 | 6-[5-({[2-fluoro-6-(propan-2-yloxy)phenyl]methyl}-carbamoyl)-6-methoxy-pyridin-3-yl]-N-methyl-1H-indazole-3-carboxamide | | 492.0 |
| 128 | 6-[5-({[2-(cyclopropylmeth-oxy)-3,5-difluorophenyl]-methyl}carbamoyl)-6-meth-oxypyridin-3-yl]-N-methyl-1H-indazole-3-carboxamide | | 522.0 |
| 129 | 6-[6-methoxy-5-({1-[2-(tri-fluoromethyl)phenyl]ethyl}-carbamoyl)pyridin-3-yl]-N-methyl-1H-indazole-3-carboxamide, homochiral, unknown isomer | | 498.0 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|---|---|---|---|
| 130 | 6-[5-({[5-fluoro-2-(propan-2-yloxy)phenyl]methyl}carbamoyl)-6-methoxy-pyridin-3-yl]-N-methyl-1H-indazole-3-carboxamide | | 492.2 |
| 131 | 6-{6-methoxy-5-[({2-[(3-methylcyclopentyl)oxy]-phenyl}methyl)carbamoyl]-pyridin-3-yl}-N-methyl-1H-indazole-3-carboxamide | | 514.2 |
| 132 | 6-(5-{[3-(3,3-difluoroazetidine-1-carbonyl)cyclohexyl]-carbamoyl}-6-methoxypyridin-3-yl)-N-methyl-1H-indazole-3-carboxamide, TFA | | 527.2 |
| 133 | cyclohexyl 1-[({2-methoxy-5-[3-(methylcarbamoyl)-1H-indazol-6-yl]pyridin-3-yl}-formamido)methyl]cyclopropane-1-carboxylate, TFA | | 506.0 |
| 134 | 6-{5-[(3S)-3-[(4-fluorophenyl)-methyl]piperidine-1-carbonyl]-6-methoxy-pyridin-3-yl}-N-methyl-1H-indazole-3-carboxamide, TFA | | 502.1 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

| Ex | Name | R | M + H |
|----|------|---|-------|
| 135 | tert-butyl 4-({2-methoxy-5-[3-(methylcarbamoyl)-1H-indazol-6-yl]pyridin-3-yl}formamido)butanoate | | 468.0 |
| 136 | tert-butyl (3S)-3-{2-methoxy-5-[3-(methylcarbamoyl)-1H-indazol-6-yl]pyridine-3-amido}-pyrrolidine-1-carboxylate | | 495.4 |
| 137 | 6-[5-({[2-fluoro-5-(trifluoromethoxy)phenyl]methyl-{carbamoyl)-6-methoxy-pyridin-3-yl]-N-methyl-1H-indazole-3-carboxamide | | 518.2 |
| 138 | 6-{5-[(cyclohexylmethyl)-carbamoyl]-6-methoxy-pyridin-3-yl}-N-methyl-1H-indazole-3-carboxamide | | 421.9 |
| 139 | tert-butyl (3S)-3-({2-methoxy-5-[3-(methylcarbamoyl)-1H-indazol-6-yl]pyridin-3-yl}-formamido)butanoate | | 468.4 |
| 140 | cyclopentyl 1-[({2-methoxy-5-[3-(methylcarbamoyl)-1H-indazol-6-yl]pyridin-3-yl}-formamido)methyl]cyclopropane-1-carboxylate | | 492.3 |

TABLE 2-continued

Compounds in Table 2 were made in a similar fashion to example 1. Non-delineated stereochemistry is racemic or diastereomeric unless otherwise noted in the text. In cases where R1 is not hydrogen, the full amine is shown under the R group column.

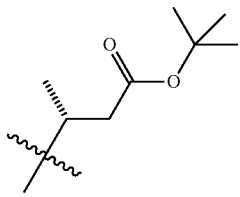 [SMILES: *[C@H](C)CC(=O)OC(C)(C)C]

| Ex | Name | R | M + H |
|---|---|---|---|
| 141 | tert-butyl (3R)-3-({2-methoxy-5-[3-(methylcarbamoyl)-1H-indazol-6-yl]pyridin-3-yl}-formamido)butanoate | 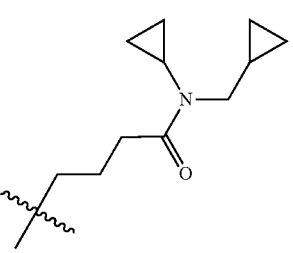 [SMILES: *CCCC(=O)N(CC1CC1)C1CC1] | 468.2 |
| 142 | 6-[5-({3-[cyclopropyl(cyclopropylmethyl)carbamoyl]-propyl}carbamoyl)-6-methoxypyridin-3-yl]-N-methyl-1H-indazole-3-carboxamide | 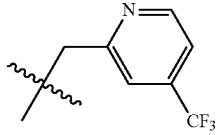 | 505.1 |
| 143 | 6-[6-methoxy-5-({[4-(trifluoromethyl)pyridin-2-yl]methyl}-carbamoyl)pyridin-3-yl]-N-methyl-1H-indazole-3-carboxamide | | 485.1 |

TABLE 3

Compounds in Table 3 were made in a similar fashion to example 26. Non-delineated stereochemistry is racemic or diastereomeric unless otherwise noted in the text.

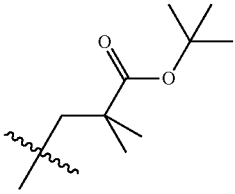

| Ex | Name | R | M + H |
|---|---|---|---|
| 144 | tert-butyl 3-({5-[4-fluoro-3-(methylcarbamoyl)-1H-indazol-6-yl]-2-methoxy-pyridin-3-yl}formamido)-2,2-dimethylpropanoate | | 500.2 |

TABLE 3-continued

Compounds in Table 3 were made in a similar fashion to example 26. Non-delineated stereochemistry is racemic or diastereomeric unless otherwise noted in the text.

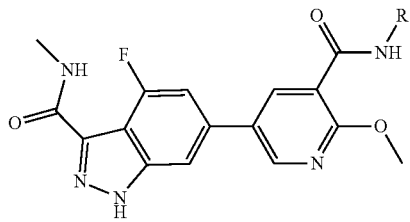

| Ex | Name | R | M + H |
|---|---|---|---|
| 145 | 6-(5-{[(3S)-3-(4-chloro-phenyl)-3-hydroxypropyl]-carbamoyl}-6-methoxy-pyridin-3-yl)-4-fluoro-N-methyl-1H-indazole-3-carboxamide | | 512.4 |
| 146 | tert-butyl (3S)-3-({5-[4-fluoro-3-(methylcarbamoyl)-1H-indazol-6-yl]-2-methox-ypyridin-3-yl}formamido)-butanoate | | 486.3 |
| 147 | 4-fluoro-6-[6-methoxy-5-({1-[3-(trifluoromethoxy)-phenyl]ethyl}carbamoyl)-pyridin-3-yl]-N-methyl-1H-indazole-3-carboxamide | | 532.2 |

TABLE 4

Compounds in Table 4 were made in a similar fashion to examples 1 and 12. Non-delineated stereochemistry is racemic or diastereomeric unless otherwise noted in the text.

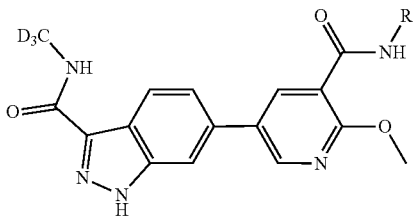

| Ex | Name | R | M + H |
|---|---|---|---|
| 148 | oxan-4-yl 3-[(2-methoxy-5-{3-[(deutero)methylcarbamoyl]-1H-indazol-6-yl}pyridin-3-yl)formamido]-2,2-dimethyl-propanoate | | 513.2 |

TABLE 4-continued

Compounds in Table 4 were made in a similar fashion to examples 1 and 12. Non-delineated stereochemistry is racemic or diastereomeric unless otherwise noted in the text.

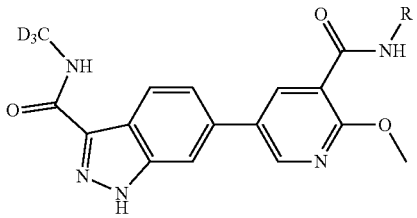

| Ex | Name | R | M + H |
|---|---|---|---|
| 149 | tert-butyl 3-[(2-methoxy-5-{3-[(deutero)methylcarbamoyl]-1H-indazol-6-yl}pyridin-3-yl)-formamido]-2,2-dimethyl-propanoate | | 485.2 |
| 150 | tert-butyl 3-[(2-methoxy-5-{3-[(deutero)methylcarbamoyl]-1H-indazol-6-yl}pyridin-3-yl)-formamido]propanoate | | 457.0 |
| 151 | 6-[6-methoxy-5-({1-[3-(tri-fluoromethoxy)phenyl]ethyl}-carbamoyl)pyridin-3-yl]-N-(deutero)methyl-1H-indazole-3-carboxamide | | 517.0 |
| 152 | 6-[6-methoxy-5-({1-[2-(tri-fluoromethoxy)phenyl]ethyl}-carbamoyl)pyridin-3-yl]-N-(deutero)methyl-1H-indazole-3-carboxamide | | 517.4 |
| 153 | 6-[6-methoxy-5-({[2-(trifluoro-methoxy)phenyl]{methyl}-carbamoyl)pyridin-3-yl]-N-(deutero)methyl-1H-indazole-3-carboxamide | | 503.0 |

TABLE 5

Compounds in Table 5 were made in a similar fashion to example 1. Non-delineated stereochemistry is racemic or diastereomeric unless otherwise noted in the text.

| Ex | Name | R | M + H |
|----|------|---|-------|
| 154 | N-methyl-6-(6-methyl-5-{[(1S,3R)-3-phenylcyclopentyl]carbamoyl}-pyridin-3-yl)-1H-indazole-3-carboxamide | | 454.0 |
| 155 | N-methyl-6-[6-methyl-5-({1-[3-(trifluoromethoxy)phenyl]ethyl}carbamoyl)pyridin-3-yl]-1H-indazole-3-carboxamide, homochiral, unknown isomer | | 498.3 |
| 156 | N-methyl-6-[6-methyl-5-({1-[3-(trifluoromethoxy)phenyl]ethyl}carbamoyl)pyridin-3-yl]-1H-indazole-3-carboxamide, homochiral, unknown isomer | | 498.1 |
| 157 | 6-[5-({[2-(cyclopentyloxy)-5-fluorophenyl]methyl}carbamoyl)-6-methylpyridin-3-yl]-N-methyl-1H-indazole-3-carboxamide, TFA | | 502.2 |

TABLE 6

Compounds in Table 6 were made in a similar fashion to example 1. Non-delineated stereochemistry is racemic or diastereomeric unless otherwise noted in the text.

| Ex | Name | R | M + H |
|----|------|---|-------|
| 158 | 6-[6-methoxy-2-methyl-5-({1-[2-(trifluoromethoxy)phenyl]ethyl}carbamoyl)-pyridin-3-yl]-N-methyl-1H-indazole-3-carboxamide | | 528.1 |

TABLE 6-continued

Compounds in Table 6 were made in a similar fashion to example 1. Non-delineated stereochemistry is racemic or diastereomeric unless otherwise noted in the text.

| Ex | Name | R | M + H |
|---|---|---|---|
| 159 | 6-(5-{[(2,2-dimethylcyclo-pentyl)methyl]carbamoyl}-6-methoxy-2-methyl-pyridin-3-yl)-N-methyl-1H-indazole-3-carboxamide | | 450.2 |
| 160 | 6-[6-methoxy-2-methyl-5-({[3-(trifluoromethoxy)-phenyl]methyl}carbamoyl)-pyridin-3-yl]-N-methyl-1H-indazole-3-carboxamide | | 514.2 |
| 161 | 6-[5-({[2-fluoro-5-(tri-fluoromethoxy)phenyl]-methyl}carbamoyl)-6-methoxy-2-methylpyridin-3-yl]-N-methyl-1H-indazole-3-carboxamide | | 532.2 |

TABLE 7

Compounds in Table 7 were made in a similar fashion to example 1. Non-delineated stereochemistry is racemic or diastereomeric unless otherwise noted in the text.

| Ex | Name | R | M + H |
|---|---|---|---|
| 162 | 6-[2,6-dimethyl-5-({1-[2-(trifluoromethoxy)phenyl]-ethyl}carbamoyl)pyridin-3-yl]-N-methyl-1H-indazole-3-carboxamide | | 511.9 |
| 163 | 6-[2,6-dimethyl-5-({1-[3-(trifluoromethoxy)phenyl]-ethyl}carbamoyl)pyridin-3-yl]-N-methyl-1H-indazole-3-carboxamide, homochiral, unknown isomer | | 512.1 |

TABLE 7-continued

Compounds in Table 7 were made in a similar fashion to example 1. Non-delineated stereochemistry is racemic or diastereomeric unless otherwise noted in the text.

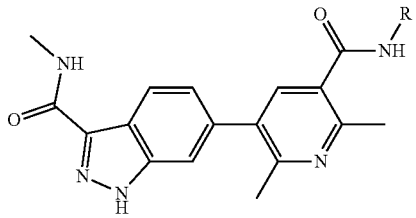

| Ex | Name | R | M + H |
|----|------|---|-------|
| 164 | 6-[2,6-dimethyl-5-({1-[3-(trifluoromethoxy)phenyl]-ethyl}carbamoyl)pyridin-3-yl]-N-methyl-1H-indazole-3-carboxamide, homochiral, unknown isomer | 3-OCF₃ phenyl ethyl | 512.1 |

TABLE 8

Compounds in Table 8 were made in a similar fashion to examples 1 and 12. Non-delineated stereochemistry is racemic or diastereomeric unless otherwise noted in the text.

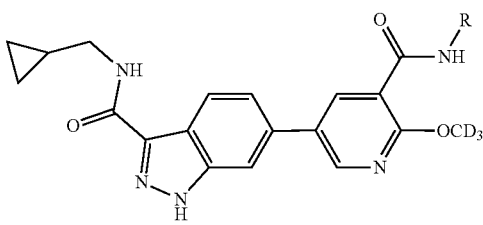

| Ex | Name | R | M + H |
|----|------|---|-------|
| 165 | tert-butyl 3-[(5-{3-[(cyclopropyl-methyl)carbamoyl]-1H-indazol-6-yl}-2-(deutero)methoxypyridin-3-yl)formamido]propanoate | tert-butyl ester propyl | 497.6 |
| 166 | N-(cyclopropylmethyl)-6-[6-(deutero)methoxy-5-({1-[3-(tri-fluoromethoxy)phenyl]ethyl}-carbamoyl)pyridin-3-yl]-1H-indazole-3-carboxamide | 3-OCF₃ phenyl ethyl | 557.4 |
| 167 | 6-(5-{[(3S)-3-(4-chlorophenyl)-3-hydroxypropyl]carbamoyl}-6-(deutero)methoxypyridin-3-yl)-N-(cyclopropylmethyl)-1H-indazole-3-carboxamide | 4-Cl phenyl 3-hydroxypropyl | 537.3 |
| 168 | N-(cyclopropylmethyl)-6-[6-(deutero)methoxy-5-({1-[2-(tri-fluoromethoxy)phenyl]ethyl}-carbamoyl)pyridin-3-yl]-1H-indazole-3-carboxamide | 2-OCF₃ phenyl ethyl | 557.2 |

TABLE 9

Compounds in Table 9 were made in a similar fashion to examples 24 and 25. Non-delineated stereochemistry is racemic or diastereomeric unless otherwise noted in the text.

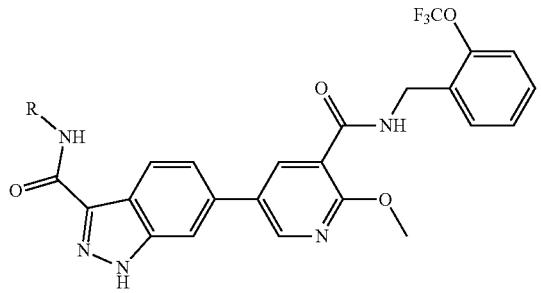

| Ex | Name | R | M + H |
|---|---|---|---|
| 169 | N-(1-methanesulfonylpiperidin-4-yl)-6-[6-methoxy-5-({[2-(trifluoromethoxy)phenyl]methyl}carbamoyl)pyridin-3-yl]-1H-indazole-3-carboxamide | | 647.5 |
| 170 | N-ethyl-6-[6-methoxy-5-({[2-(trifluoromethoxy)phenyl]methyl}carbamoyl)pyridin-3-yl]-1H-indazole-3-carboxamide | | 514.4 |
| 171 | N-[(1R)-1-cyclopropylethyl]-6-[6-methoxy-5-({[2-(trifluoromethoxy)phenyl]methyl}carbamoyl)pyridin-3-yl]-1H-indazole-3-carboxamide | | 554.3 |
| 172 | N-(cyclopropylmethyl)-6-[6-methoxy-5-({[2-(trifluoromethoxy)phenyl]methyl}carbamoyl)pyridin-3-yl]-1H-indazole-3-carboxamide | | 540.4 |
| 174 | N-cyclopropyl-6-[6-methoxy-5-({[2-(trifluoromethoxy)phenyl]methyl}carbamoyl)pyridin-3-yl]-1H-indazole-3-carboxamide | | 525.9 |
| 175 | N-butyl-6-[6-methoxy-5-({[2-(trifluoromethoxy)phenyl]methyl}carbamoyl)pyridin-3-yl]-1H-indazole-3-carboxamide | | 542.2 |
| 176 | 6-[6-methoxy-5-({[2-(trifluoromethoxy)phenyl]methyl}carbamoyl)pyridin-3-yl]-N-propyl-1H-indazole-3-carboxamide | | 528.2 |
| 177 | 6-[6-methoxy-5-({[2-(trifluoromethoxy)phenyl]methyl}carbamoyl)pyridin-3-yl]-N-[3-(2-oxopyrrolidin-1-yl)propyl]-1H-indazole-3-carboxamide | | 611.2 |
| 178 | 6-[6-methoxy-5-({[2-(trifluoromethoxy)phenyl]methyl}carbamoyl)pyridin-3-yl]-N-(2,2,2-(trifluoroethyl)-1H-indazole-3-carboxamide | | 568.1 |

TABLE 9-continued

Compounds in Table 9 were made in a similar fashion to examples 24 and 25. Non-delineated stereochemistry is racemic or diastereomeric unless otherwise noted in the text.

| Ex | Name | R | M + H |
|---|---|---|---|
| 179 | 6-[6-methoxy-5-({[2-(trifluoromethoxy)phenyl]methyl}carbamoyl)pyridin-3-yl]-N-(propan-2-yl)-1H-indazole-3-carboxamide | isopropyl | 528.4 |
| 180 | N-(1-acetylpiperidin-4-yl)-6-[6-methoxy-5-({[2-(trifluoromethoxy)phenyl]methyl}carbamoyl)pyridin-3-yl]-1H-indazole-3-carboxamide | 1-acetylpiperidin-4-yl | 611.3 |
| 181 | 6-[6-methoxy-5-({[2-(trifluoromethoxy)phenyl]methyl}carbamoyl)pyridin-3-yl]-N-[5-oxo-1-(propan-2-yl)pyrrolidin-3-yl]-1H-indazole-3-carboxamide, TFA | 5-oxo-1-isopropylpyrrolidin-3-yl | 611.2 |
| 182 | N-(2-hydroxyethyl)-6-[6-methoxy-5-({[2-(trifluoromethoxy)phenyl]methyl}carbamoyl)pyridin-3-yl]-1H-indazole-3-carboxamide | 2-hydroxyethyl | 530.0 |
| 183 | N-[(1,1,2,2,2-deutero)ethyl]-6-[6-methoxy-5-({[2-(trifluoromethoxy)phenyl]methyl}carbamoyl)pyridin-3-yl]-1H-indazole-3-carboxamide | pentadeuteroethyl | 519.1 |
| 184 | N-[4-(diethylamino)cyclohexyl]-6-[6-methoxy-5-({[2-(trifluoromethoxy)phenyl]methyl}carbamoyl)pyridin-3-yl]-1H-indazole-3-carboxamide, TFA | 4-(diethylamino)cyclohexyl | 639.5 |
| 185 | N-[4-(dimethylamino)cyclohexyl]-6-[6-methoxy-5-({[2-(trifluoromethoxy)phenyl]methyl}carbamoyl)pyridin-3-yl]-1H-indazole-3-carboxamide | 4-(dimethylamino)cyclohexyl | 611.1 |

TABLE 9-continued

Compounds in Table 9 were made in a similar fashion to examples 24 and 25. Non-delineated stereochemistry is racemic or diastereomeric unless otherwise noted in the text.

| Ex | Name | R | M + H |
|---|---|---|---|
| 186 | 6-[6-methoxy-5-({[2-(trifluoro-methoxy)phenyl]methyl}-carbamoyl)pyridin-3-yl]-N-[1-(2-methoxyphenyl)-5-oxo-pyrrolidin-3-yl]-1H-indazole-3-carboxamide | | 675.3 |
| 187 | 6-[6-methoxy-5-({[2-(trifluoro-methoxy)phenyl]methyl}-carbamoyl)pyridin-3-yl]-N-(1-methyl-5-oxopyrrolidin-3-yl)-1H-indazole-3-carboxamide, TFA | | 583.1 |
| 188 | N-{4-[di(deutero)methylamino]-cyclohexyl}-6-[6-methoxy-5-({[2-(trifluoromethoxy)phenyl]-methyl}carbamoyl)pyridin-3-yl]-1H-indazole-3-carboxamide | | 617.5 |
| 189 | 6-[6-methoxy-5-({[2-(trifluoro-methoxy)phenyl]methyl}-carbamoyl)pyridin-3-yl]-N-[(1r,4r)-4-hydroxycyclohexyl]-1H-indazole-3-carboxamide | | 584.4 |

TABLE 10

Compounds in Table 10 were made in a similar fashion to examples 12, 24 and 25. All compounds are homochiral.

| Ex | Name | R | M + H |
|---|---|---|---|
| 190 | N-cyclopropyl-6-(5-{[(3R,4S)-1-(3,3-difluorocyclobutanecarbonyl)-4-fluoropyrrolidin-3-yl]carbamoyl}-6-(deutero)methoxypyridin-3-yl)-1H-indazole-3-carboxamide | cyclopropyl | 560.1 |
| 191 | 6-(5-{[(3R,4S)-1-(3,3-difluorocyclobutanecarbonyl)-4-fluoropyrrolidin-3-yl]carbamoyl}-6-(deutero)methoxypyridin-3-yl)-N-(3,3-difluorocyclobutyl)-1H-indazole-3-carboxamide | 3,3-difluorocyclobutyl | 610.1 |
| 192 | 6-(5-{[(3R,4S)-1-(3,3-difluorocyclobutanecarbonyl)-4-fluoropyrrolidin-3-yl]carbamoyl}-6-(deutero)methoxypyridin-3-yl)-N-[(1,1,2,2,2-deutero)-ethyl]-1H-indazole-3-carboxamide | pentadeuteroethyl | 553.2 |
| 193 | 6-(5-{[(3R,4S)-1-(3,3-difluorocyclobutanecarbonyl)-4-fluoropyrrolidin-3-yl]carbamoyl}-6-(deutero)methoxypyridin-3-yl)-N-(2-fluoro-2-methyl-propyl)-1H-indazole-3-carboxamide | 2-fluoro-2-methylpropyl | 594.2 |

TABLE 11

Compounds in Table 11 were made in a similar fashion to examples 1 and 12. Non-delineated stereochemistry is racemic or diastereomeric unless otherwise noted in the text.

| Ex | Name | R | M + H |
|---|---|---|---|
| 194 | N-cyclopropyl-6-(5-{[(1S)-1-[2-fluoro-5-(trifluoromethyl)phenyl]-ethyl]carbamoyl}-6-(deutero)methoxypyridin-3-yl)-1H-indazole-3-carboxamide | (1S)-1-[2-fluoro-5-(trifluoromethyl)phenyl]ethyl | 545.2 |

TABLE 11-continued

Compounds in Table 11 were made in a similar fashion to examples 1 and 12. Non-delineated stereochemistry is racemic or diastereomeric unless otherwise noted in the text.

| Ex | Name | R | M + H |
|---|---|---|---|
| 195 | tert-butyl (3S)-3-({5-[3-(cyclopropylcarbamoyl)-1H-indazol-6-yl]-2-(deutero)methoxypyridin-3-yl}formamido)butanoate | | 497.5 |
| 196 | tert-butyl (3R)-3-({5-[3-(cyclopropylcarbamoyl)-1H-indazol-6-yl]-2-(deutero)methoxypyridin-3-yl}formamido)butanoate | | 497.0 |
| 197 | N-cyclopropyl-6-[6-(deutero)-methoxy-5-({1-[3-(trifluoromethoxy)phenyl]ethyl}carbamoyl)-pyridin-3-yl]-1H-indazole-3-carboxamide | | 543.3 |
| 198 | 6-(5-{[(3S)-3-(4-chlorophenyl)-3-hydroxypropyl]carbamoyl}-6-(deutero)methoxypyridin-3-yl)-N-cyclopropyl-1H-indazole-3-carboxamide | | 523.4 |
| 199 | N-cyclopropyl-6-(5-{[(3R,4S)-1-(3,3-difluorocyclopentanecarbonyl)-4-fluoropyrrolidin-3-yl]carbamoyl}-6-(deutero)methoxypyridin-3-yl)-1H-indazole-3-carboxamide, TFA | | 574.5 |
| 200 | tert-butyl 3-({5-[3-(cyclopropylcarbamoyl)-1H-indazol-6-yl]-2-(deutero)methoxypyridin-3-yl}-formamido)-2,2-dimethyl-propanoate | | 511.4 |
| 201 | N-cyclopropyl-6-(5-{[(1R)-1-[2-fluoro-5-(trifluoromethoxy)-phenyl]ethyl]carbamoyl}-6-(deutero)methoxypyridin-3-yl)-1H-indazole-3-carboxamide | | 561.1 |
| 202 | N-cyclopropyl-6-[6-(deutero)-methoxy-5-{[(1R)-1-[3-(trifluoromethoxy)phenyl]ethyl]carbamoyl}pyridin-3-yl]-1H-indazole-3-carboxamide | | 543.2 |

TABLE 11-continued

Compounds in Table 11 were made in a similar fashion to examples 1 and 12. Non-delineated stereochemistry is racemic or diastereomeric unless otherwise noted in the text.

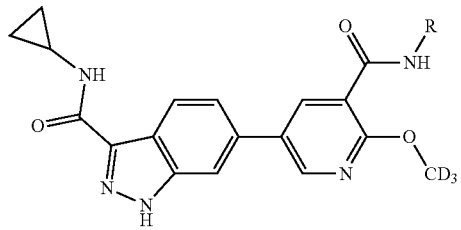

| Ex | Name | R | M + H |
|----|------|---|-------|
| 203 | N-cyclopropyl-6-(5-{[3-(3,3-difluoropyrrolidine-1-carbonyl)-cyclohexyl]carbamoyl}-6-(deutero)methoxypyridin-3-yl)-1H-indazole-3-carboxamide, TFA | | 570.0 |
| 204 | N-cyclopropyl-6-[6-deutero)-methoxy-5-{[3-(pyrrolidine-1-carbonyl)cyclohexyl]carbamoyl}-pyridin-3-yl]-1H-indazole-3-carboxamide, TFA | | 534.4 |
| 205 | N-cyclopropyl-6-[6-(deutero)-methoxy-5-{[(1R)-1-[3-(trifluoromethoxy)phenyl](2,2,2-deutero)-ethyl]carbamoyl}pyridin-3-yl]-1H-indazole-3-carboxamide, TFA | | 546.0 |
| 206 | N-cyclopropyl-6-(5-{[(1S)-1-[2-fluoro-5-(trifluoromethoxy)-phenyl](2,2,2-deutero)ethyl]-carbamoyl}-6-(deutero)methoxy-pyridin-3-yl)-1H-indazole-3-carboxamide | | 564.2 |
| 207 | N-cyclopropyl-6-(5-{[(1R)-1-[2-fluoro-5-(trifluoromethoxy)-phenyl](2,2,2-deutero)ethyl]-carbamoyl}-6-(deutero)methoxy-pyridin-3-yl)-1H-indazole-3-carboxamide | | 564.1 |
| 208 | N-cyclopropyl-6-(5-{[(1S)-1-[2-fluoro-5-(trifluoromethyl)phenyl]-(2,2,2-deutero)ethyl]carbamoyl}-6-(deutero)methoxypyridin-3-yl)-1H-indazole-3-carboxamide, TFA | | 548.3 |
| 209 | N-cyclopropyl-6-[6-(deutero)-methoxy-5-{[(1R)-1-[2-(trifluoromethyl)phenyl]ethyl]carbamoyl}-pyridin-3-yl]-1H-indazole-3-carboxamide | | 527.2 |

TABLE 11-continued

Compounds in Table 11 were made in a similar fashion to examples 1 and 12. Non-delineated stereochemistry is racemic or diastereomeric unless otherwise noted in the text.

| Ex | Name | R | M + H |
|----|------|---|-------|
| 210 | N-cyclopropyl-6-[6-(deutero)methoxy-5-{[(1R)-1-[3-(trifluoromethyl)phenyl]ethyl]carbamoyl}pyridin-3-yl]-1H-indazole-3-carboxamide | (1R)-1-[3-(trifluoromethyl)phenyl]ethyl | 527.3 |
| 211 | N-cyclopropyl-6-[6-(deutero)-methoxy-5-{[(1S)-1-[3-(trifluoromethyl)phenyl]ethyl]carbamoyl}-pyridin-3-yl]-1H-indazole-3-carboxamide | (1S)-1-[3-(trifluoromethyl)phenyl]ethyl | 527.2 |

TABLE 12

Compounds in Table 12 were made in a similar fashion to examples 1 and 12. Non-delineated stereochemistry is racemic or diastereomeric unless otherwise noted in the text.

| Ex | Name | R | M + H |
|----|------|---|-------|
| 212 | 6-[5-(1-[5-fluoro-2-(trifluoromethyl)-phenyl]ethyl}carbamoyl)-6-(deutero)-methoxypyridin-3-yl]-N-(deutero)-methyl-1H-indazole-3-carboxamide | 1-[5-fluoro-2-(trifluoromethyl)phenyl]ethyl | 522.2 |
| 213 | 6-(5-{[(1S)-1-[2-fluoro-5-(trifluoromethyl)phenyl]ethyl]carbamoyl}-6-(deutero)methoxypyridin-3-yl)-N-(deutero)methyl-1H-indazole-3-carboxamide | (1S)-1-[2-fluoro-5-(trifluoromethyl)phenyl]ethyl | 522.2 |
| 214 | 6-[6-(deutero)methoxy-5-{[(1S)-1-[3-(trifluoromethyl)phenyl]ethyl]carbamoyl}pyridin-3-yl]-N-(deutero)methyl-1H-indazole-3-carboxamide | (1S)-1-[3-(trifluoromethyl)phenyl]ethyl | 504.2 |

TABLE 12-continued

Compounds in Table 12 were made in a similar fashion to examples 1 and 12. Non-delineated stereochemistry is racemic or diastereomeric unless otherwise noted in the text.

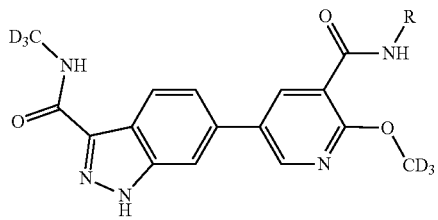

| Ex | Name | R | M + H |
|---|---|---|---|
| 215 | 6-(5-{[(1R)-1-[2-fluoro-5-(trifluoro-methyl)phenyl](2,2,2-deutero)ethyl]-carbamoyl}-6-deutero)methoxy-pyridin-3-yl)-N-(deutero)methyl-1H-indazole-3-carboxamide | D₃C, F, CF₃ phenyl | 525.2 |
| 216 | 6-(5-{[(1R)-1-[2-fluoro-5-(trifluoro-methoxy)phenyl](2,2,2-deutero)-ethyl]carbamoyl}-6-(deutero)meth-oxypyridin-3-yl)-N-(deutero)methyl-1H-indazole-3-carboxamide | D₃C, F, OCF₃ phenyl | 541.2 |
| 217 | 6-[6-(deutero)methoxy-5-{[(1R)-1-[3-(trifluoromethoxy)phenyl](2,2,2-deutero)ethyl]carbamoyl}pyridin-3-yl]-N-(deutero)methyl-1H-indazole-3-carboxamide, TFA | D₃C, OCF₃ phenyl | 523.2 |
| 218 | 6-(5-{[(1R)-1-[2-fluoro-5-(trifluoro-methoxy)phenyl]ethyl]carbamoyl}-6-(deutero)methoxypyridin-3-yl)-N-(deutero)methyl-1H-indazole-3-carboxamide | F, OCF₃ phenyl | 538.1 |
| 219 | 6-[6-(deutero)methoxy-5-{[(1R)-1-[2-(trifluoromethyl)phenyl]ethyl]-carbamoyl}pyridin-3-yl]-N-(deutero)-methyl-1H-indazole-3-carboxamide | F₃C phenyl | 504.4 |
| 220 | 6-[6-(deutero)methoxy-5-{[(1S)-1-[3-(trifluoromethoxy)phenyl]ethyl]-carbamoyl}pyridin-3-yl]-N-(deutero)-methyl-1H-indazole-3-carboxamide | OCF₃ phenyl | 520.3 |
| 221 | 6-[6-(deutero)methoxy-5-{[(1S)-1-[3-(trifluoromethoxy)phenyl](2,2,2-deutero)ethyl]carbamoyl}pyridin-3-yl]-N-(deutero)methyl-1H-indazole-3-carboxamide | D₃C, OCF₃ phenyl | 523.2 |

TABLE 12-continued

Compounds in Table 12 were made in a similar fashion to examples 1 and 12. Non-delineated stereochemistry is racemic or diastereomeric unless otherwise noted in the text.

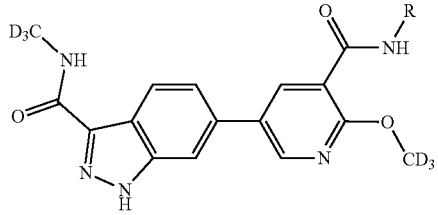

| Ex | Name | R | M + H |
|---|---|---|---|
| 222 | 6-(5-{[(1S)-1-[2-fluoro-5-(trifluoro-methoxy)phenyl](2,2,2-deutero)-ethyl]carbamoyl}-6-deutero)methoxy-pyridin-3-yl)-N-(deutero)methyl-1H-indazole-3-carboxamide | ![R group with D3C, F, OCF3] | 541.2 |
| 223 | 6-(5-{[(1S)-1-[2-fluoro-5-(trifluoro-methyl)phenyl](2,2,2-deutero)ethyl]-carbamoyl}-6-(deutero)methoxy-pyridin-3-yl)-N-(deutero)methyl-1H-indazole-3-carboxamide | ![R group with D3C, F, CF3] | 525.4 |

TABLE 13

Compounds in Table 13 were made in a similar fashion to examples 1 and 12. Non-delineated stereochemistry is racemic or diastereomeric unless otherwise noted in the text.

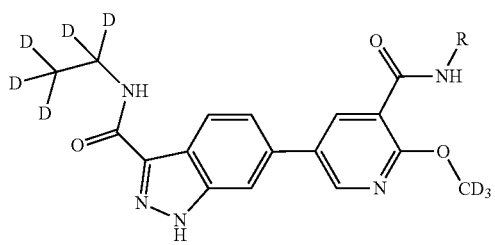

| Ex | Name | R | M + H |
|---|---|---|---|
| 224 | N-[(1,1,2,2,2-deutero)ethyl]-6-(5-{[(1S)-1-[2-fluoro-5-(trifluorometh-oxy)phenyl]ethyl]carbamoyl}-6-(deutero)methoxypyridin-3-yl)-1H-indazole-3-carboxamide | ![R group with F, OCF3] | 554.3 |
| 225 | N-[(1,1,2,2,2-deutero)ethyl]-6-(5-{[(1R)-1-[2-fluoro-5-(trifluoro-methoxy)phenyl]ethyl]carbamoyl}-6-(deutero)methoxypyridin-3-yl)-1H-indazole-3-carboxamide | ![R group with F, OCF3] | 553.8 |

TABLE 13-continued

Compounds in Table 13 were made in a similar fashion to examples 1 and 12. Non-delineated stereochemistry is racemic or diastereomeric unless otherwise noted in the text.

| Ex | Name | R | M + H |
|---|---|---|---|
| 226 | N-[(1,1,2,2,2-deutero)ethyl]-6-(5-{[(1S)-1-[2-fluoro-5-(trifluoro-methyl)phenyl]ethyl]carbamoyl}-6-(deutero)methoxypyridin-3-yl)1H-indazole-3-carboxamide | | 538.0 |
| 227 | N-[(1,1,2,2,2-deutero)ethyl]-6-(5-{[(1R)-1-[2-fluoro-5-(trifluoro-methyl)phenyl]ethyl]carbamoyl}-6-(deutero)methoxypyridin-3-yl)-1H-indazole-3-carboxamide | | 537.9 |
| 228 | N-[(1,1,2,2,2-deutero)ethyl]-6-[5-({1-[5-fluoro-2-(trifluoromethyl)-phenyl]ethyl}carbamoyl)-6-(deutero)methoxypyridin-3-yl]-1H-indazole-3-carboxamide | | 538.1 |
| 229 | N-[(1,1,2,2,2-deutero)ethyl]-6-[6-(deutero)methoxy-5-{[(1R)-1-[3-(trifluoromethyl)phenyl]ethyl]car-bamoyl}pyridin-3-yl]-1H-indazole-3-carboxamide | | 520.2 |
| 230 | N-[(1,1,2,2,2-deutero)ethyl]-6-[6-(deutero)methoxy-5-{[(1S)-1-[3-(trifluoromethyl)phenyl]ethyl]car-bamoyl}pyridin-3-yl]-1H-indazole-3-carboxamide | | 520.1 |
| 231 | N-[(1,1,2,2,2-deutero)ethyl]-6-[6-(deutero)methoxy-5-{[(1R)-1-[3-(trifluoromethoxy)phenyl]ethyl]-carbamoyl}pyridin-3-yl]-1H-indazole-3-carboxamide | | 536.3 |
| 232 | N-[(1,1,2,2,2-deutero)ethyl]-6-[6-(deutero)methoxy-5-{[(1R)-1-[3-(trifluoromethoxy)phenyl](2,2,2-deutero)ethyl]carbamoyl}pyridin-3-yl]-1H-indazole-3-carboxamide | | 539.1 |

TABLE 13-continued

Compounds in Table 13 were made in a similar fashion to examples 1 and 12. Non-delineated stereochemistry is racemic or diastereomeric unless otherwise noted in the text.

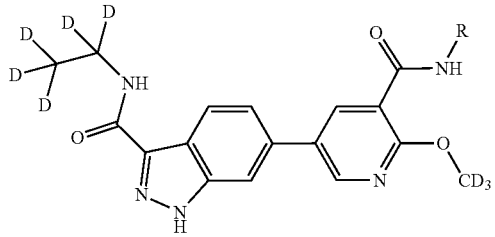

| Ex | Name | R | M + H |
|---|---|---|---|
| 233 | N-[(1,1,2,2,2-deutero)ethyl]-6-(5-{[(1R)-1-[2-fluoro-5-(trifluoromethoxy)phenyl](2,2,2-deutero)ethyl]carbamoyl}-6-(deutero)methoxypyridin-3-yl)-1H-indazole-3-carboxamide | D₃C, F, OCF₃ substituent | 557.2 |
| 234 | N-[(1,1,2,2,2-deutero)ethyl]-6-(5-{[(1R)-1-[2-fluoro-5-(trifluoromethyl)phenyl](2,2,2-deutero)ethyl]carbamoyl}-6-(deutero)methoxypyridin-3-yl)-1H-indazole-3-carboxamide | D₃C, F, CF₃ substituent | 541.3 |
| 235 | N-[(1,1,2,2,2-deutero)ethyl]-6-[6-(deutero)methoxy-5-{[(1R)-1-[2-(trifluoromethyl)phenyl]ethyl]carbamoyl}pyridin-3-yl]-1H-indazole-3-carboxamide | F₃C-phenyl substituent | 520.2 |
| 236 | N-[(1,1,2,2,2-deutero)ethyl]-6-(5-{[(1S)-1-[2-fluoro-5-(trifluoromethyl)phenyl](2,2,2-deutero)ethyl]carbamoyl}-6-(deutero)methoxypyridin-3-yl)-1H-indazole-3-carboxamide | D₃C, F, CF₃ substituent (S) | 541.2 |
| 237 | 6-(5-{[(3R)-3-(4-chlorophenyl)-3-hydroxypropyl]carbamoyl}-6-(deutero)methoxypyridin-3-yl)-N-[(1,1,2,2,2-deutero)ethyl]-1H-indazole-3-carboxamide | HO, 4-Cl-phenyl substituent | 516.2 |
| 238 | tert-butyl (3S)-3-{[5-(3-{[(1,1,2,2,2-deutero)ethyl]carbamoyl}-1H-indazol-6-yl)-2-(deutero)methoxypyridin-3-yl]formamido}butanoate | tert-butyl ester substituent | 490.3 |

What is claimed is:

1. Compounds having formula (I), or salt thereof, wherein

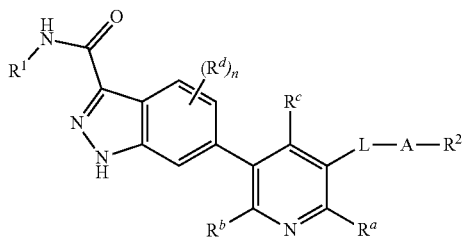

$R^a$ is H, halo, $C_{1-4}$ alkyl, $C_{1-4}$ alkoxy, $C_{1-4}$ deuteroalkyl, $C_{1-4}$ deuteroalkoxy, cyclopropyl, or $N(R^e)_2$:

$R^b$ is H, halo, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, halo, or $N(R^e)_2$;

$R^c$ is H, $C_{1-4}$ alkyl, $C_{1-4}$ haloalkyl, $C_{1-4}$ deuteroalkyl, or halo;

$R^d$ is independently H, halo, or $C_{1-3}$ alkyl;

$R^e$, is independently at each occurrence, H, $C_{1-4}$ alkyl, or $C_{1-4}$ deuteroalkyl;

$R^1$ is $C_{1-6}$ alkyl, $C_{1-6}$ haloalkyl, $C_{1-6}$ deuteroalkyl, $C_{0-3}$ alkyl-$C_{3-6}$ cycloalkyl, $C_{0-3}$ alkyl-phenyl, $C_{0-3}$ alkyl-heterocycle, wherein the heterocycle is a 3 to 6 membered ring having 1-3 heteroatoms selected from N, S and O, and wherein the alkyl, cycloalkyl, phenyl, or heterocycle are independently substituted with 0-2 of =O, halo, OH, $C_{1-3}$ alkyl, $C_{1-3}$ deuteroalkyl, —C(O)—$C_{1-3}$ alkyl, —SO$_2$—$C_{1-3}$ alkyl, —N(R$^{1e}$)$_2$, phenyl, or phenyl-O—$C_{1-3}$ alkyl;

$R^{1e}$, is independently at each occurrence, H, $C_{1-4}$ alkyl, or $C_{1-4}$ deuteroalkyl;

L is —C(O)NR$^e$—; and

A is $A^1$ or -$A^1$-$L_1$-, wherein $A^1$ is $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ deuteroalkyl, $C_{1-6}$ haloalkyl, $C_{0-3}$ alkyl-$C_{3-10}$ cycloalkyl-$C_{0-3}$-alkyl, $C_{0-3}$-alkyl-phenyl, $C_{0-3}$-alkyl-heterocycle, wherein the heterocycle is a 3 to 6 membered ring having 1-3 heteroatoms selected from N, S and O, and wherein the cycloalkyl, phenyl and heterocycle are substituted with 0-2 R$^8$;

$L^1$ is —O—, —S—, —C(O)—, —C(O)NR$^e$, —SO$_2$NH—, —NHSO$_2$—, —C(O)O—, —NR$^e$—C(O)—, —NR$^e$—C(O)O—, —NR$^e$—C(O)NR$^e$—, —SO$_2$—, or —NH—R$^e$—;

or alternatively, -L-A- is

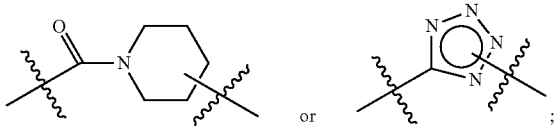

$R^2$ is $C_{1-6}$ alkyl, $C_{1-6}$ haloalkyl, $C_{0-3}$alkyl-$C_{6-10}$ aryl, $C_{0-3}$alkyl-$C_{3-6}$ cycloalkyl, or a $C_{0-3}$alkyl-3 to 6 membered heterocycle having 1-4 heteroatoms selected from N, S and O, wherein any of the aryl, cycloalkyl, or heterocycle groups are substituted with 0-3 R$^{2a}$;

$R^{2a}$ is halo, CN, =O, $C_{1-6}$ alkyl, $C_{1-6}$ alkoxy, hydroxy-$C_{1-6}$ alkoxy, $C_{1-6}$ deuteroalkyl, $C_{1-6}$ deuteroalkoxy, $C_{1-6}$ haloalkyl, $C_{1-6}$ haloalkoxy, $C_{0-3}$ alkyl-$C_{3-6}$ cycloalkyl-$C_{0-3}$ alkyl, $C_{3-6}$ halocycloalkyl, $C_{3-6}$ cycloalkoxy, $C_{3-6}$ cycloalkyl-$C_{1-6}$ alkoxy, $C_{6-10}$ aryl, phenyl-$C_{1-3}$ alkoxy-, $C_{3-6}$ cycloalkyl-$C_{1-3}$ deuteroalkoxy-, $C_{3-6}$ cycloalkyl-$C_{1-3}$ haloalkoxy-, $C_{1-6}$ alkoxy-$C_{1-3}$ alkyl-, $C_{3-6}$ cycloalkoxy-$C_{1-3}$ alkyl-, $C_{6-10}$ aryl-O—, phenyl $C_{1-4}$ alkyl-SO$_2$—, $C_{3-6}$ cycloalkyl-SO$_2$—, $C_{6-10}$ aryl-S—, NR$^6$R$^6$CO—, NHR$^6$—(CH$_2$)$_n$—, R$^5$—C(O)—, R$^5$—OC(O)—, R$^5$—C(O)O—, R$^6$—NH—C(O)O—, R$^7$—OC(O)NH—, R$^6$—NH—C(O)NR$^6$, R$^7$—SO$_2$—, R$^5$—SO$_2$NH—, R$^5$—NHSO$_2$—, heterocycle, heterocycle-O—, or heterocycle-$C_{0-6}$ alkyl-, wherein each heterocycle is independently a 4-6 membered ring having 1-2 heteroatoms selected from N, S and O, and wherein each alkyl, cycloalkyl, phenyl, or heterocycle is substituted with 0-3 R$^{2b}$;

$R^{2b}$, at each occurrence, is independently halo, OH, $C_{1-3}$ alkyl, $C_{1-3}$ alkoxy, hydroxy-$C_{1-3}$ alkoxy, hydroxy-$C_{1-3}$ alkyl, C=O, $C_{1-3}$ haloalkyl, or $C_{1-3}$ haloalkoxy;

$R^5$ is, independently at each occurrence, H, $C_{1-6}$ alkyl, $C_{0-3}$ alkyl-$C_{3-6}$ cycloalkyl, $C_{0-3}$ alkyl-phenyl or $C_{1-6}$ haloalkyl;

$R^6$ is, independently at each occurrence, H, $C_{1-6}$ alkyl, $C_{0-3}$ alkyl-$C_{3-6}$ cycloalkyl, $C_{0-3}$ alkyl-phenyl;

$R^7$ is, independently at each occurrence, $C_{1-6}$ alkyl, $C_{0-3}$ alkyl-$C_{3-6}$ cycloalkyl, $C_{0-3}$ alkyl-phenyl;

$R^8$ is, independently at each occurrence, H, halo, C=O, $C_{1-6}$ alkyl, $C_{1-6}$ alkoxy, $C_{1-6}$ haloalkyl, $C_{3-6}$ cycloalkyl, phenyl, a 3 to 6 membered heterocycle, —(CH$_2$)$_n$—NR$^6$R$^6$CO, —(CH$_2$)$_n$—NR$^6$R$^6$CONR$^6$R$^6$, —(CH$_2$)$_n$—NR$^6$, —(CH$_2$)$_n$—C(O)—R$^5$, —(CH$_2$)$_n$—C(O)O—R$^5$, —(CH$_2$)$_n$—OC(O)—R$^5$, —(CH$_2$)$_n$—OC(O)—NH—R$^6$, —(CH$_2$)$_n$—NHC(O)—O—R$^7$, —(CH$_2$)$_n$—SO$_2$—R$^7$, —(CH$_2$)$_n$—SO$_2$NH—R$^5$, —(CH$_2$)$_n$—NHSO$_2$—R$^5$, wherein each heterocycle is independently a 4-6 membered ring having 1-2 heteroatoms selected from N, S and O; and n is 0, 1, or 2.

2. A compound of claim 1, or salt thereof, wherein $R^a$ is H, Cl, F, Br, $C_{1-4}$ alkyl, $C_{1-4}$ alkoxy, $C_{1-4}$ deuteroalkyl, $C_{1-4}$ deuteroalkoxy, cyclopropyl, or $N(R^e)_2$:

$R^b$ is H, F, Cl, Br, $C_{1-4}$ alkyl, $C_{1-4}$ alkoxy, $C_{1-4}$ haloalkyl, $C_{1-4}$ haloalkoxy, $C_{1-4}$ deuteroalkyl, $C_{1-4}$ deuteroalkoxy, or NR$^e$$_2$;

$R^c$ is H, $C_{1-4}$ alkyl, $C_{1-4}$ haloalkyl, $C_{1-4}$ deuteroalkyl, or halo;

$R^d$ is independently H or F;

$R^e$, is independently at each occurrence, H, $C_{1-4}$ alkyl, or $C_{1-4}$ deuteroalkyl;

$R^1$ is $C_{1-6}$ alkyl, $C_{1-6}$ haloalkyl, $C_{1-6}$ deuteroalkyl, $C_{0-3}$ alkyl-$C_{3-6}$ cycloalkyl, $C_{0-3}$ alkyl-$C_{3-6}$ cycloalkyl, $C_{0-3}$ alkyl-piperidinyl, $C_{0-3}$ alkyl-pyrrolidinyl, $C_{0-3}$ alkyl-morpholinyl, $C_{0-3}$ alkyl-pyrrolidinyl, wherein the alkyl, cycloalkyl, piperidinyl, pyrrolidinyl, or morpholinyl are independently substituted with 0-2 of =O, halo, OH, $C_{1-3}$ alkyl, $C_{1-3}$ deuteroalkyl, phenyl, or phenyl-O—$C_{1-3}$ alkyl;

L is —C(O)NR$^e$—; and

A is $A^1$ or -$A^1$-$L^1$-, wherein $A^1$ is $C_{1-6}$ alkyl substituted with 0-1 OH, $C_{1-6}$ deuteroalkyl substituted with 0-1 OH, $C_{1-6}$ haloalkyl substituted with 0-1 OH, $C_{1-6}$ deuteroalkyl, $C_{1-6}$ haloalkyl, $C_{0-3}$ alkyl-$C_{3-10}$ cycloalkyl-$C_{0-3}$-alkyl, $C_{0-3}$-alkyl-$C_{3-6}$ cycloalkyl-$C_{0-3}$-alkyl, $C_{0-3}$-alkyl-imidazolyl, $C_{0-3}$-alkyl-pyrrolidinyl, $C_{0-3}$-alkyl-tetrahydropyranyl, $C_{0-3}$-alkyl-pyridinyl, wherein the pyrrolidinyl is substituted with 0-2 R$^8$;

L¹ is —O—, —C(O)—, —C(O)NR$^e$, —SO$_2$NH—, —C(O)O—, —NR$^e$—C(O)—, —SO$_2$—, or —N—R$^e$—;

or alternatively, -L-A- is—

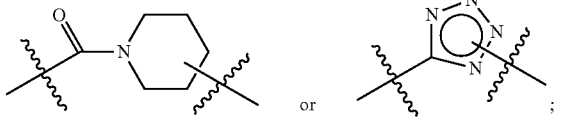

R² is C$_{1-6}$ alkyl, C$_{1-6}$ haloalkyl, C$_{0-3}$alkyl-phenyl, C$_{0-3}$alkyl-C$_{3-6}$ cycloalkyl, or a C$_{0-3}$alkyl-3 to 6 membered heterocycle having 1-4 heteroatoms selected from N, S and O, wherein any of the phenyl or heterocycle groups are substituted with 0-3 R$^{2a}$;

R$^{2a}$ is halo, CN, =O, C$_{1-6}$ alkyl, C$_{1-6}$ alkoxy, hydroxy-C$_{1-6}$ alkoxy, C$_{1-6}$ deuteroalkyl, C$_{1-6}$ deuteroalkoxy, C$_{1-6}$ haloalkyl, C$_{1-6}$ haloalkoxy, C$_{1-3}$ alkyl-C$_{3-6}$ cycloalkyl-C$_{0-3}$ alkyl, C$_{3-6}$ halocycloalkyl, C$_{3-6}$ cycloalkoxy, C$_{3-6}$ cycloalkyl-C$_{1-3}$ alkoxy-, C$_{3-6}$ cycloalkyl-C$_{1-3}$ deuteroalkoxy-, C$_{3-6}$ cycloalkyl-C$_{1-3}$ haloalkoxy-, C$_{1-6}$ alkoxy-C$_{1-3}$ alkyl-, C$_{3-6}$ cycloalkoxy-C$_{1-3}$ alkyl-, phenyl-O—, C$_{1-4}$ alkyl-SO$_2$—, C$_{3-6}$ cycloalkyl-SO$_2$—, C$_{6-10}$ aryl-S—, NR$^6$R$^6$CO—, NHR$^6$—(CH$_2$)$_n$—, R$^5$—C(O)—, R$^6$—NH—C(O)O—, R$^7$—OC(O)NH—, R$^7$—SO$_2$—, R$^5$—SO$_2$NH—, heterocycle-, heterocycle-O—, heterocycle-CH$_2$—, wherein each heterocycle is independently a 4-6 membered ring having 1-2 heteroatoms selected from N, S and O, and wherein each alkyl, cycloalkyl, phenyl, or heterocycle is substituted with 0-3 R$^{2b}$;

R$^{2b}$, at each occurrence, is independently C$_{1-3}$ alkyl, C$_{1-3}$ alkoxy, hydroxy-C$_{1-3}$ alkoxy, halo, C=O, C$_{1-3}$ haloalkyl, or C$_{1-3}$ haloalkoxy;

R$^5$ is, independently at each occurrence, H, C$_{1-6}$ alkyl, C$_{0-3}$ alkyl-C$_{3-6}$ cycloalkyl, C$_{0-3}$ alkyl-phenyl;

R$^6$ is, independently at each occurrence, H, C$_{1-6}$ alkyl, C$_{0-3}$ alkyl-C$_{3-6}$ cycloalkyl, C$_{0-3}$ alkyl-phenyl;

R$^7$ is, independently at each occurrence, H, C$_{1-6}$ alkyl, C$_{0-3}$ alkyl-C$_{3-6}$ cycloalkyl, C$_{0-3}$ alkyl-phenyl;

R$^8$ is F, =O or C$_{1-3}$ alkyl, and n is 0, 1, or 2.

3. A compound of claim 1, or salt thereof, wherein

L is —C(O)NR$^e$—; and

A is A¹ or -A¹-L¹-, wherein A¹ is C$_{1-6}$ alkyl substituted with 0-1 OH, C$_{1-6}$ deuteroalkyl substituted with 0-1 OH, C$_{1-6}$ haloalkyl substituted with 0-1 OH, C$_{1-6}$ deuteroalkyl, C$_{1-6}$ haloalkyl, C$_{0-3}$ alkyl-C$_{3-10}$ cycloalkyl-C$_{0-3}$-alkyl, C$_{0-3}$-alkyl-C$_{3-6}$ cycloalkyl-C$_{0-3}$-alkyl, C$_{0-3}$-alkyl-imidazolyl, C$_{0-3}$-alkyl-pyrrolidinyl, C$_{0-3}$-alkyl-tetrahydropyranyl, C$_{0-3}$-alkyl-pyridinyl, wherein the B pyrrolidinyl is substituted with 0-2 R$^8$.

4. A compound of claim 3, or salt thereof, wherein

R$^a$ is H, Cl, F, or C$_{1-4}$ alkyl, C$_{1-4}$ alkoxy or C$_{1-4}$ deuteroalkoxy;

R$^b$ is H, C$_{1-3}$ alkyl, or C$_{1-3}$ alkoxy; and

R$^c$ is H, or C$_{1-4}$ alkyl.

5. A compound of claim 4, or salt thereof, wherein

A¹ is C$_{1-6}$ alkyl substituted with 0-1 OH, C$_{1-6}$ deuteroalkyl substituted with 0-1 OH, or C$_{0-3}$ alkyl-C$_{3-6}$ cycloalkyl; and L¹ is —O—, —C(O)—, —C(O)NR$^e$—, or —SO$_2$NH—.

6. A compound of claim 5, or salt thereof, wherein

R$^a$ is H, C$_{1-4}$ alkyl, C$_{1-4}$ alkoxy or C$_{1-4}$ deuteroalkoxy;

R$^b$ is H, or C$_{1-3}$ alkyl; and

R$^c$ is H.

7. A compound of claim 6, or salt thereof, wherein

R¹ is C$_{1-6}$ alkyl, C$_{1-6}$ haloalkyl, C$_{1-6}$ deuteroalkyl, C$_{0-3}$ alkyl-C$_{3-6}$ cycloalkyl, C$_{0-3}$ alkyl-piperidinyl, C$_{0-3}$ alkyl-pyrrolidinyl, C$_{0-3}$ alkyl-morpholinyl, C$_{0-3}$ alkyl-pyrrolidinyl, wherein the alkyl, cycloalkyl, piperidinyl, pyrrolidinyl, or morpholinyl are independently substituted with 0-2 of =O, halo, OH, C$_{1-3}$ alkyl, C$_{1-3}$ deuteroalkyl, or N(R$^{1e}$)$_2$.

8. A compound of claim 6, or salt thereof, wherein

R¹ is C$_{1-3}$ alkyl, C$_{1-3}$ deuteroalkyl, or C$_{0-1}$ alkyl-cyclopropyl;

R² is C$_{1-6}$ alkyl, phenyl, (CH$_2$)$_n$—C$_{3-6}$ cycloalkyl, or a (CH$_2$)$_n$-3 to 6 membered heterocycle, wherein the heterocycle is selected from morpholinyl, tetrahydro-2H-pyranyl, or pyrrolidinyl, wherein any of the phenyl or heterocycle groups are substituted with 0-3 R$^{2a}$; and R$^{2a}$ is F, Cl, CN, =O, C$_{1-6}$ alkyl, C$_{1-6}$ alkoxy, C$_{1-6}$ deuteroalkyl, C$_{1-3}$ deuteroalkoxy, C$_{1-2}$haloalkyl, C$_{1-3}$ alkyl-C$_{3-6}$ cycloalkyl-C$_{0-3}$ alkyl, C$_{3-6}$ cycloalkoxy, C$_{3-6}$ cycloalkyl-C$_{1-3}$ alkoxy-, C$_{3-6}$ cycloalkyl-C$_{1-3}$ deuteroalkoxy-, C$_{3-6}$ cycloalkoxy-C$_{1-3}$ alkyl-, phenyl, C$_{1-4}$ alkyl-SO$_2$—, C$_{3-6}$ cycloalkyl-SO$_2$—, NR$^6$R$^6$CO—, NHR$^6$—(CH$_2$)$_n$—, R$^5$—C(O)—, R$^6$—OC(O)—NH—, R$^7$—NHC(O)—O—, R$^7$—SO$_2$—, R$^5$—SO$_2$NH—, —(CH$_2$)$_n$-piperizinyl, —(CH$_2$)$_n$-morpholinyl, wherein each alkyl, cycloalkyl, phenyl, or heterocycle is substituted with 0-3 R$^{2b}$.

9. A compound of claim 1, or salt thereof, wherein

L-A- is —

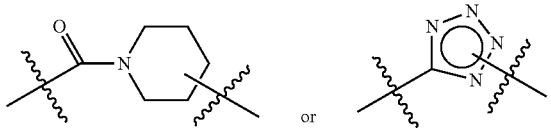

10. A compound of claim 9, or salt thereof, wherein

R$^a$ is H, Cl, F, or C$_{1-4}$ alkyl, C$_{1-4}$ alkoxy or C$_{1-4}$ deuteroalkoxy;

R$^b$ is H, C$_{1-3}$ alkyl, or C$_{1-3}$ alkoxy; and

R$^c$ is H, or C$_{1-4}$ alkyl;

R¹ is C$_{1-6}$ alkyl, C$_{1-6}$ haloalkyl, C$_{1-6}$ deuteroalkyl, C$_{0-3}$ alkyl-C$_{3-6}$ cycloalkyl, C$_{0-3}$ alkyl-piperidinyl, C$_{0-3}$ alkyl-pyrrolidinyl, C$_{0-3}$ alkyl-morpholinyl, C$_{0-3}$ alkyl-pyrrolidinyl, wherein the alkyl, cycloalkyl, piperidinyl, pyrrolidinyl, or morpholinyl are independently substituted with 0-2 of =O, halo, OH, C$_{1-3}$ alkyl, C$_{1-3}$ deuteroalkyl, or N(R$^{1e}$)$_2$;

R² is C$_{0-3}$alkyl-phenyl, C$_{0-3}$alkyl-C$_{3-6}$ cycloalkyl, or a C$_{0-3}$alkyl-3 to 6 membered heterocycle, wherein the heterocycle is selected from morpholinyl, tetrahydro-2H-pyranyl, or pyrrolidinyl, wherein any of the phenyl or heterocycle groups are substituted with 0-3 R$^{2a}$; and R$^{2a}$ is F, Cl, CN, =O, C$_{1-6}$ alkyl, C$_{1-6}$ alkoxy, C$_{1-6}$ deuteroalkyl, C$_{1-3}$ deuteroalkoxy, C$_{1-2}$haloalkyl, C$_{1-3}$ alkyl-C$_{3-6}$ cycloalkyl-C$_{0-3}$ alkyl, C$_{3-6}$ cycloalkoxy, C$_{3-6}$ cycloalkyl-C$_{1-3}$ alkoxy-, C$_{3-6}$ cycloalkyl-C$_{1-3}$ deuteroalkoxy-, C$_{3-6}$ cycloalkoxy-C$_{1-3}$ alkyl-, phenyl C$_{1-4}$ alkyl-SO$_2$—, C$_{3-6}$ cycloalkyl-SO$_2$—, NR$^6$R$^6$CO—, NR$^6$—(CH$_2$)$_n$—, R$^5$—C(O)—, R$^6$—OC(O)—NH—, R$^7$—NHC(O)—O—, R$^7$—SO$_2$—, R$^5$—SO$_2$NH—, —(CH$_2$)$_n$-piperizinyl, or —(CH$_2$)$_n$-morpholinyl, wherein each alkyl, cycloalkyl, phenyl, or heterocycle is substituted with 0-3 $R^{2b}$.

11. A compound of claim 1, or salt thereof, wherein the compound is selected from:

- N-[(1,1,2,2,2-deuteroethyl]-6-(5-{[(1S)-1-[2-fluoro-5-(trifluoromethoxy)phenyl](2,2,2-deutero)ethyl]carbamoyl}-6-(deutero)methoxypyridin-3-yl)-1H-indazole-3-carboxamide;
- (R)—N-(ethyl-d5)-6-(6-(methoxy-d3)-5-((1-(2-(trifluoromethoxy)phenyl)ethyl) carbamoyl)pyridin-3-yl)-1H-indazole-3-carboxamide;
- (R)-6-(6-(methoxy-d3)-5-((1-(3-(trifluoromethyl)phenyl) ethyl)carbamoyl)pyridin-3-yl)-N-(methyl-d3)-1H-indazole-3-carboxamide;
- (R)-6-(5-((1-(2-fluoro-5-(trifluoromethyl)phenyl)ethyl-2,2,2-d3)carbamoyl)-6-(methoxy-d3)pyridin-3-yl)-N-methyl-1H-indazole-3-carboxamide;
- (S)-6-(5-((1-(2-fluoro-5-(trifluoromethoxy)phenyl)ethyl) carbamoyl)-6-(methoxy-d3)pyridin-3-yl)-N-(methyl-d3)-1H-indazole-3-carboxamide;
- (R)-6-(5-((1-(2-fluoro-5-(trifluoromethyl)phenyl) ethyl) carbamoyl)-6-(methoxy-d3)pyridin-3-yl)-N-(methyl-d3)-1H-indazole-3-carboxamide;
- (R)-6-(6-(methoxy-d3)-5-((1-(2-(trifluoromethoxy)phenyl) ethyl)carbamoyl)pyridin-3-yl)-N-(methyl-d3)-1H-indazole-3-carboxamide;
- (R)-6-(6-(methoxy-d3)-5-((1-(3-(trifluoromethoxy) phenyl)ethyl)carbamoyl)pyridin-3-yl)-N-(methyl-d3)-1H-indazole-3-carboxamide;
- (R)-6-(5-((1-(2-fluoro-5-(trifluoromethoxy)phenyl)ethyl-2,2,2-d3)carbamoyl)-6-(methoxy-d3)pyridin-3-yl)-N-methyl-1H-indazole-3-carboxamide;
- (S)-6-(5-((1-(2-fluoro-5-(trifluoromethoxy)phenyl)ethyl-2,2,2-d3)carbamoyl)-6-(methoxy-d3)pyridin-3-yl)-N-methyl-1H-indazole-3-carboxamide;
- (R)-6-(6-(methoxy-d3)-5-((1-(3-(trifluoromethoxy)phenyl) ethyl-2,2,2-d3)carbamoyl)pyridin-3-yl)-N-methyl-1H-indazole-3-carboxamide;
- 6-(5-(((3R,4S)-1-(3,3-difluorocyclobutanecarbonyl)-4-fluoropyrrolidin-3-yl)carbamoyl)-6-methoxy d3-pyridin-3-yl)-N-methyl d3-1H-indazole-3-carboxamide;
- (R)—N-cyclopropyl-6-(6-methoxy d3-5-((1-(2-(trifluoromethoxy)phenyl)ethyl)carbamoyl)pyridin-3-yl)-1H-indazole-3-carboxamide;
- (R)-6-(6-methoxy d3-5-((1-(3-(trifluoromethoxy)phenyl) ethyl)carbamoyl)pyridin-3-yl)-N-methyl-1H-indazole-3-carboxamide;
- 6-(6-methoxy d3-5-((1-(2-(trifluoromethoxy)phenyl) ethyl)carbamoyl)pyridin-3-yl)-N-methyl-1H-indazole-3-carboxamide;
- 6-(6-methoxy D3-5-((2-(trifluoromethoxy)benzyl D2) carbamoyl)pyridin-3-yl)-N-methyl-1H-indazole-3-carboxamide;
- 6-(6-methoxy-5-((3-pivalamidocyclohexyl)carbamoyl) pyridin-3-yl)-N-methyl-1H-indazole-3-carboxamide;
- 6-(6-methoxy-5-(2-(1-phenylpropyl)-2H-tetrazol-5-yl) pyridin-3-yl)-N-methyl-1H-indazole-3-carboxamide;
- 6-(5-(2-(1-(4-fluorophenyl)ethyl)-2H-tetrazol-5-yl)-6-methoxypyridin-3-yl)-N-(methyl-d3)-1H-indazole-3-carboxamide;
- 6-[5-(2-benzyl-2H-1,2,3,4-tetrazol-5-yl)-6-methoxypyridin-3-yl]-N-methyl-1H-indazole-3-carboxamide;
- 6-{6-methoxy-5-[(3-phenylcyclohexyl)carbamoyl]pyridin-3-yl}-N-methyl-1H-indazole-3-carboxamide;
- (rac)-N-isopropyl-6-(6-methoxy d3-5-((1-(2-(trifluoromethoxy)phenyl)ethyl)carbamoyl)pyridin-3-yl)-1H-indazole-3-carboxamide;
- N-(4-(dimethyl d6-amino)cyclohexyl)-6-(6-methoxy d3-5-((1-(3-(trifluoromethoxy)phenyl)ethyl)carbamoyl)pyridin-3-yl)-1H-indazole-3-carboxamide;
- 4-fluoro-6-[6-methoxy-5-({1-[2-(trifluoromethoxy)phenyl]ethyl}carbamoyl)pyridin-3-yl]-N-methyl-1H-indazole-3-carboxamide;
- 6-[6-(deutero)methoxy-5-{[(1S)-1-[3-(trifluoromethoxy) phenyl]ethyl]carbamoyl}pyridin-3-yl]-N-methyl-1H-indazole-3-carboxamide;
- tert-butyl 3-{[2-(deutero)methoxy-5-[3-(methylcarbamoyl)-1H-indazol-6-yl]pyridin-3-yl] formamido}propanoate;
- 6-(5-{[(3S)-3-(4-chlorophenyl)-3-hydroxypropyl]carbamoyl}-6-(deutero)methoxypyridin-3-yl)-N-methyl-1H-indazole-3-carboxamide;
- tert-butyl 3-{[2-(deutero)methoxy-5-[3-(methylcarbamoyl)-1H-indazol-6-yl]pyridin-3-yl]formamido}-2,2-dimethylpropanoate;
- tert-butyl (3R)-3-{[2-(deutero)methoxy-5-[3-(methylcarbamoyl)-1H-indazol-6-yl]pyridin-3-yl] formamido}butanoate;
- 6-(5-{[(1R)-1-[2-fluoro-5-(trifluoromethoxy)phenyl] ethyl]carbamoyl}-6-(deutero)methoxypyridin-3-yl)-N-methyl-1H-indazole-3-carboxamide;
- 6-(5-{[(1R)-1-[2-fluoro-5-(trifluoromethyl)phenyl]ethyl] carbamoyl}-6-(deutero)methoxypyridin-3-yl)-N-methyl-1H-indazole-3-carboxamide;
- 6-(5-{[(1S)-1-[2-fluoro-5-(trifluoromethyl)phenyl]ethyl] carbamoyl}-6-(deutero)methoxypyridin-3-yl)-N-methyl-1H-indazole-3-carboxamide;
- 6-[6-(deutero)methoxy-5-{[(1R)-1-[2-(trifluoromethyl) phenyl]ethyl]carbamoyl}pyridin-3-yl]-N-methyl-1H-indazole-3-carboxamide;
- 6-[6-(deutero)methoxy-5-{[(1R)-1-[3-(trifluoromethyl) phenyl]ethyl]carbamoyl}pyridin-3-yl]-N-methyl-1H-indazole-3-carboxamide;
- 6-[6-(deutero)methoxy-5-{[(1S)-1-[3-(trifluoromethyl) phenyl]ethyl]carbamoyl}pyridin-3-yl]-N-methyl-1H-indazole-3-carboxamide;
- 6-[5-({1-[5-fluoro-2-(trifluoromethyl)phenyl] ethyl}carbamoyl)-6-(deutero)methoxypyridin-3-yl]-N-methyl-1H-indazole-3-carboxamide;
- 6-{6-methoxy-5-[(3-phenylbutyl)carbamoyl]pyridin-3-yl}-N-methyl-1H-indazole-3-carboxamide;
- 6-(5-{[3-hydroxy-3-(4-methoxyphenyl)propyl]carbamoyl}-6-methoxypyridin-3-yl)-N-methyl-1H-indazole-3-carboxamide;
- 6-(5-{[3-(3,4-difluorophenyl)-3-hydroxypropyl]carbamoyl}-6-methoxypyridin-3-yl)-N-methyl-1H-indazole-3-carboxamide;
- 6-(5-{[3-(4-fluorophenyl)-3-hydroxypropyl]carbamoyl}-6-methoxypyridin-3-yl)-N-methyl-1H-indazole-3-carboxamide;
- 6-(5-{[3-(4-fluorophenyl)butyl]carbamoyl}-6-methoxypyridin-3-yl)-N-methyl-1H-indazole-3-carboxamide;
- 6-[5-({[2-(3-fluorophenyl)cyclopropyl] methyl}carbamoyl)-6-methoxypyridin-3-yl]-N-methyl-1H-indazole-3-carboxamide;
- 6-[5-({[(1S,2S)-2-(4-fluorophenyl)cyclopropyl] methyl}carbamoyl)-6-methoxypyridin-3-yl]-N-methyl-1H-indazole-3-carboxamide;
- 6-[5-({[(1S,2S)-2-(4-fluorophenyl)cyclopropyl] methyl}carbamoyl)-6-methoxypyridin-3-yl]-N-methyl-1H-indazole-3-carboxamide;
- 6-(6-methoxy-5-{[(1R,2S)-2-phenylcyclopropyl] carbamoyl}pyridin-3-yl)-N-methyl-1H-indazole-3-carboxamide;

6-(6-methoxy-5-{[(1S,2R)-2-phenylcyclopropyl]carbamoyl}pyridin-3-yl)-N-methyl-1H-indazole-3-carboxamide;

6-(6-methoxy-5-{[2-(phenylsulfamoyl)ethyl]carbamoyl}pyridin-3-yl)-N-methyl-1H-indazole-3-carboxamide;

6-[5-({[2-(3-fluorophenyl)cyclopropyl]methyl}carbamoyl)-6-methoxypyridin-3-yl]-N-methyl-1H-indazole-3-carboxamide, cis;

6-[5-({[2-(3-fluorophenyl)cyclopropyl]methyl}carbamoyl)-6-methoxypyridin-3-yl]-N-methyl-1H-indazole-3-carboxamide, cis;

6-[5-({[4-fluoro-2-(oxan-4-yloxy)phenyl]methyl}carbamoyl)-6-methoxypyridin-3-yl]-N-methyl-1H-indazole-3-carboxamide;

6-[6-methoxy-5-({[(1S,2R)-2-phenylcyclopropyl]methyl}carbamoyl)pyridin-3-yl]-N-methyl-1H-indazole-3-carboxamide;

6-[6-methoxy-5-({[(1R,2S)-2-phenylcyclopropyl]methyl}carbamoyl)pyridin-3-yl]-N-methyl-1H-indazole-3-carboxamide;

6-[6-methoxy-5-({[2-(morpholin-4-yl)phenyl]methyl}carbamoyl)pyridin-3-yl]-N-methyl-1H-indazole-3-carboxamide;

6-{5-[({2-[(dimethylamino)methyl]phenyl}methyl)carbamoyl]-6-methoxypyridin-3-yl}-N-methyl-1H-indazole-3-carboxamide;

6-{6-methoxy-5-[(3-phenoxypropyl)carbamoyl]pyridin-3-yl}-N-methyl-1H-indazole-3-carboxamide;

6-{5-[(2-hydroxy-3-phenoxypropyl)carbamoyl]-6-methoxypyridin-3-yl}-N-methyl-1H-indazole-3-carboxamide;

6-{5-[({2-[4-(hydroxymethyl)piperidin-1-yl]phenyl}methyl)carbamoyl]-6-methoxypyridin-3-yl}-N-methyl-1H-indazole-3-carboxamide;

6-(6-methoxy-5-{[(2-methoxyphenyl)methyl]carbamoyl}pyridin-3-yl)-N-methyl-1H-indazole-3-carboxamide;

6-[6-methoxy-5-({[2-(2-methylpropoxy)phenyl]methyl}carbamoyl)pyridin-3-yl]-N-methyl-1H-indazole-3-carboxamide;

6-(5-{[3-(tert-butoxy)propyl]carbamoyl}-6-methoxypyridin-3-yl)-N-methyl-1H-indazole-3-carboxamide;

6-(6-methoxy-5-{[3-(oxan-2-yloxy)propyl]carbamoyl}pyridin-3-yl)-N-methyl-1H-indazole-3-carboxamide;

6-(5-{[3-(cyclohexyloxy)propyl]carbamoyl}-6-methoxypyridin-3-yl)-N-methyl-1H-indazole-3-carboxamide;

6-(5-{[3-(4-fluorophenoxy)propyl]carbamoyl}-6-methoxypyridin-3-yl)-N-methyl-1H-indazole-3-carboxamide;

6-(6-methoxy-5-{[3-(2-methylpropoxy)propyl]carbamoyl}pyridin-3-yl)-N-methyl-1H-indazole-3-carboxamide;

6-(5-{[3-(5-chloropyridin-2-yl)-3-hydroxypropyl]carbamoyl}-6-methoxypyridin-3-yl)-N-methyl-1H-indazole-3-carboxamide;

6-(5-{[(2-methanesulfonylphenyl)methyl]carbamoyl}-6-methoxypyridin-3-yl)-N-methyl-1H-indazole-3-carboxamide;

6-(6-methoxy-5-{[(1S,3R)-3-phenylcyclopentyl]carbamoyl}pyridin-3-yl)-N-methyl-1H-indazole-3-carboxamide;

6-[6-methoxy-5-({[1-(phenoxymethyl)cyclopropyl]methyl}carbamoyl)pyridin-3-yl]-N-methyl-1H-indazole-3-carboxamide;

6-[6-methoxy-5-({[2-(propane-1-sulfonyl)phenyl]methyl}carbamoyl)pyridin-3-yl]-N-methyl-1H-indazole-3-carboxamide;

6-[5-({[(1R,2R)-2-(4-fluorophenyl)cyclopropyl]methyl}carbamoyl)-6-methoxypyridin-3-yl]-N-methyl-1H-indazole-3-carboxamide, trans;

6-[5-({[1-(4-fluorophenyl)cyclopropyl]methyl}carbamoyl)-6-methoxypyridin-3-yl]-N-methyl-1H-indazole-3-carboxamide;

6-{6-methoxy-5-[({1-[2-(trifluoromethoxy)phenyl]cyclopropyl}methyl)carbamoyl]pyridin-3-yl}-N-methyl-1H-indazole-3-carboxamide;

tert-butyl N-{2-[({2-methoxy-5-[3-(methylcarbamoyl)-1H-indazol-6-yl]pyridin-3-yl}formamido)methyl]phenyl}carbamate;

tert-butyl 3-({2-methoxy-5-[3-(methylcarbamoyl)-1H-indazol-6-yl]pyridin-3-yl}formamido)propanoate;

6-[6-methoxy-5-({[2-(2,2,2-trifluoroethoxy)phenyl]methyl}carbamoyl)pyridin-3-yl]-N-methyl-1H-indazole-3-carboxamide;

6-[6-methoxy-5-({[2-methoxy-5-(trifluoromethyl)phenyl]methyl}carbamoyl)pyridin-3-yl]-N-methyl-1H-indazole-3-carboxamide;

tert-butyl N-[(1R,2S)-2-[({2-methoxy-5-[3-(methylcarbamoyl)-1H-indazol-6-yl]pyridin-3-yl}formamido)methyl]cyclohexyl]carbamate;

6-[5-({[2-(difluoromethoxy)phenyl]methyl}carbamoyl)-6-methoxypyridin-3-yl]-N-methyl-1H-indazole-3-carboxamide;

6-(6-methoxy-5-{[(2-phenyloxan-3-yl)methyl]carbamoyl}pyridin-3-yl)-N-methyl-1H-indazole-3-carboxamide;

6-[6-methoxy-5-({[2-(propane-2-sulfonyl)phenyl]methyl}carbamoyl)pyridin-3-yl]-N-methyl-1H-indazole-3-carboxamide;

6-(5-{[(2,2-dimethylcyclohexyl)methyl]carbamoyl}-6-methoxypyridin-3-yl)-N-methyl-1H-indazole-3-carboxamide;

6-(5-{[(2-ethylphenyl)methyl]carbamoyl}-6-methoxypyridin-3-yl)-N-methyl-1H-indazole-3-carboxamide;

6-(5-{[(2-tert-butyloxan-3-yl)methyl]carbamoyl}-6-methoxypyridin-3-yl)-N-methyl-1H-indazole-3-carboxamide;

6-(5-{[(2-cyanophenyl)methyl]carbamoyl}-6-methoxypyridin-3-yl)-N-methyl-1H-indazole-3-carboxamide;

6-[5-({[2-(cyclopropylsulfamoyl)phenyl]methyl}carbamoyl)-6-methoxypyridin-3-yl]-N-methyl-1H-indazole-3-carboxamide;

6-[5-({[2-(cyclobutylmethoxy)phenyl]methyl}carbamoyl)-6-methoxypyridin-3-yl]-N-methyl-1H-indazole-3-carboxamide;

6-(6-methoxy-5-{[3-(2,2,2-trifluoroethoxy)cyclohexyl]carbamoyl}pyridin-3-yl)-N-methyl-1H-indazole-3-carboxamide;

ethyl 3-({2-methoxy-5-[3-(methylcarbamoyl)-1H-indazol-6-yl]pyridin-3-yl}formamido)-2,2-dimethylpropanoate;

6-(5-{[(3,5-difluoro-2-methoxyphenyl)methyl]carbamoyl}-6-methoxypyridin-3-yl)-N-methyl-1H-indazole-3-carboxamide;

tert-butyl 3-({2-methoxy-5-[3-(methylcarbamoyl)-1H-indazol-6-yl]pyridin-3-yl}formamido)-2,2-dimethylpropanoate;

6-{5-[(2-{[(4-fluorophenyl)methyl]carbamoyl}-2,2-dimethylethyl)carbamoyl]-6-methoxypyridin-3-yl}-N-methyl-1H-indazole-3-carboxamide;

6-[6-methoxy-5-({[3-(trifluoromethoxy)phenyl]methyl}carbamoyl)pyridin-3-yl]-N-methyl-1H-indazole-3-carboxamide;

-[6-methoxy-5-({[2-(propan-2-yloxy)phenyl]methyl}carbamoyl)pyridin-3-yl]-N-methyl-1H-indazole-3-carboxamide;

6-(6-methoxy-5-{[(2-methoxypyridin-3-yl)methyl]carbamoyl}pyridin-3-yl)-N-methyl-1H-indazole-3-carboxamide;

6-{6-methoxy-5-[(3-phenyladamantan-1-yl)carbamoyl]pyridin-3-yl}-N-methyl-1H-indazole-3-carboxamide;

6-[6-methoxy-5-({[1-(3,3,3-trifluoro-2,2-dimethylpropanoyl)pyrrolidin-2-yl]methyl}carbamoyl)pyridin-3-yl]-N-methyl-1H-indazole-3-carboxamide;

6-[6-methoxy-5-({1-[3-(trifluoromethoxy)phenyl]ethyl}carbamoyl)pyridin-3-yl]-N-methyl-1H-indazole-3-carboxamide;

6-(6-methoxy-5-{[3-(morpholine-4-carbonyl)cyclohexyl]carbamoyl}pyridin-3-yl)-N-methyl-1H-indazole-3-carboxamide;

6-(6-methoxy-5-{[3-(pyrrolidine-1-carbonyl)cyclohexyl]carbamoyl}pyridin-3-yl)-N-methyl-1H-indazole-3-carboxamide;

6-[6-methoxy-5-({1-[3-(trifluoromethyl)phenyl]ethyl}carbamoyl)pyridin-3-yl]-N-methyl-1H-indazole-3-carboxamide;

6-[6-methoxy-5-({[3-(trifluoromethyl)phenyl]methyl}carbamoyl)pyridin-3-yl]-N-methyl-1H-indazole-3-carboxamide;

6-(5-{[2,2-difluoro-3-(propan-2-yloxy)propyl]carbamoyl}-6-methoxypyridin-3-yl)-N-methyl-1H-indazole-3-carboxamide;

6-[5-({[4-fluoro-3-(trifluoromethyl)phenyl]methyl}carbamoyl)-6-methoxypyridin-3-yl]-N-methyl-1H-indazole-3-carboxamide;

6-[5-({1-[4-fluoro-3-(trifluoromethyl)phenyl]ethyl}carbamoyl)-6-methoxypyridin-3-yl]-N-methyl-1H-indazole-3-carboxamide;

6-[5-({[3-(cyclopropylmethoxy)phenyl]methyl}carbamoyl)-6-methoxypyridin-3-yl]-N-methyl-1H-indazole-3-carboxamide;

6-[5-({[3-(cyclopentyloxy)phenyl]methyl}carbamoyl)-6-methoxypyridin-3-yl]-N-methyl-1H-indazole-3-carboxamide;

6-[6-methoxy-5-({[2-(trifluoromethyl)phenyl]methyl}carbamoyl)pyridin-3-yl]-N-methyl-1H-indazole-3-carboxamide;

6-[6-methoxy-5-({1-[2-(trifluoromethyl)phenyl]ethyl}carbamoyl)pyridin-3-yl]-N-methyl-1H-indazole-3-carboxamide;

6-[5-({[2-(cyclopentylmethoxy)phenyl]methyl}carbamoyl)-6-methoxypyridin-3-yl]-N-methyl-1H-indazole-3-carboxamide;

6-[6-methoxy-5-({[3-(propan-2-yloxy)phenyl]methyl}carbamoyl)pyridin-3-yl]-N-methyl-1H-indazole-3-carboxamide;

6-[5-({[2-(cyclobutylmethoxy)pyridin-3-yl]methyl}carbamoyl)-6-methoxypyridin-3-yl]-N-methyl-1H-indazole-3-carboxamide;

6-[5-({[2-(cyclohexyloxy)phenyl]methyl}carbamoyl)-6-methoxypyridin-3-yl]-N-methyl-1H-indazole-3-carboxamide;

6-[5-({[2-fluoro-3-(trifluoromethyl)phenyl]methyl}carbamoyl)-6-methoxypyridin-3-yl]-N-methyl-1H-indazole-3-carboxamide;

6-[5-({[3-(cyclobutylmethoxy)phenyl]methyl}carbamoyl)-6-methoxypyridin-3-yl]-N-methyl-1H-indazole-3-carboxamide;

6-(5-{[(2,2-dimethylcyclopentyl)methyl]carbamoyl}-6-methoxypyridin-3-yl)-N-methyl-1H-indazole-3-carboxamide;

6-[5-({[3-(cyclobutylmethoxy)pyridin-2-yl]methyl}carbamoyl)-6-methoxypyridin-3-yl]-N-methyl-1H-indazole-3-carboxamide;

6-{6-methoxy-5-[(3-phenoxycyclohexyl)carbamoyl]pyridin-3-yl}-N-methyl-1H-indazole-3-carboxamide;

6-[5-({[2-fluoro-3-(trifluoromethoxy)phenyl]methyl}carbamoyl)-6-methoxypyridin-3-yl]-N-methyl-1H-indazole-3-carboxamide;

6-(5-{[3-(dimethylcarbamoyl)cyclohexyl]carbamoyl}-6-methoxypyridin-3-yl)-N-methyl-1H-indazole-3-carboxamide;

6-(5-{[3-(diethylcarbamoyl)cyclohexyl]carbamoyl}-6-methoxypyridin-3-yl)-N-methyl-1H-indazole-3-carboxamide;

6-[5-({3-[ethyl(methyl)carbamoyl]cyclohexyl}carbamoyl)-6-methoxypyridin-3-yl]-N-methyl-1H-indazole-3-carboxamide;

6-[5-({3-[(cyclopropylmethyl)(propyl)carbamoyl]cyclohexyl}carbamoyl)-6-methoxypyridin-3-yl]-N-methyl-1H-indazole-3-carboxamide;

6-[5-({3-[(cyclobutylmethyl)(ethyl)carbamoyl]cyclohexyl}carbamoyl)-6-methoxypyridin-3-yl]-N-methyl-1H-indazole-3-carboxamide;

6-[5-({3-[cyclopropyl(methyl)carbamoyl]cyclohexyl}carbamoyl)-6-methoxypyridin-3-yl]-N-methyl-1H-indazole-3-carboxamide;

6-[5-({[3,5-difluoro-2-(propan-2-yloxy)phenyl]methyl}carbamoyl)-6-methoxypyridin-3-yl]-N-methyl-1H-indazole-3-carboxamide;

6-[5-({[2-fluoro-6-(propan-2-yloxy)phenyl]methyl}carbamoyl)-6-methoxypyridin-3-yl]-N-methyl-1H-indazole-3-carboxamide;

6-[5-({[2-(cyclopropylmethoxy)-3,5-difluorophenyl]methyl}carbamoyl)-6-methoxypyridin-3-yl]-N-methyl-1H-indazole-3-carboxamide;

6-[6-methoxy-5-({1-[2-(trifluoromethyl)phenyl]ethyl}carbamoyl)pyridin-3-yl]-N-methyl-1H-indazole-3-carboxamide;

6-[5-({[5-fluoro-2-(propan-2-yloxy)phenyl]methyl}carbamoyl)-6-methoxypyridin-3-yl]-N-methyl-1H-indazole-3-carboxamide;

6-{6-methoxy-5-[({2-[(3-methylcyclopentyl)oxy]phenyl}methyl)carbamoyl]pyridin-3-yl}-N-methyl-1H-indazole-3-carboxamide;

6-(5-{[3-(3,3-difluoroazetidine-1-carbonyl)cyclohexyl]carbamoyl}-6-methoxypyridin-3-yl)-N-methyl-1H-indazole-3-carboxamide;

cyclohexyl 1-[({2-methoxy-5-[3-(methylcarbamoyl)-1H-indazol-6-yl]pyridin-3-yl}formamido)methyl]cyclopropane-1-carboxylate;

6-{5-[(3S)-3-[(4-fluorophenyl)methyl]piperidine-1-carbonyl]-6-methoxypyridin-3-yl}-N-methyl-1H-indazole-3-carboxamide;

tert-butyl 4-({2-methoxy-5-[3-(methylcarbamoyl)-1H-indazol-6-yl]pyridin-3-yl}formamido)butanoate;

tert-butyl (3S)-3-{2-methoxy-5-[3-(methylcarbamoyl)-1H-indazol-6-yl]pyridine-3-amido}pyrrolidine-1-carboxylate;

6-[5-({[2-fluoro-5-(trifluoromethoxy)phenyl]methyl}carbamoyl)-6-methoxypyridin-3-yl]-N-methyl-1H-indazole-3-carboxamide;

6-{5-[(cyclohexylmethyl)carbamoyl]-6-methoxypyridin-3-yl}-N-methyl-1H-indazole-3-carboxamide;
tert-butyl (3S)-3-({2-methoxy-5-[3-(methylcarbamoyl)-1H-indazol-6-yl]pyridin-3-yl}formamido)butanoate;
cyclopentyl 1-[({2-methoxy-5-[3-(methylcarbamoyl)-1H-indazol-6-yl]pyridin-3-yl}formamido)methyl]cyclopropane-1-carboxylate;
tert-butyl (3R)-3-({2-methoxy-5-[3-(methylcarbamoyl)-1H-indazol-6-yl]pyridin-3-yl}formamido)butanoate;
6-[5-({3-[cyclopropyl(cyclopropylmethyl)carbamoyl]propyl}carbamoyl)-6-methoxypyridin-3-yl]-N-methyl-1H-indazole-3-carboxamide;
6-[6-methoxy-5-({[4-(trifluoromethyl)pyridin-2-yl]methyl}carbamoyl)pyridin-3-yl]-N-methyl-1H-indazole-3-carboxamide;
tert-butyl 3-({5-[4-fluoro-3-(methylcarbamoyl)-1H-indazol-6-yl]-2-methoxypyridin-3-yl}formamido)-2,2-dimethylpropanoate;
6-(5-{[(3S)-3-(4-chlorophenyl)-3-hydroxypropyl]carbamoyl}-6-methoxypyridin-3-yl)-4-fluoro-N-methyl-1H-indazole-3-carboxamide;
tert-butyl (3S)-3-({5-[4-fluoro-3-(methylcarbamoyl)-1H-indazol-6-yl]-2-methoxypyridin-3-yl}formamido)butanoate;
4-fluoro-6-[6-methoxy-5-({1-[3-(trifluoromethoxy)phenyl]ethyl}carbamoyl)pyridin-3-yl]-N-methyl-1H-indazole-3-carboxamide;
oxan-4-yl 3-[(2-methoxy-5-{3-[(deutero)methylcarbamoyl]-1H-indazol-6-yl}pyridin-3-yl)formamido]-2,2-dimethylpropanoate;
tert-butyl 3-[(2-methoxy-5-{3-[(deutero)methylcarbamoyl]-1H-indazol-6-yl}pyridin-3-yl)formamido]-2,2-dimethylpropanoate;
tert-butyl 3-[(2-methoxy-5-{3-[(deutero)methylcarbamoyl]-1H-indazol-6-yl}pyridin-3-yl)formamido]propanoate;
6-[6-methoxy-5-({1-[3-(trifluoromethoxy)phenyl]ethyl}carbamoyl)pyridin-3-yl]-N-(deutero)methyl-1H-indazole-3-carboxamide;
6-[6-methoxy-5-({1-[2-(trifluoromethoxy)phenyl]ethyl}carbamoyl)pyridin-3-yl]-N-(deutero)methyl-1H-indazole-3-carboxamide;
6-[6-methoxy-5-({[2-(trifluoromethoxy)phenyl]methyl}carbamoyl)pyridin-3-yl]-N-(deutero)methyl-1H-indazole-3-carboxamide;
N-methyl-6-(6-methyl-5-{[(1S,3R)-3-phenylcyclopentyl]carbamoyl}pyridin-3-yl)-1H-indazole-3-carboxamide;
N-methyl-6-[6-methyl-5-({1-[3-(trifluoromethoxy)phenyl]ethyl}carbamoyl)pyridin-3-yl]-1H-indazole-3-carboxamide;
N-methyl-6-[6-methyl-5-({1-[3-(trifluoromethoxy)phenyl]ethyl}carbamoyl)pyridin-3-yl]-1H-indazole-3-carboxamide;
6-[5-({[2-(cyclopentyloxy)-5-fluorophenyl]methyl}carbamoyl)-6-methylpyridin-3-yl]-N-methyl-1H-indazole-3-carboxamide;
6-[6-methoxy-2-methyl-5-({1-[2-(trifluoromethoxy)phenyl]ethyl}carbamoyl)pyridin-3-yl]-N-methyl-1H-indazole-3-carboxamide;
6-(5-{[(2,2-dimethylcyclopentyl)methyl]carbamoyl}-6-methoxy-2-methylpyridin-3-yl)-N-methyl-1H-indazole-3-carboxamide;
6-[6-methoxy-2-methyl-5-({[3-(trifluoromethoxy)phenyl]methyl}carbamoyl)pyridin-3-yl]-N-methyl-1H-indazole-3-carboxamide;
6-[5-({[2-fluoro-5-(trifluoromethoxy)phenyl]methyl}carbamoyl)-6-methoxy-2-methylpyridin-3-yl]-N-methyl-1H-indazole-3-carboxamide;
6-[2,6-dimethyl-5-({1-[2-(trifluoromethoxy)phenyl]ethyl}carbamoyl)pyridin-3-yl]-N-methyl-1H-indazole-3-carboxamide;
6-[2,6-dimethyl-5-({1-[3-(trifluoromethoxy)phenyl]ethyl}carbamoyl)pyridin-3-yl]-N-methyl-1H-indazole-3-carboxamide;
6-[2,6-dimethyl-5-({1-[3-(trifluoromethoxy)phenyl]ethyl}carbamoyl)pyridin-3-yl]-N-methyl-1H-indazole-3-carboxamide;
tert-butyl 3-[(5-{3-[(cyclopropylmethyl)carbamoyl]-1H-indazol-6-yl}-2-(deutero)methoxypyridin-3-yl)formamido]propanoate;
N-(cyclopropylmethyl)-6-[6-(deutero)methoxy-5-({1-[3-(trifluoromethoxy)phenyl]ethyl}carbamoyl)pyridin-3-yl]-1H-indazole-3-carboxamide;
6-(5-{[(3S)-3-(4-chlorophenyl)-3-hydroxypropyl]carbamoyl}-6-(deutero)methoxypyridin-3-yl)-N-(cyclopropylmethyl)-1H-indazole-3-carboxamide;
N-(cyclopropylmethyl)-6-[6-(deutero)methoxy-5-({1-[2-(trifluoromethoxy)phenyl]ethyl}carbamoyl)pyridin-3-yl]-1H-indazole-3-carboxamide;
N-(1-methanesulfonylpiperidin-4-yl)-6-[6-methoxy-5-({[2-(trifluoromethoxy)phenyl]methyl}carbamoyl)pyridin-3-yl]-1H-indazole-3-carboxamide;
N-ethyl-6-[6-methoxy-5-({[2-(trifluoromethoxy)phenyl]methyl}carbamoyl)pyridin-3-yl]-1H-indazole-3-carboxamide;
N-[(1R)-1-cyclopropylethyl]-6-[6-methoxy-5-({[2-(trifluoromethoxy)phenyl]methyl}carbamoyl)pyridin-3-yl]-1H-indazole-3-carboxamide;
N-(cyclopropylmethyl)-6-[6-methoxy-5-({[2-(trifluoromethoxy)phenyl]methyl}carbamoyl)pyridin-3-yl]-1H-indazole-3-carboxamide;
6-[6-methoxy-5-({[2-(trifluoromethoxy)phenyl]methyl}carbamoyl)pyridin-3-yl]-N-[3-(morpholin-4-yl)propyl]-1H-indazole-3-carboxamide;
N-cyclopropyl-6-[6-methoxy-5-({[2-(trifluoromethoxy)phenyl]methyl}carbamoyl)pyridin-3-yl]-1H-indazole-3-carboxamide;
N-butyl-6-[6-methoxy-5-({[2-(trifluoromethoxy)phenyl]methyl}carbamoyl)pyridin-3-yl]-1H-indazole-3-carboxamide;
6-[6-methoxy-5-({[2-(trifluoromethoxy)phenyl]methyl}carbamoyl)pyridin-3-yl]-N-propyl-1H-indazole-3-carboxamide;
6-[6-methoxy-5-({[2-(trifluoromethoxy)phenyl]methyl}carbamoyl)pyridin-3-yl]-N-[3-(2-oxopyrrolidin-1-yl)propyl]-1H-indazole-3-carboxamide;
6-[6-methoxy-5-({[2-(trifluoromethoxy)phenyl]methyl}carbamoyl)pyridin-3-yl]-N-(2,2,2-trifluoroethyl)-1H-indazole-3-carboxamide;
6-[6-methoxy-5-({[2-(trifluoromethoxy)phenyl]methyl}carbamoyl)pyridin-3-yl]-N-(propan-2-yl)-1H-indazole-3-carboxamide;
N-(1-acetylpiperidin-4-yl)-6-[6-methoxy-5-({[2-(trifluoromethoxy)phenyl]methyl}carbamoyl)pyridin-3-yl]-1H-indazole-3-carboxamide;
6-[6-methoxy-5-({[2-(trifluoromethoxy)phenyl]methyl}carbamoyl)pyridin-3-yl]-N-[5-oxo-1-(propan-2-yl)pyrrolidin-3-yl]-1H-indazole-3-carboxamide;
N-(2-hydroxyethyl)-6-[6-methoxy-5-({[2-(trifluoromethoxy)phenyl]methyl}carbamoyl)pyridin-3-yl]-1H-indazole-3-carboxamide;

N-[(1,1,2,2,2-deutero)ethyl]-6-[6-methoxy-5-({[2-(trifluoromethoxy)phenyl]methyl}carbamoyl)pyridin-3-yl]-1H-indazole-3-carboxamide;

N-[4-(diethylamino)cyclohexyl]-6-[6-methoxy-5-({[2-(trifluoromethoxy)phenyl]methyl}carbamoyl)pyridin-3-yl]-1H-indazole-3-carboxamide;

N-[4-(dimethylamino)cyclohexyl]-6-[6-methoxy-5-({[2-(trifluoromethoxy)phenyl]methyl}carbamoyl)pyridin-3-yl]-1H-indazole-3-carboxamide;

6-[6-methoxy-5-({[2-(trifluoromethoxy)phenyl]methyl}carbamoyl)pyridin-3-yl]-N-[1-(2-methoxyphenyl)-5-oxopyrrolidin-3-yl]-1H-indazole-3-carboxamide;

6-[6-methoxy-5-({[2-(trifluoromethoxy)phenyl]methyl}carbamoyl)pyridin-3-yl]-N-(1-methyl-5-oxopyrrolidin-3-yl)-1H-indazole-3-carboxamide;

N-{4-[di(deutero)methylamino]cyclohexyl}-6-[6-methoxy-5-({[2-(trifluoromethoxy)phenyl]methyl}carbamoyl)pyridin-3-yl]-1H-indazole-3-carboxamide;

6-[6-methoxy-5-({[2-(trifluoromethoxy)phenyl]methyl}carbamoyl)pyridin-3-yl]-N-[(1r,4r)-4-hydroxycyclohexyl]-1H-indazole-3-carboxamide;

N-cyclopropyl-6-(5-{[(3R,4S)-1-(3,3-difluorocyclobutanecarbonyl)-4-fluoropyrrolidin-3-yl]carbamoyl}-6-(deutero)methoxypyridin-3-yl)-1H-indazole-3-carboxamide;

6-(5-{[(3R,4S)-1-(3,3-difluorocyclobutanecarbonyl)-4-fluoropyrrolidin-3-yl]carbamoyl}-6-(deutero)methoxypyridin-3-yl)-N-(3,3-difluorocyclobutyl)-1H-indazole-3-carboxamide;

6-(5-{[(3R,4S)-1-(3,3-difluorocyclobutanecarbonyl)-4-fluoropyrrolidin-3-yl]carbamoyl}-6-(deutero)methoxypyridin-3-yl)-N-[(1,1,2,2,2-deutero)ethyl]-1H-indazole-3-carboxamide;

6-(5-{[(3R,4S)-1-(3,3-difluorocyclobutanecarbonyl)-4-fluoropyrrolidin-3-yl]carbamoyl}-6-(deutero)methoxypyridin-3-yl)-N-(2-fluoro-2-methylpropyl)-1H-indazole-3-carboxamide;

N-cyclopropyl-6-(5-{[(1S)-1-[2-fluoro-5-(trifluoromethyl)phenyl]ethyl]carbamoyl}-6-(deutero)methoxypyridin-3-yl)-1H-indazole-3-carboxamide;

tert-butyl (3S)-3-({5-[3-(cyclopropylcarbamoyl)-1H-indazol-6-yl]-2-(deutero)methoxypyridin-3-yl}formamido)butanoate;

tert-butyl (3R)-3-({5-[3-(cyclopropylcarbamoyl)-1H-indazol-6-yl]-2-(deutero)methoxypyridin-3-yl}formamido)butanoate;

N-cyclopropyl-6-[6-(deutero)methoxy-5-({1-[3-(trifluoromethoxy)phenyl]ethyl}carbamoyl)pyridin-3-yl]-1H-indazole-3-carboxamide;

6-(5-{[(3S)-3-(4-chlorophenyl)-3-hydroxypropyl]carbamoyl}-6-(deutero)methoxypyridin-3-yl)-N-cyclopropyl-1H-indazole-3-carboxamide;

N-cyclopropyl-6-(5-{[(3R,4S)-1-(3,3-difluorocyclopentanecarbonyl)-4-fluoropyrrolidin-3-yl]carbamoyl}-6-(deutero)methoxypyridin-3-yl)-1H-indazole-3-carboxamide;

tert-butyl 3-({5-[3-(cyclopropylcarbamoyl)-1H-indazol-6-yl]-2-(deutero)methoxypyridin-3-yl}formamido)-2,2-dimethylpropanoate;

N-cyclopropyl-6-(5-{[(1R)-1-[2-fluoro-5-(trifluoromethoxy)phenyl]ethyl]carbamoyl}-6-(deutero)methoxypyridin-3-yl)-1H-indazole-3-carboxamide;

N-cyclopropyl-6-[6-(deutero)methoxy-5-{[(1R)-1-[3-(trifluoromethoxy)phenyl]ethyl]carbamoyl}pyridin-3-yl]-1H-indazole-3-carboxamide;

N-cyclopropyl-6-(5-{[3-(3,3-difluoropyrrolidine-1-carbonyl)cyclohexyl]carbamoyl}-6-(deutero)methoxypyridin-3-yl)-1H-indazole-3-carboxamide;

N-cyclopropyl-6-[6-(deutero)methoxy-5-{[3-(pyrrolidine-1-carbonyl)cyclohexyl]carbamoyl}pyridin-3-yl]-1H-indazole-3-carboxamide;

N-cyclopropyl-6-[6-(deutero)methoxy-5-{[(1R)-1-[3-(trifluoromethoxy)phenyl](2,2,2-deutero)ethyl]carbamoyl}pyridin-3-yl]-1H-indazole-3-carboxamide;

N-cyclopropyl-6-(5-{[(1S)-1-[2-fluoro-5-(trifluoromethoxy)phenyl](2,2,2-deutero)ethyl]carbamoyl}-6-(deutero)methoxypyridin-3-yl)-1H-indazole-3-carboxamide;

N-cyclopropyl-6-(5-{[(1R)-1-[2-fluoro-5-(trifluoromethoxy)phenyl](2,2,2-deutero)ethyl]carbamoyl}-6-(deutero)methoxypyridin-3-yl)-1H-indazole-3-carboxamide;

N-cyclopropyl-6-(5-{[(1S)-1-[2-fluoro-5-(trifluoromethyl)phenyl](2,2,2-deutero)ethyl]carbamoyl}-6-(deutero)methoxypyridin-3-yl)-1H-indazole-3-carboxamide;

N-cyclopropyl-6-[6-(deutero)methoxy-5-{[(1R)-1-[2-(trifluoromethyl)phenyl]ethyl]carbamoyl}pyridin-3-yl]-1H-indazole-3-carboxamide;

N-cyclopropyl-6-[6-(deutero)methoxy-5-{[(1R)-1-[3-(trifluoromethyl)phenyl]ethyl]carbamoyl}pyridin-3-yl]-1H-indazole-3-carboxamide;

N-cyclopropyl-6-[6-(deutero)methoxy-5-{[(1S)-1-[3-(trifluoromethyl)phenyl]ethyl]carbamoyl}pyridin-3-yl]-1H-indazole-3-carboxamide;

6-[5-({1-[5-fluoro-2-(trifluoromethyl)phenyl]ethyl}carbamoyl)-6-(deutero)methoxypyridin-3-yl]-N-(deutero)methyl-1H-indazole-3-carboxamide;

6-(5-{[(1S)-1-[2-fluoro-5-(trifluoromethyl)phenyl]ethyl]carbamoyl}-6-(deutero)methoxypyridin-3-yl)-N-(deutero)methyl-1H-indazole-3-carboxamide;

6-[6-(deutero)methoxy-5-{[(1S)-1-[3-(trifluoromethyl)phenyl]ethyl]carbamoyl}pyridin-3-yl]-N-(deutero)methyl-1H-indazole-3-carboxamide;

6-(5-{[(1R)-1-[2-fluoro-5-(trifluoromethyl)phenyl](2,2,2-deutero)ethyl]carbamoyl}-6-(deutero)methoxypyridin-3-yl)-N-(deutero)methyl-1H-indazole-3-carboxamide;

6-(5-{[(1R)-1-[2-fluoro-5-(trifluoromethoxy)phenyl](2,2,2-deutero)ethyl]carbamoyl}-6-(deutero)methoxypyridin-3-yl)-N-(deutero)methyl-1H-indazole-3-carboxamide;

6-[6-(deutero)methoxy-5-{[(1R)-1-[3-(trifluoromethoxy)phenyl](2,2,2-deutero)ethyl]carbamoyl}pyridin-3-yl]-N-(deutero)methyl-1H-indazole-3-carboxamide;

6-(5-{[(1R)-1-[2-fluoro-5-(trifluoromethoxy)phenyl]ethyl]carbamoyl}-6-(deutero)methoxypyridin-3-yl)-N-(deutero)methyl-1H-indazole-3-carboxamide;

6-[6-(deutero)methoxy-5-{[(1R)-1-[2-(trifluoromethyl)phenyl]ethyl]carbamoyl}pyridin-3-yl]-N-(deutero)methyl-1H-indazole-3-carboxamide;

6-[6-(deutero)methoxy-5-{[(1S)-1-[3-(trifluoromethoxy)phenyl]ethyl]carbamoyl}pyridin-3-yl]-N-(deutero)methyl-1H-indazole-3-carboxamide;

6-[6-(deutero)methoxy-5-{[(1S)-1-[3-(trifluoromethoxy)phenyl](2,2,2-deutero)ethyl]carbamoyl}pyridin-3-yl]-N-(deutero)methyl-1H-indazole-3-carboxamide;

6-(5-{[(1S)-1-[2-fluoro-5-(trifluoromethoxy)phenyl](2,2,2-deutero)ethyl]carbamoyl}-6-(deutero)methoxypyridin-3-yl)-N-(deutero)methyl-1H-indazole-3-carboxamide;

6-(5-{[(1S)-1-[2-fluoro-5-(trifluoromethyl)phenyl](2,2,2-deutero)ethyl]carbamoyl}-6-(deutero)methoxypyridin-3-yl)-N-(deutero)methyl-1H-indazole-3-carboxamide;

N-[(1,1,2,2,2-deutero)ethyl]-6-(5-{[(1S)-1-[2-fluoro-5-(trifluoromethoxy)phenyl]ethyl]carbamoyl}-6-(deutero)methoxypyridin-3-yl)-1H-indazole-3-carboxamide;

N-[(1,1,2,2,2-deutero)ethyl]-6-(5-{[(1R)-1-[2-fluoro-5-(trifluoromethoxy)phenyl]ethyl]carbamoyl}-6-(deutero)methoxypyridin-3-yl)-1H-indazole-3-carboxamide;

N-[(1,1,2,2,2-deutero)ethyl]-6-(5-{[(1S)-1-[2-fluoro-5-(trifluoromethyl)phenyl]ethyl]carbamoyl}-6-(deutero)methoxypyridin-3-yl)-1H-indazole-3-carboxamide;

N-[(1,1,2,2,2-deutero)ethyl]-6-(5-{[(1R)-1-[2-fluoro-5-(trifluoromethyl)phenyl]ethyl]carbamoyl}-6-(deutero)methoxypyridin-3-yl)-1H-indazole-3-carboxamide;

N-[(1,1,2,2,2-deutero)ethyl]-6-[5-({1-[5-fluoro-2-(trifluoromethyl)phenyl]ethyl}carbamoyl)-6-(deutero)methoxypyridin-3-yl]-1H-indazole-3-carboxamide;

N-[(1,1,2,2,2-deutero)ethyl]-6-[6-(deutero)methoxy-5-{[(1R)-1-[3-(trifluoromethyl)phenyl]ethyl]carbamoyl}pyridin-3-yl]-1H-indazole-3-carboxamide;

N-[(1,1,2,2,2-deutero)ethyl]-6-[6-(deutero)methoxy-5-{[(1S)-1-[3-(trifluoromethyl)phenyl]ethyl]carbamoyl}pyridin-3-yl]-1H-indazole-3-carboxamide;

N-[(1,1,2,2,2-deutero)ethyl]-6-[6-(deutero)methoxy-5-{[(1R)-1-[3-(trifluoromethoxy)phenyl]ethyl]carbamoyl}pyridin-3-yl]-1H-indazole-3-carboxamide;

N-[(1,1,2,2,2-deutero)ethyl]-6-[6-(deutero)methoxy-5-{[(1R)-1-[3-(trifluoromethoxy)phenyl](2,2,2-deutero)ethyl]carbamoyl}pyridin-3-yl]-1H-indazole-3-carboxamide;

N-[(1,1,2,2,2-deutero)ethyl]-6-(5-{[(1R)-1-[2-fluoro-5-(trifluoromethoxy)phenyl](2,2,2-deutero)ethyl]carbamoyl}-6-(deutero)methoxypyridin-3-yl)-1H-indazole-3-carboxamide;

N-[(1,1,2,2,2-deutero)ethyl]-6-(5-{[(1R)-1-[2-fluoro-5-(trifluoromethyl)phenyl](2,2,2-deutero)ethyl]carbamoyl}-6-(deutero)methoxypyridin-3-yl)-1H-indazole-3-carboxamide;

N-[(1,1,2,2,2-deutero)ethyl]-6-[6-(deutero)methoxy-5-{[(1R)-1-[2-(trifluoromethyl)phenyl]ethyl]carbamoyl}pyridin-3-yl]-1H-indazole-3-carboxamide;

N-[(1,1,2,2,2-deutero)ethyl]-6-(5-{[(1S)-1-[2-fluoro-5-(trifluoromethyl)phenyl](2,2,2-deutero)ethyl]carbamoyl}-6-(deutero)methoxypyridin-3-yl)-1H-indazole-3-carboxamide;

6-(5-{[(3R)-3-(4-chlorophenyl)-3-hydroxypropyl]carbamoyl}-6-(deutero)methoxypyridin-3-yl)-N-[(1,1,2,2,2-deutero)ethyl]-1H-indazole-3-carboxamide; and tert-butyl (3S)-3-{[5-(3-{[(1,1,2,2,2-deutero)ethyl]carbamoyl}-1H-indazol-6-yl)-2-(deutero)methoxypyridin-3-yl]formamido}butanoate.

12. A pharmaceutical composition comprising one or more compounds of claim 1, or pharmaceutically acceptable salt thereof, and a pharmaceutically acceptable carrier.

\* \* \* \* \*